(12) United States Patent
Cooper

(10) Patent No.: US 10,304,670 B2
(45) Date of Patent: *May 28, 2019

(54) COMPOSITIONS, METHODS, AND KITS FOR QUANTIFYING TARGET ANALYTES IN A SAMPLE

(71) Applicant: Waters Technologies Corporation, Milford, MA (US)

(72) Inventor: Donald Peter Cooper, Macclesfield (GB)

(73) Assignee: Waters Technologies Corporation, Milford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/698,213

(22) Filed: Sep. 7, 2017

(65) Prior Publication Data

US 2018/0005808 A1 Jan. 4, 2018

Related U.S. Application Data

(63) Continuation of application No. 14/124,061, filed as application No. PCT/US2012/041124 on Jun. 6, 2012, now Pat. No. 9,768,001.

(Continued)

(30) Foreign Application Priority Data

Jun. 6, 2011 (EP) .................................. 11168854

(51) Int. Cl.
*H01J 49/00* (2006.01)
*G01N 30/86* (2006.01)
(Continued)

(52) U.S. Cl.
CPC ...... *H01J 49/0009* (2013.01); *G01N 30/8665* (2013.01); *G01N 30/72* (2013.01); *G01N 2030/045* (2013.01)

(58) Field of Classification Search
CPC ......... G01N 2030/045; G01N 2030/04; G01N 30/72; G01N 30/8665; H01J 49/0009
See application file for complete search history.

(56) References Cited

U.S. PATENT DOCUMENTS 9,768,001 B2 * 9/2017 Cooper ............... H01J 49/0009
2002/0090320 A1 7/2002 Burow et al.
(Continued)

FOREIGN PATENT DOCUMENTS

CN 1692282 A 11/2005
CN 102077092 A 5/2011
(Continued)

OTHER PUBLICATIONS

Brun, Virginie, et al., "Isotope dilution strategies for absolute quantitative proteomics," Journal of Proteomics, Jul. 21, 2009, vol. 72, No. 5, pp. 740-749.
(Continued)

*Primary Examiner* — Wyatt A Stoffa
(74) *Attorney, Agent, or Firm* — Womble Bond Dickinson (US) LLP; Deborah M. Vernon; Rebecca Barnes

(57) ABSTRACT

A method of quantifying a target analyte by mass spectrometry includes obtaining a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte. The first known quantity and the second known quantity are different, and wherein the first calibrator, the second calibrator, and the target analyte are each distinguishable in the single sample by mass spectrometry. The method also
(Continued)

includes quantifying the target analyte in the single sample using the first calibrator signal, the second calibrator signal, and the target analyte signal.

18 Claims, 29 Drawing Sheets

Related U.S. Application Data

(60) Provisional application No. 61/649,413, filed on May 21, 2012.

(51) Int. Cl.
  *G01N 30/72* (2006.01)
  *G01N 30/04* (2006.01)

(56) References Cited

U.S. PATENT DOCUMENTS

| | | | | |
|---|---|---|---|---|
| 2004/0072251 | A1* | 4/2004 | Anderson | G01N 33/6848 435/7.1 |
| 2004/0235193 | A1* | 11/2004 | Soldin | G01N 33/743 436/518 |
| 2010/0100335 | A1* | 4/2010 | Miyagawa | G01N 30/7206 702/23 |
| 2010/0167267 | A1* | 7/2010 | Schulzknappe | G01N 33/6848 435/5 |
| 2010/0190261 | A1* | 7/2010 | Matsukawa | G01N 33/6848 436/86 |
| 2010/0285593 | A1* | 11/2010 | Amoura | G01N 30/06 436/8 |
| 2010/0311097 | A1* | 12/2010 | Anderson | C07K 14/47 435/23 |
| 2011/0111513 | A1* | 5/2011 | Baumann | G01N 33/6848 436/89 |
| 2013/0040857 | A1* | 2/2013 | Anderson | G01N 33/6848 506/12 |
| 2013/0102478 | A1* | 4/2013 | Amoura | G01N 30/06 506/6 |
| 2013/0277542 | A1* | 10/2013 | Sasaki | H01J 49/0009 250/252.1 |
| 2014/0004616 | A1* | 1/2014 | Dey | G01N 30/72 436/128 |
| 2017/0082585 | A1* | 3/2017 | DeWitte | G01N 30/06 |

FOREIGN PATENT DOCUMENTS

| | | |
|---|---|---|
| JP | 2003-265181 A | 9/2003 |
| JP | 2010-527452 A | 8/2010 |
| WO | 01/032900 A1 | 5/2001 |
| WO | 02/031747 A1 | 4/2002 |
| WO | 03/078962 A2 | 9/2003 |
| WO | 2005124341 A2 | 12/2005 |
| WO | 2008156139 A1 | 12/2008 |
| WO | 2009/141310 A1 | 11/2009 |
| WO | 2011/116028 A1 | 9/2011 |
| WO | 2012093622 A1 | 7/2012 |

OTHER PUBLICATIONS

Hewavitharana, Amitha K., et al., "Matrix matching in liquid chromatography—mass spectrometry with stable isotope labelled internal standards—Is it necessary?", Journal of Chromatography, Jan. 14, 2011, vol. 1218, No. 2, pp. 359-361.

International Search Report for International Application No. PCT/US2012/041124, dated Sep. 11, 2012.

Mitamura, Kuniko et al., "Simultaneous Determination of Androstenediol 3-Sulfate and Dehydroepiandrosterone Sulfate in Human Serum Using Isotope Diluted Liquid Chromatography—Electrospray Ionization-Mass Spectrometry", Journal of Chromatography B, 2003, vol. 796, pp. 121-130.

Nilsson Lars B., et al., "Direct quantification in bioanalytical LC-MS/MS using internal calibration via analyte/stable isotope ratio," Journal of Pharmaceutical and Biomedical Analysis, Feb. 2, 2007, vol. 43, No. 3, pp. 1094-1099.

Trufelli, Helga, et al., "An Overview of Matrix Effects in Liquid Chromatography—Mass Spectrometry," Mass Spectrometry Reviews, May 1, 2011, vol. 30, No. 3, pp. 491-509.

Willis, D. E., "Internal Standard Method Calculations," Chromatographia, Jan. 1, 1972, vol. 5, No. 1, pp. 42-43.

Written Opinion of the International Searching Authority for International Application No. PCT/US2012/041124 dated Dec. 6, 2013—7 pages.

Pichler, P., et al. "Peptide Labeling with Isobaric Tags Yields Higher Identification Rates Using iTRAQ-4-Plex Compared to TMT 6-Plex and iTRAQ 8-Plex on LTQ Orbitrap" Anal. Chem. Aug. 2010 82(15) 6549-6558.

* cited by examiner

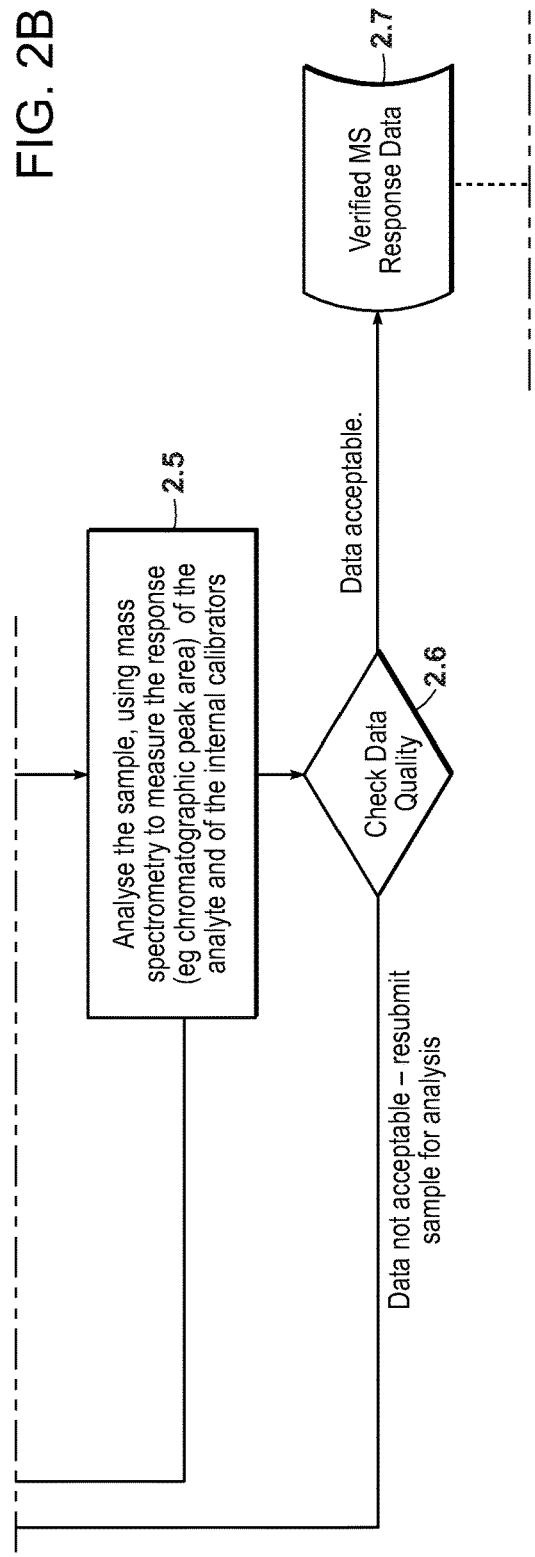

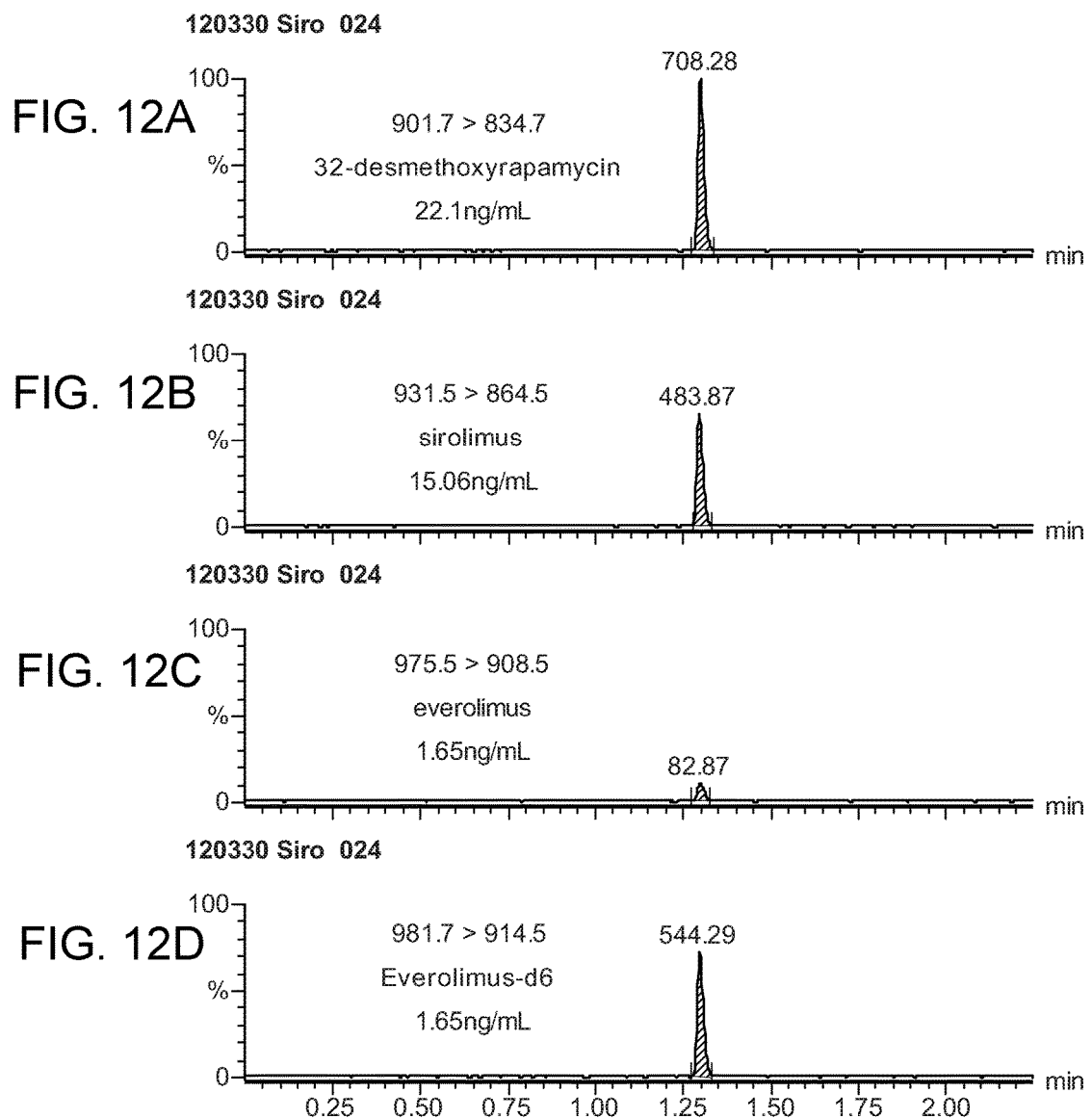

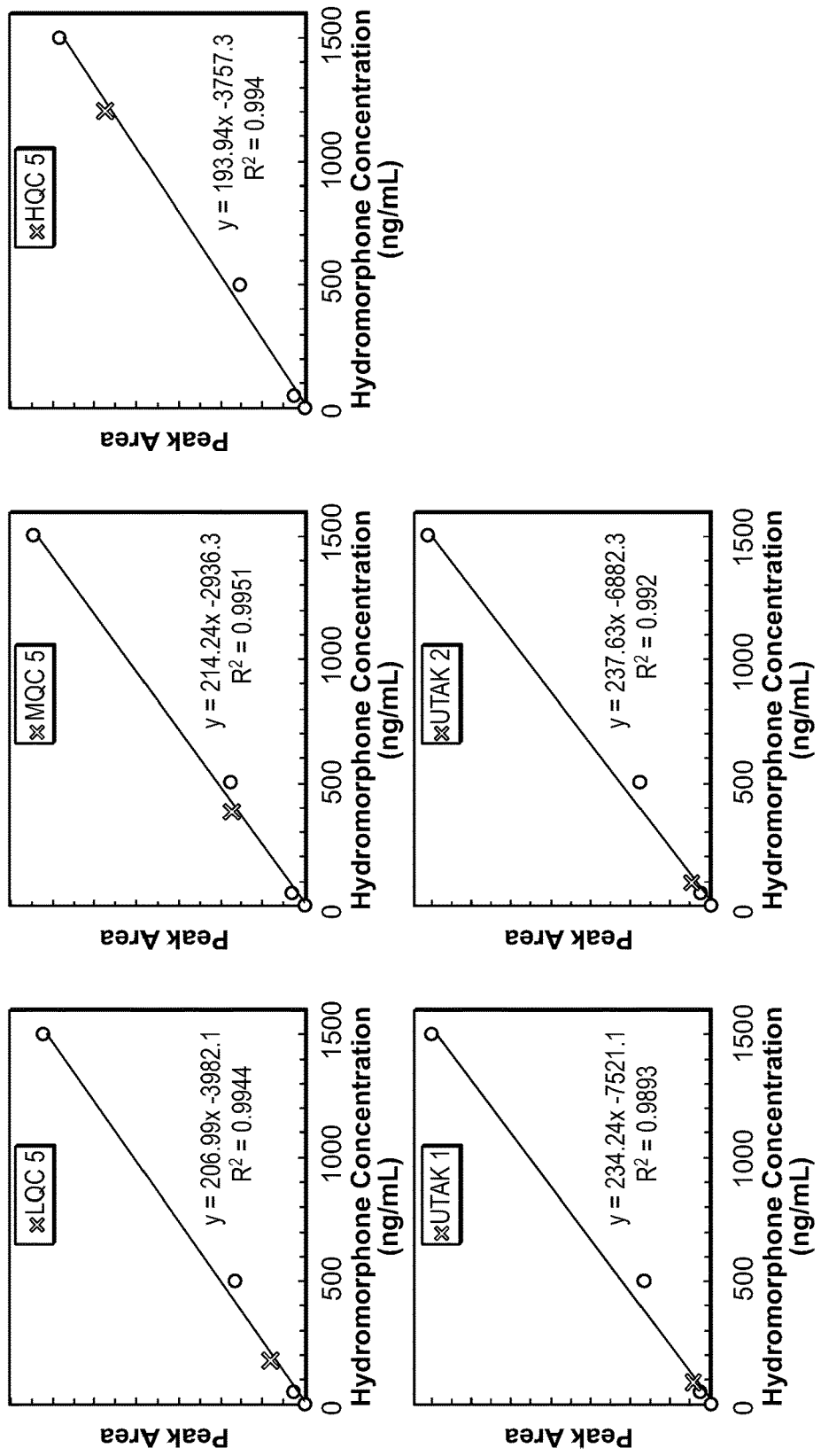

COMPOSITIONS, METHODS, AND KITS FOR QUANTIFYING TARGET ANALYTES IN A SAMPLE

RELATED APPLICATIONS

This application is a continuation of U.S. Ser. No. 14/124,061, having a 371 date of Feb. 26, 2014 and which is a U.S. National Stage application of International Application No. PCT/US2012/041124, filed Jun. 6, 2012, which claims priority to European Patent Application No. 11168854.5, filed on Jun. 6, 2011, and U.S. Provisional Application No. 61/649,413, filed on May 21, 2012. The entire contents of the foregoing applications are hereby incorporated by reference.

FIELD OF THE INVENTION

The invention relates generally to compositions, kits, methods, and apparatuses for quantifying one or more target analytes in a sample. The invention relates more particularly to mass spectrometry analysis where there is a single sample including a first known quantity of a first calibrator and a second known quantity of a second calibrator, and where the first calibrator, the second calibrator, and a corresponding target analyte are each distinguishable within the single sample by mass spectrometry.

BACKGROUND OF THE INVENTION

Mass spectrometry (MS) is a major discovery tool in the life sciences. By using this analytical technique it is possible to analyze the molecular composition of a sample by ionizing the sample or the analyte molecules contained in said sample and then measuring the mass-to-charge ratios of the resulting ions. The mass spectra obtained by an MS experiment are used to identify, characterize, and quantify the abundance of the analytes of interest. In particular, liquid chromatography-mass spectrometry (LC-MS) has recently been used for quantification of drugs and biologically active compounds, mostly because of the high selectivity, sensitivity, speed, and simplicity imparted by LC/MS/MS.

For quantification of a target analyte in a sample, it is generally necessary to first establish a calibration curve which represents the relationship between the analytical signal obtained from the particular analytical method used, e.g., peak area or peak height in MS spectra or in mass chromatograms, and the quantity of the target analyte. Thus, prior to the analysis of a sample the analytical signals of a series of calibration standards (e.g., the isolated target analyte in six different concentrations) have to be determined and this external calibration has to be done regularly (e.g., daily). However, this procedure reduces productivity, increases the costs per sample, and moreover, renders the analysis of just one sample inefficient.

SUMMARY OF THE INVENTION

The invention provides compositions, kits, methods, and apparatuses for quantifying target analytes in a sample by mass spectrometry without relying upon conventional calibration and its associated drawbacks and disadvantages. In general, the invention provides for MS analysis where there is a single sample including a first known quantity of a first calibrator and a second known quantity of a second calibrator, and where the first calibrator, the second calibrator, and the target analyte are each distinguishable within the single sample by mass spectrometry.

In addition to eliminating the inefficiency of conventional calibration, the invention addresses the issue of the matrix effects that pose a major problem for using MS in the quantitative analysis of target analytes in samples (e.g., since the matrix coextracted with the target analytes can alter the signal response, resulting in poor analytical accuracy, linearity, and reproducibility). For example, samples of different individuals may not have identical behavior in the analytic system used and may differ from the behavior of the calibration standards. Thus, an exact analysis using the conventional methods requires the provision of a matrix-based calibration standard, e.g., matrix which is free of the target analyte and which contains the calibration standard. However, such target analyte-free matrix can be difficult to obtain, in particular for target analytes that are usually expected to be present in that matrix (e.g., steroids in plasma).

Further issues with such matrix-based calibrator standards include: (i) the requirement to obtain large quantities of target analyte-free matrix in constant quality and composition; (ii) pathogen testing if the matrix is of human or animal origin; (iii) handling, storage and stability of the matrix; and (iv) handling, storage and stability of the calibrators in the matrix. Moreover, samples to be analyzed can be quite diverse in nature, for example, different bodily sample (e.g., hair and plasma). Thus, the matrixes of such diverse samples can also differ significantly, thereby requiring two different sets of calibration standards, one matched for the bodily sample and one matched for the environmental sample. Therefore, calibration standards and quantification methods that are applicable to a wide variety of samples, for example, samples which are relevant in the field of clinical chemistry (e.g., plasma for the quantification of a metabolite), environmental protection (e.g., sewage for the quantification of a pharmaceutical), or the food industry (e.g., retain sample for the study of a food sample, e.g., an edible product of animal or vegetable origin such as milk, bread, eggs, meat, or an extract thereof) are advantageous.

Whereas conventional methods can require an internal standard to be added to the sample (e.g., because the conventional calibrators are not in the sample and, thus, are subject to a different matrix than the target analyte), the invention does not require an internal standard because the internal calibrators are subject to the exact same matrix as the target analyte. For essentially the same reasons, the invention can employ fewer calibrators than conventional methods and potentially achieve the same, or superior, accuracy and/or precision.

Thus, the materials, methods, kits, and apparatuses of the invention meet the need for efficient quantification of target analytes in samples, in particular if the number of samples to be analyzed is smaller than the number of calibration standards. Furthermore, the invention also meets the need for calibration standards and quantification methods which are universally applicable to a wide variety of samples, for example, samples which are relevant in field of clinical chemistry (e.g., plasma for the quantification of a metabolite), environmental protection (e.g., sewage for the quantification of a pharmaceutical), and the food industry (e.g., an edible product of animal or vegetable origin such as milk, bread, eggs, meat, or an extract thereof).

The invention meets these, and other needs by providing compositions including two (or more) internal calibrators in differing concentrations that can be used to quantify a target analyte in a sample. The internal calibrators and the target analyte are distinguishable from each other based on their behavior in a mass spectrometer. Such calibration standards can be stable, easy to handle, and/or suitable for high-throughput analysis.

One advantage provided by the present invention is that an internal calibration within the analysis of the sample can be performed, thereby avoiding the need for an external calibration. Thus, by using internal calibration it is possible that an analyte is quantified by performing a single analysis of one sample so that each analysis yields a result thereby increasing the productivity and decreasing the costs per sample. A further advantage of at least some of the embodiments of the present invention is that the calibration standards are present in exactly the same matrix as the target analyte and thus, each sample has its own perfectly matrix-matched calibration standards, thereby reducing or eliminating matrix effects. Yet another advantage of the invention is the potential for decreasing time to result and increasing throughput, as compared to conventional methods.

The internal calibrator compositions, kits, and methods of the present invention are broadly applicable to a wide variety of samples, for example, samples which are relevant in the field of clinical chemistry (e.g., plasma for the quantification of a metabolite), environmental protection (e.g., sewage for the quantification of a pharmaceutical), and the food industry (e.g., an edible product of animal or vegetable origin such as milk, bread, eggs, meat, or an extract thereof). Furthermore, because internal calibrators are added to the sample to be analyzed, they can be processed in exactly the same way as the target analyte and thus, can be used to compensate for sample and/or analyte losses during sample preparation.

The internal calibrators include compounds which, with respect to chemical composition, structure and physicochemical properties, are similar to the corresponding target analyte but which are distinguishable from the target analyte based on the behavior of the internal calibrator and target analyte in a mass spectrometer. For example, an internal calibrator can mimic a corresponding target analyte such that at least one of the physicochemical properties of the internal calibrator is essentially identical to the corresponding physicochemical property of the target analyte. In various embodiments, the internal calibrator and its corresponding target analyte are effectively indistinguishable from each other by one or more techniques commonly used to process a sample prior to analysis in a mass spectrometer. For example, an internal calibrator and its corresponding target analyte can be indistinguishable on the basis of one or more of: solubility (in a solvent, e.g., water or an organic solvent, or a mixture of solvents), retention time (in a separation technique, such as liquid chromatography), affinity (e.g., to an antibody specific for said target analyte), dissociation constant, reactivity and/or specificity towards an enzyme (e.g., hydrolase, transferase). In some embodiments, the internal calibrator is generally absent or in a negligible (or otherwise compensable) initial amount in the sample to be analyzed. In some embodiments, the internal calibrator is generally a synthetic compound, e.g., a compound which does not naturally occur (e.g., in the sample) or the natural abundance of which is below the detection limit of a mass spectrometer.

The property of being distinguishable based upon the behavior in a mass spectrometer includes situations where two or more compounds (such as the first or second internal calibrator and the target analyte; or the first and second internal calibrators) can be distinguished from each other by a mass spectrometer due to differences in their mass (i.e., a difference in mass that can be resolved by a MS instrument, or at a given cutoff), fragmentation pattern, or combinations thereof. The difference in mass between these two compounds can originate from the presence of different isotopes (e.g., low abundant isotopes in one of the two compounds vs. high abundant isotopes in the other of the two compounds) or difference chemical moieties (e.g., different empirical formula).

Any two compounds (e.g., the first internal calibrator and the target analyte) of the two or more compounds can be distinguished from each other by a mass spectrometer due to differences in their fragmentation pattern. The two or more compounds (such as one internal calibrator and its corresponding target analyte; or two internal calibrators) can fragment during the mass spectrometric analysis essentially in the same way, thereby generating fragments similar in chemical composition and structure for isotopic analogs (for chemical analogs, the fragments can be dissimilar). In some cases, the two or more compounds can have the same mass and empirical formula, but fragments of different masses (e.g., 4D vitamin D and 2D, $2^{13}$C vitamin D).

For example, any two compounds (e.g., the first internal calibrator and the target analyte) of the two or more compounds can be distinguished from each other by a mass spectrometer due to differences in their mass (i.e., a difference in mass that can be resolved by a MS instrument, or at a given cutoff). The masses of the two compounds (e.g., the first internal calibrator and the target analyte) can differ in at least 1 (or 2, 3, 4, 5, . . . ) mass units where the two compounds are isotopic analogs. Where the compounds are chemical analogs (e.g., differing in empirical formula), the analogs can differ by less than one mass unit and/or a non-integer amount.

In one aspect, the invention features a method for quantifying a target analyte by mass spectrometry. The method includes obtaining a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte. The first known quantity and the second known quantity are different, and the first calibrator, the second calibrator, and the target analyte are each distinguishable in the single sample by mass spectrometry. The method also includes quantifying the target analyte in the single sample using the first calibrator signal, the second calibrator signal, and the target analyte signal.

In another aspect, the invention features a composition for quantifying a target analyte by mass spectrometry. The composition includes a first known quantity of a first calibrator and a second known quantity of a second calibrator, wherein the first known quantity and the second known quantity are different, and wherein the first calibrator, the second calibrator, and the target analyte are each distinguishable in the single sample by mass spectrometry.

In still another aspect, the invention features a kit for quantifying a target analyte by mass spectrometry. The kit includes a first known quantity of a first calibrator and a second known quantity of a second calibrator, wherein the first known quantity and the second known quantity are different, and wherein the first calibrator, the second calibrator, and the target analyte are each distinguishable in the single sample by mass spectrometry. The kit also includes instructions for (i) obtaining a mass spectrometer signal comprising a first calibrator signal, a second calibrator signal, and a target analyte signal from a single sample comprising the first known quantity of the first calibrator, comprising the second known quantity of the second calibrator, and potentially comprising the target analyte and (ii) quantifying the target analyte in the single sample using the first calibrator signal, the second calibrator signal, and the target analyte signal.

In yet another aspect, the invention features a computer readable medium comprising computer executable instructions (e.g., a physical embodiment of the method of the invention). The computer executable instructions are adapted to obtain a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte. The first known quantity and the second known quantity are different. The first calibrator, the second calibrator, and the target analyte are each distinguishable in the single sample by mass spectrometry. The computer executable instructions are also adapted to quantify the target analyte in the single sample using the first calibrator signal, the second calibrator signal, and the target analyte signal.

In still yet another aspect, the invention features an apparatus for quantifying a target analyte by mass spectrometry. The apparatus includes a sample handler configured to prepare the single sample by combining a first known quantity of a first calibrator and a second known quantity of a second calibrator in a single specimen potentially comprising a target analyte. The apparatus also includes a mass spectrometer configured to generate a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte, wherein the first known quantity and the second known quantity are different, and wherein the first calibrator, the second calibrator, and the target analyte are each distinguishable in the single sample by mass spectrometry. Furthermore, the apparatus includes a data processor configured to quantify the target analyte in the single sample using the first calibrator signal, the second calibrator signal, and the target analyte signal.

In various embodiments, the invention also includes (i) preparing the single sample by combining the first known quantity of the first calibrator and the second known quantity of the second calibrator in a single specimen potentially comprising the target analyte; and (ii) generating the mass spectrometer signal from the single sample using a mass spectrometer.

In some embodiments, the invention also includes separating the first calibrator, the second calibrator, and the target analyte from other components of the single sample prior to obtaining the mass spectrometer signal. The separation can include chromatography and the first calibrator, the second calibrator, and the target analyte co-elute. The separation can include chromatography and the first calibrator, the second calibrator, and the target analyte elute separately. The separation can include at least one of solid phase extraction, liquid chromatography, gas chromatography, affinity, immunoaffinity, and supercritical fluid chromatography.

In certain embodiments, the invention also includes (i) obtaining a calibration curve from the first calibrator signal and the second calibrator signal; and (ii) quantifying the target analyte using the calibration curve and the target analyte signal. The invention can include quantifying the target analyte algebraically using the first calibrator signal, the second calibrator signal, and the target analyte signal.

In various embodiments, the first calibrator and the second calibrator are each different analogs, derivatives, metabolites, or related compounds of the target analyte. The first calibrator and the second calibrator can each be different stable isotope analogs of the target analyte. For example, the internal calibrators of one or more sets of internal calibrators (e.g., the internal calibrators of all sets of internal calibrators) can be isotope-labeled analogs of the corresponding target analyte, derivatives of the corresponding target analyte, or metabolites of the corresponding target analyte, preferably isotope-labeled analogs of the corresponding target analyte. Suitable isotopes include $^{2}H$, $^{11}B$, $^{13}C$, $^{15}N$, $^{17}O$, $^{18}O$, $^{33}S$, $^{34}S$, $^{36}S$, $^{74}Se$, $^{76}Se$, $^{77}Se$, $^{78}Se$, and $^{82}Se$.

The invention includes embodiments with one or more additional internal calibrators for the target analyte (e.g., 1, 2, 3, 4, 5, 6, 7, 8, 9, etc. internal calibrators, in addition to the first and second calibrators, for the target analyte). Similarly, the invention includes embodiments for analyzing panels of two or more analytes in a single sample (e.g., with two or more additional internal calibrators for each of a second target analyte, optional third target analyte, optional fourth target analyte, optional fifth target analyte, optional sixth target analyte, optional seventh target analyte, optional eighth target analyte, optional ninth target analyte, etc.).

In some embodiments, the invention also includes (i) obtaining, from the mass spectrometer signal, a third calibrator signal, a fourth calibrator signal, and an additional target analyte signal from the single sample comprising a third known quantity of a third calibrator, comprising a fourth known quantity of a fourth calibrator, and potentially comprising an additional target analyte, wherein the third known quantity and the fourth known quantity are different, and wherein the first calibrator, the second calibrator, the third calibrator, the fourth calibrator, the target analyte, and the additional target analyte are each distinguishable in the single sample by mass spectrometry; and (ii) quantifying the additional target analyte in the single sample using the third calibrator signal, the fourth calibrator signal, and the additional target analyte signal. The invention can further include (i) obtaining, from the mass spectrometer signal, a fifth calibrator signal, a sixth calibrator signal, and a second additional target analyte signal from the single sample comprising a fifth known quantity of a fifth calibrator, comprising a sixth known quantity of a sixth calibrator, and potentially comprising a second additional target analyte, wherein the fifth known quantity and the sixth known quantity are different, and wherein the first calibrator, the second calibrator, the third calibrator, the fourth calibrator, the fifth calibrator, the sixth calibrator, the target analyte, the additional target analyte, and the second additional target analyte are each distinguishable in the single sample by mass spectrometry; and (ii) quantifying the second additional target analyte in the single sample using the fifth calibrator signal, the sixth calibrator signal, and the second additional target analyte signal.

In certain embodiments, the invention also includes (i) obtaining, from the mass spectrometer signal, a third calibrator signal from the single sample further comprising a third known quantity of a third calibrator. The first known quantity, the second known quantity, and the third known quantity are different. The first calibrator, the second calibrator, the third calibrator, and the target analyte are each distinguishable in the single sample by mass spectrometry. Quantifying the target analyte further comprises using the third calibrator. The invention can further include obtaining, from the mass spectrometer signal, a fourth calibrator signal from the single sample further comprising a fourth known quantity of a fourth calibrator. The first known quantity, the second known quantity, the third known quantity, and the fourth known quantity are different. The first calibrator, the second calibrator, the third calibrator, the fourth calibrator and the target analyte are each distinguishable in the single sample by mass spectrometry. Quantifying the target analyte further comprises using the fourth calibrator.

In various embodiments, the invention also includes a third known quantity of a third calibrator and a fourth known quantity of a fourth calibrator, wherein the third known quantity and the fourth known quantity are different, and wherein the first calibrator, the second calibrator, the third calibrator, the fourth calibrator, the target analyte, and the additional target analyte are each distinguishable in the single sample by mass spectrometry. The invention can further include a fifth known quantity of a fifth calibrator and a sixth known quantity of a sixth calibrator, wherein the fifth known quantity and the sixth known quantity are different, and wherein the first calibrator, the second calibrator, the third calibrator, the fourth calibrator, the fifth calibrator, the sixth calibrator, the target analyte, the additional target analyte, and the second additional target analyte are each distinguishable in the single sample by mass spectrometry.

In some embodiments, the invention also includes a third known quantity of a third calibrator, wherein the first known quantity, the second known quantity, and the third known quantity are different, and wherein the first calibrator, the second calibrator, the third calibrator, and the target analyte are each distinguishable in the single sample by mass spectrometry. The invention can further include a fourth known quantity of a fourth calibrator, wherein the first known quantity, the second known quantity, the third known quantity, and the fourth known quantity are different, and wherein the first calibrator, the second calibrator, the third calibrator, the fourth calibrator, and the target analyte are each distinguishable in the single sample by mass spectrometry.

In certain embodiments, the invention also includes a sample holder defining at least one sample receptacle, wherein the first known quantity of the first calibrator and the second known quantity of the second calibrator are both comprised within the at least one sample receptacle.

In various embodiments, the invention also includes a sample holder defining at least one sample receptacle, wherein the first known quantity of the first calibrator, the second known quantity of the second calibrator, the third known quantity of the third calibrator, and the fourth known quantity of the fourth calibrator are all comprised within the at least one sample receptacle.

In various embodiments, the invention also includes a third known quantity of a third calibrator and a fourth known quantity of a fourth calibrator, wherein the third known quantity and the fourth known quantity are different, and wherein the first calibrator, the second calibrator, the third calibrator, the fourth calibrator, the target analyte, and the additional target analyte are each distinguishable in the single sample by mass spectrometry; and instructions for (i) obtaining, from a mass spectrometer, a third calibrator signal, a fourth calibrator signal, and an additional target analyte signal from a single sample comprising the third known quantity of the third calibrator, comprising the fourth known quantity of the fourth calibrator, and potentially comprising the additional target analyte and (ii) quantifying the additional target analyte in the single sample using the third calibrator signal, the fourth calibrator signal, and the additional target analyte signal.

In some embodiments, the invention also includes computer executable instructions adapted to (i) direct an automated code reader to determine a listing of one or more analytes to be tested for in a given specimen based upon a code associated with the given specimen; and (ii) direct an automated calibrator system to combine the given specimen with a first known quantity of a first calibrator and a second known quantity of a second calibrator for each of the one or more analytes.

In certain embodiments, the invention also includes a separation system configured to separate the first calibrator, the second calibrator, and the target analyte from other components of the single sample prior to obtaining a mass spectrometer signal. The separation system can include at least one of solid phase extraction, liquid chromatography, gas chromatography, affinity, immunoaffinity, and supercritical fluid chromatography equipment. The extraction, chromatography, or electrophoresis device may be coupled to a mass spectrometer (on-line mode) or not (off-line mode).

In various embodiments, the sample handler further includes (i) an automated code reader configured to determine a listing of one or more analytes to be tested for in a given specimen based upon a code associated with the given specimen; and (ii) an automated calibrator system configured to combine the given specimen with a first known quantity of a first calibrator and a second known quantity of a second calibrator for each of the one or more analytes. The automated calibrator system can be configured to deliver the given specimen to a sample receptacle comprising the first known quantity of the first calibrator and the second known quantity of the second calibrator for each of the one or more analytes. The automated calibrator system can be configured to deliver the first known quantity of the first calibrator and the second known quantity of the second calibrator for each of the one or more analytes to a sample receptacle comprising the given specimen.

In certain embodiments, the target analyte is an organic molecule which comprises at least 3 carbon atoms. The target analyte can be a steroid (e.g., a steroid hormone or sex hormone, such as testosterone, cortisol, estrone, estradiol, 17-OH-progesterone or aldosterone); an immunosuppressant drug (e.g., cyclosporin A, tacrolimus, sirolimus, everolimus, or mycophenolic acid); a thyroid marker (e.g., thyroid-stimulating hormone (TSH), thyroglobulin, triiodothyronine (T3), free T3, thyroxine (T4), free T4, or ferritin); a vitamin or a metabolite thereof (e.g., 25-hydroxy-, 1,25-dihydroxy- or 24, 25-dihydroxy-form of vitamin D2 or vitamin D3); a cardiac marker (e.g., troponins or brain natriuretic peptide); alpha-fetoprotein; or a drug of abuse (e.g., opiate).

In various embodiments, the sample can include a bodily sample, an environmental sample, a food sample, a synthetic sample, or a combination thereof. Bodily samples can include a bodily fluid (e.g., plasma or urine), feces, a bodily tissue (e.g., a biopsy sample), or an extract thereof. Examples of the environmental sample include water (e.g., drinking water, river water, surface water, ground water, potable water, sewage, effluent, wastewater, or leachate), soil, air, sediment, flora, fauna, or an extract thereof. Food samples can include an edible product of animal or vegetable origin (e.g., milk, bread, eggs, or meat) or an extract thereof. Examples of synthetic samples are a sample of a reaction mixture from an industrial process, in-process sample thereof or an extract thereof. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical).

In some embodiments, the range (e.g., amount or concentration) defined by the internal calibrators for a target analyte can span the analytical range, or expected analytical range, of the target analyte in the sample. The ratio between (i) the internal calibrator being present in the highest amount and (ii) the internal calibrator being present in the lowest amount can be at least 2 (e.g., 2:1, 3:1, 4:1, 5:1, 6:1, 7:1, 8:1, 9:1, 10:1, etc.)

The present invention is described in further detail by the figures and examples below, which are used only for illustration purposes and are not limiting.

DETAILED DESCRIPTION OF THE DRAWINGS

FIG. 1 illustrates an example method for selecting internal calibrators and for combining them in proportions suitable for an analysis.

FIG. 2A-C illustrates an example method for quantifying one or more samples.

FIG. 3 shows an example apparatus in accordance with one aspect of the invention.

FIG. 4A-D shows an example of a typical chromatogram for the analysis of a sample using the internal calibration method of the present invention.

FIG. 8A-I shows individual internal calibration lines for each of the 46 serum samples analyzed, including five replicates for sample 46.

Figure 9:
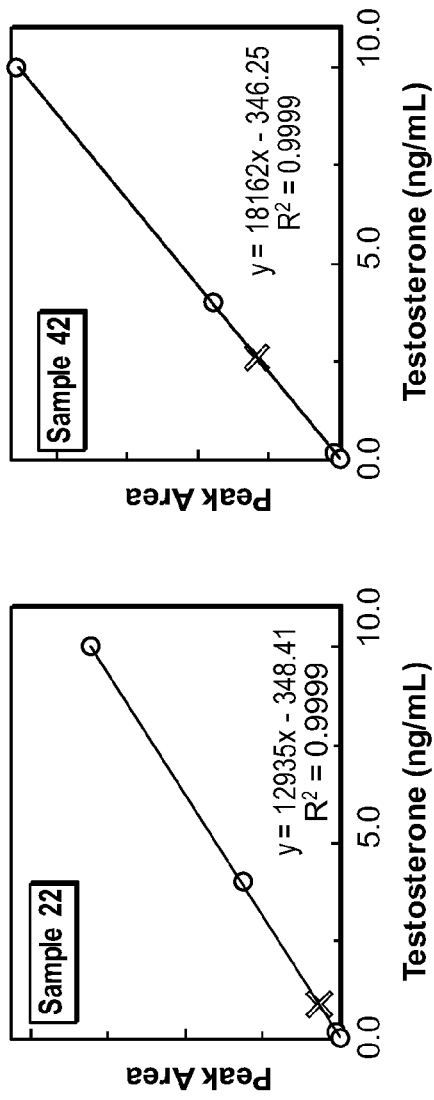

FIG. 9 shows individual internal calibration lines for serum samples 22 and 42 that correspond to the minimum and maximum slopes observed.

Figure 10:
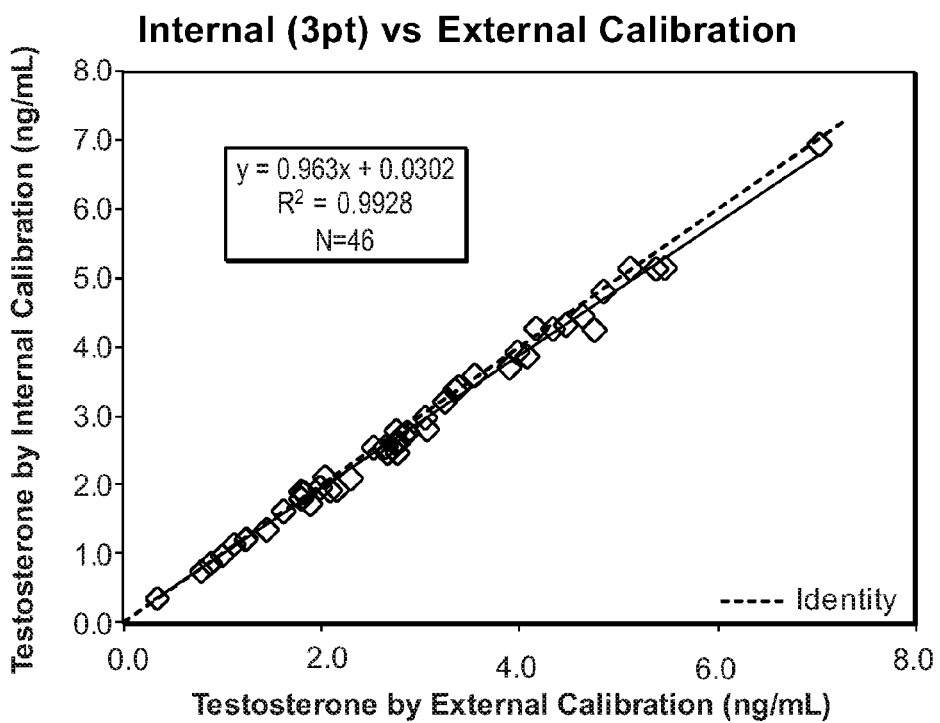

FIG. 10 shows a comparison of testosterone concentrations determined in 46 serum samples using external calibration and internal calibration with three internal calibrators.

Figure 11:
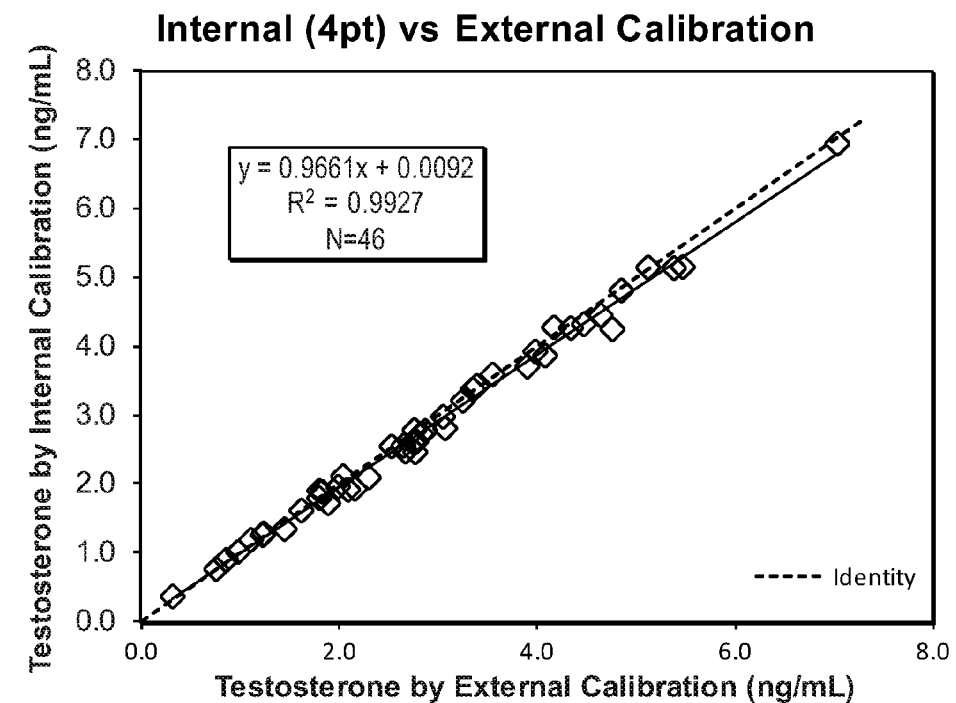

FIG. 11 shows a comparison of testosterone concentrations determined in 46 serum samples using external calibration and internal calibration with three internal calibrators plus the origin.

FIG. 12A-D shows an example mass chromatogram from Experiment 2 using the LC and MS/MS conditions described Tables 11 and 12. The integrated peak areas determined by TargetLynx are given above the chromatographic peaks for each internal calibrator and the analyte.

Figure 13A:
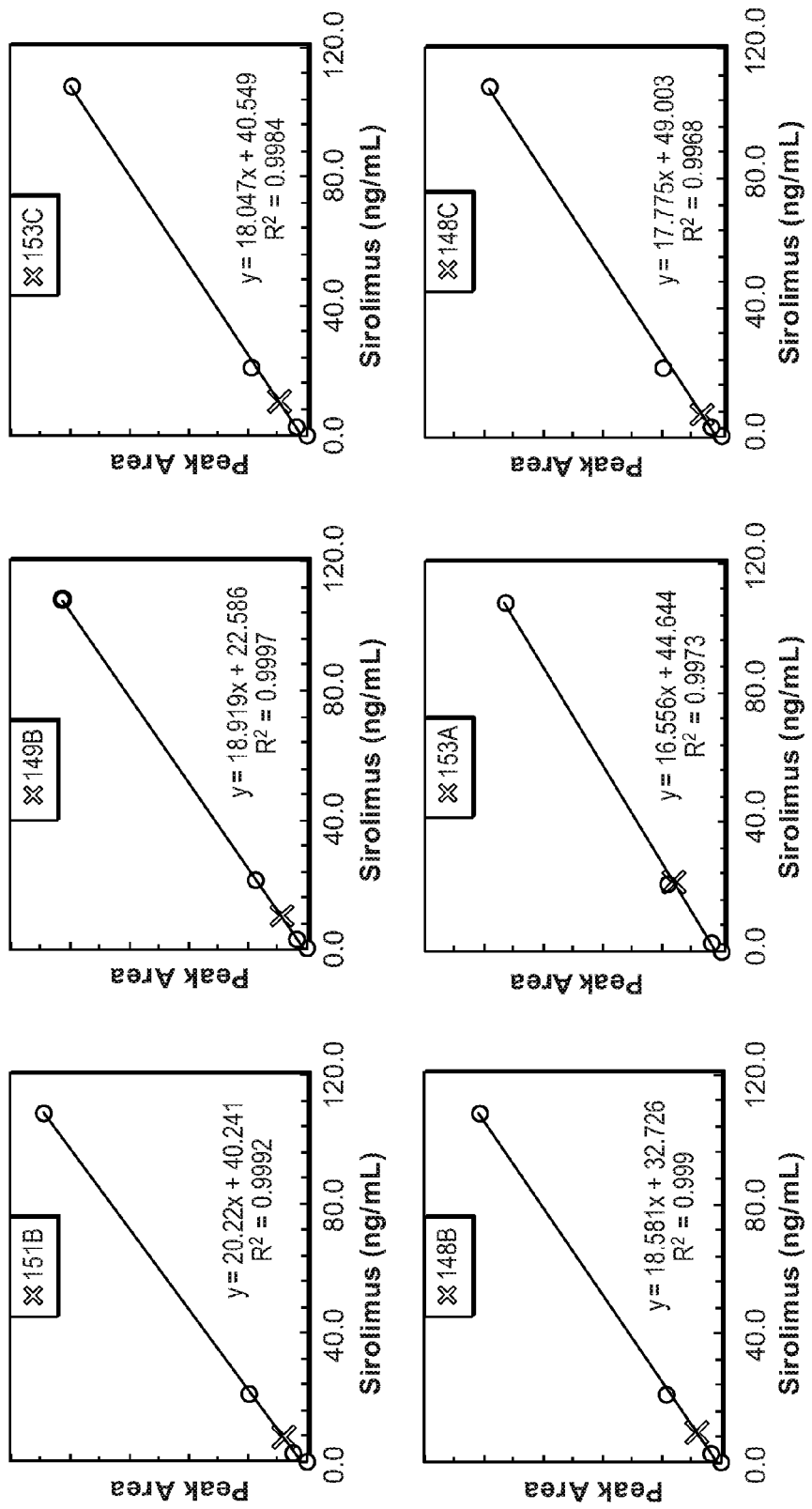
Figure 13B:
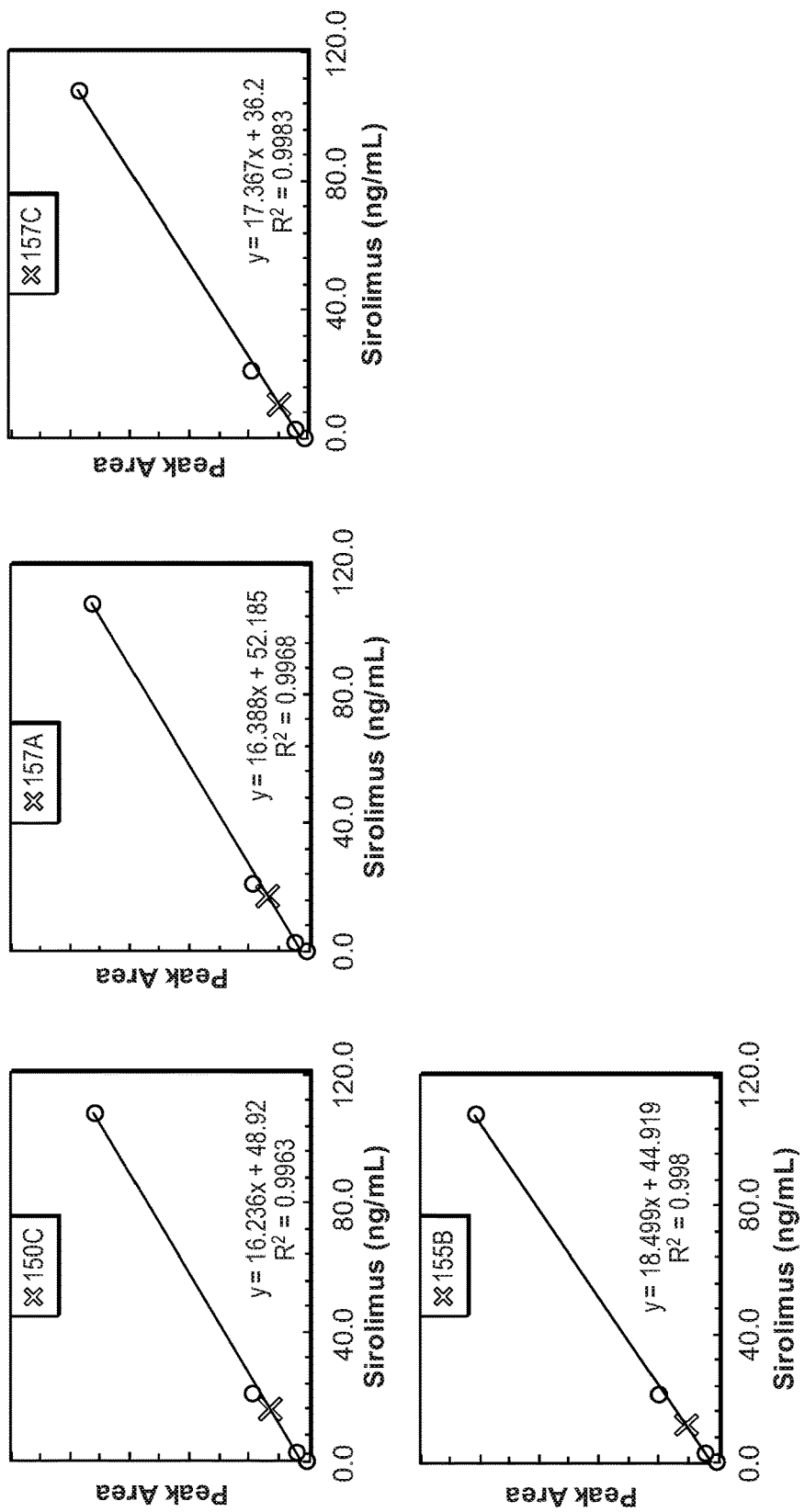
Figure 14A:
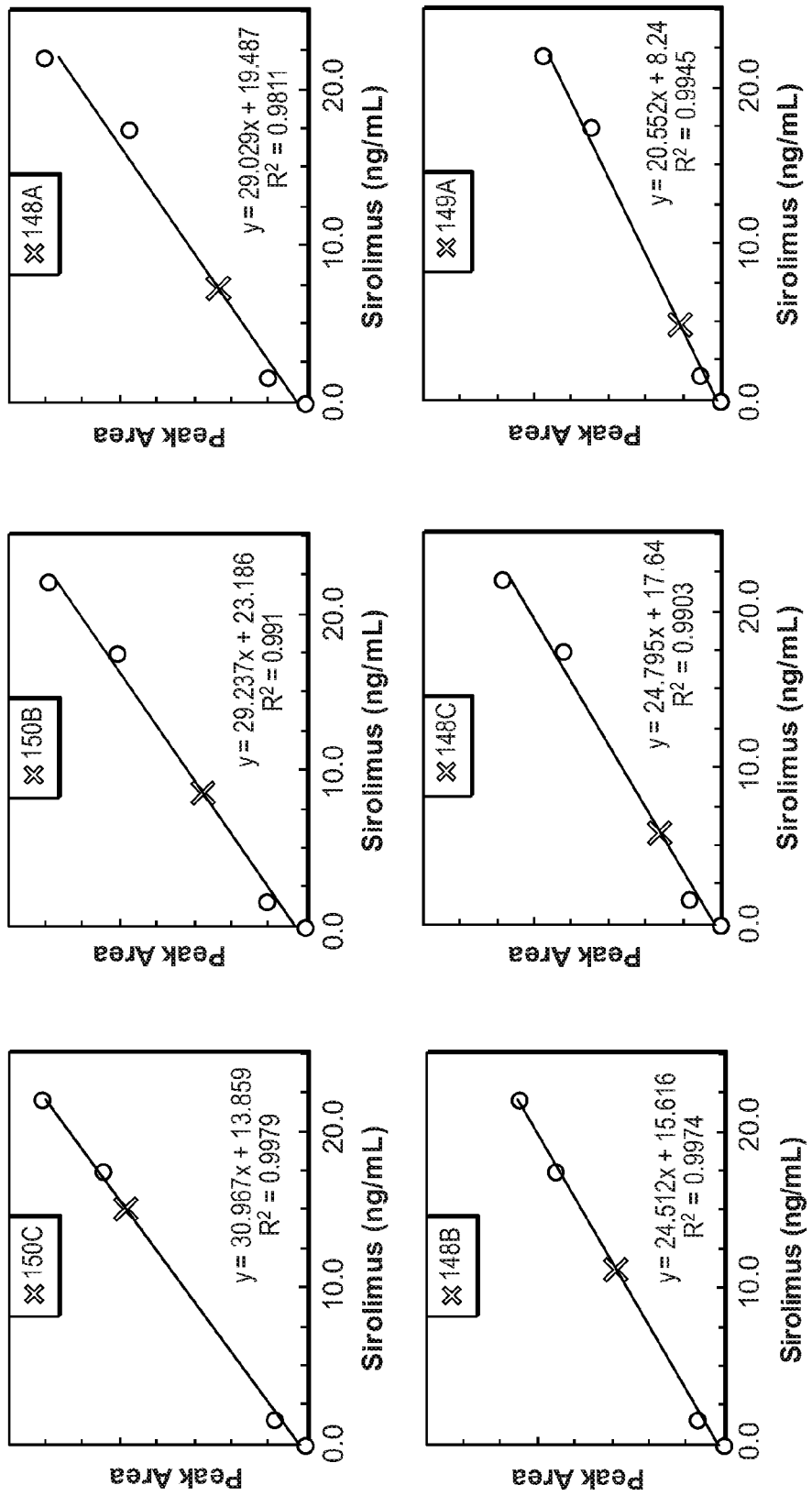
Figure 14B:
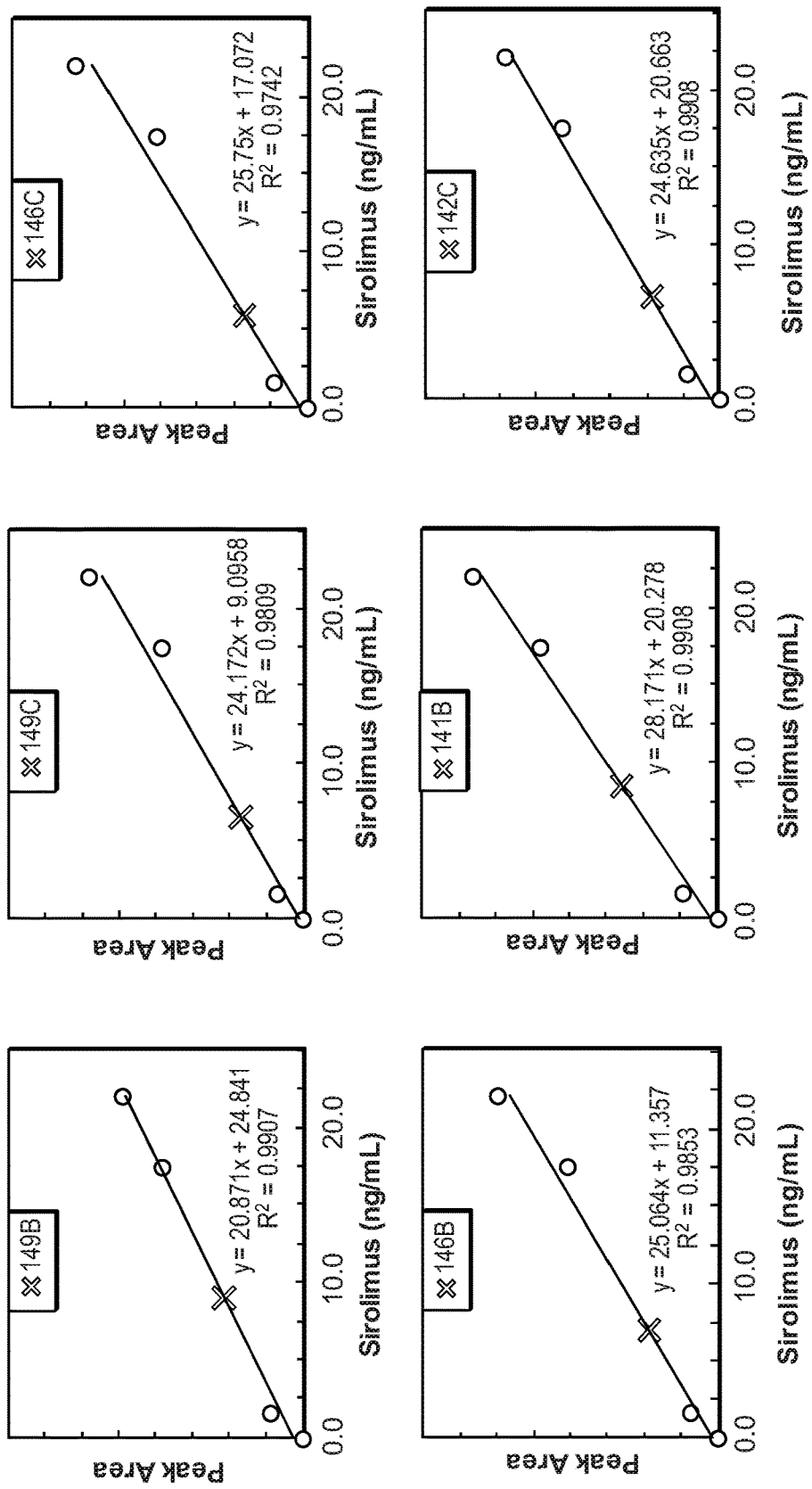
Figure 14C:
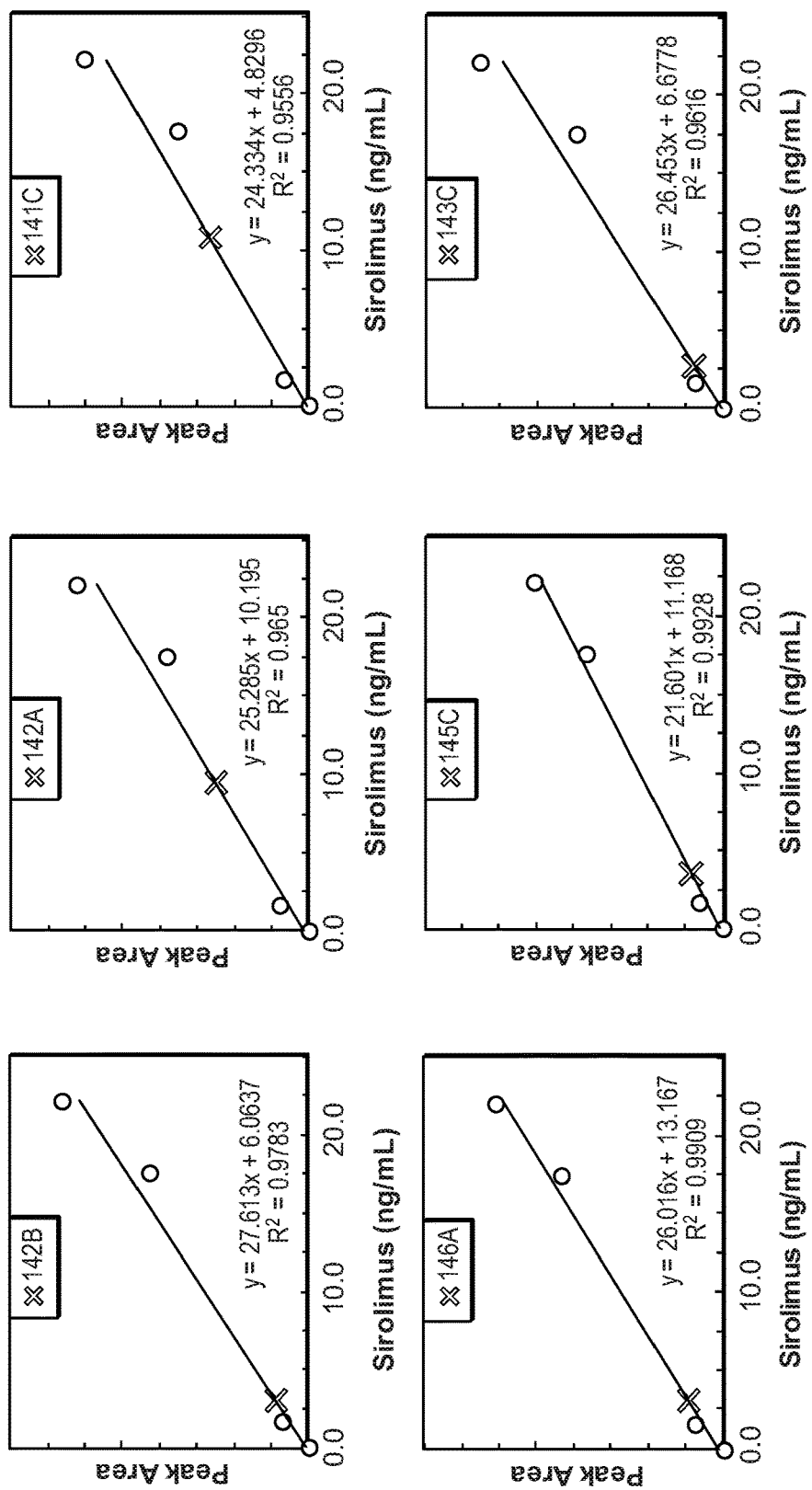
Figure 14D:
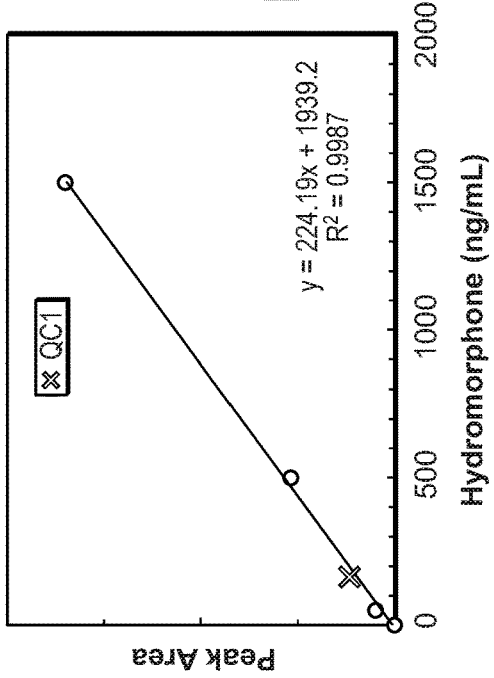

FIG. 13A-B shows individual internal calibration lines for ten IPT samples from Experiment 1 in Example 2. The legend indicates the identity of the IPT sample. The origin was included in the regression calculations.

FIG. 14A-D shows individual internal calibration lines for nineteen IPT samples from Experiment 2 in Example 2. The legend indicates the identity of the IPT sample. The origin was included in the regression calculations.

Figure 15:
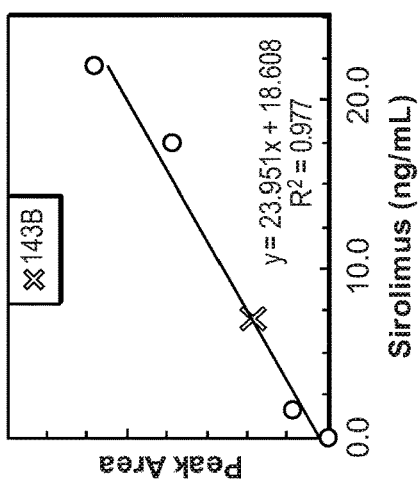

FIG. 15 shows an internal calibration line for the quantification of hydromorphone in urine in Example 3.

Figure 16:
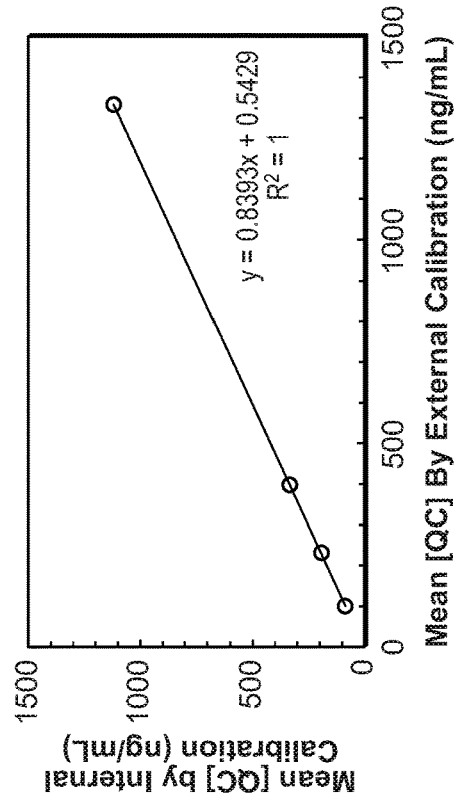

FIG. 16 shows the correlation of the mean hydromorphone concentration values for the 3 QCs and the UTAK QC determined by internal and external calibration in Example 3.

Figure 17A:
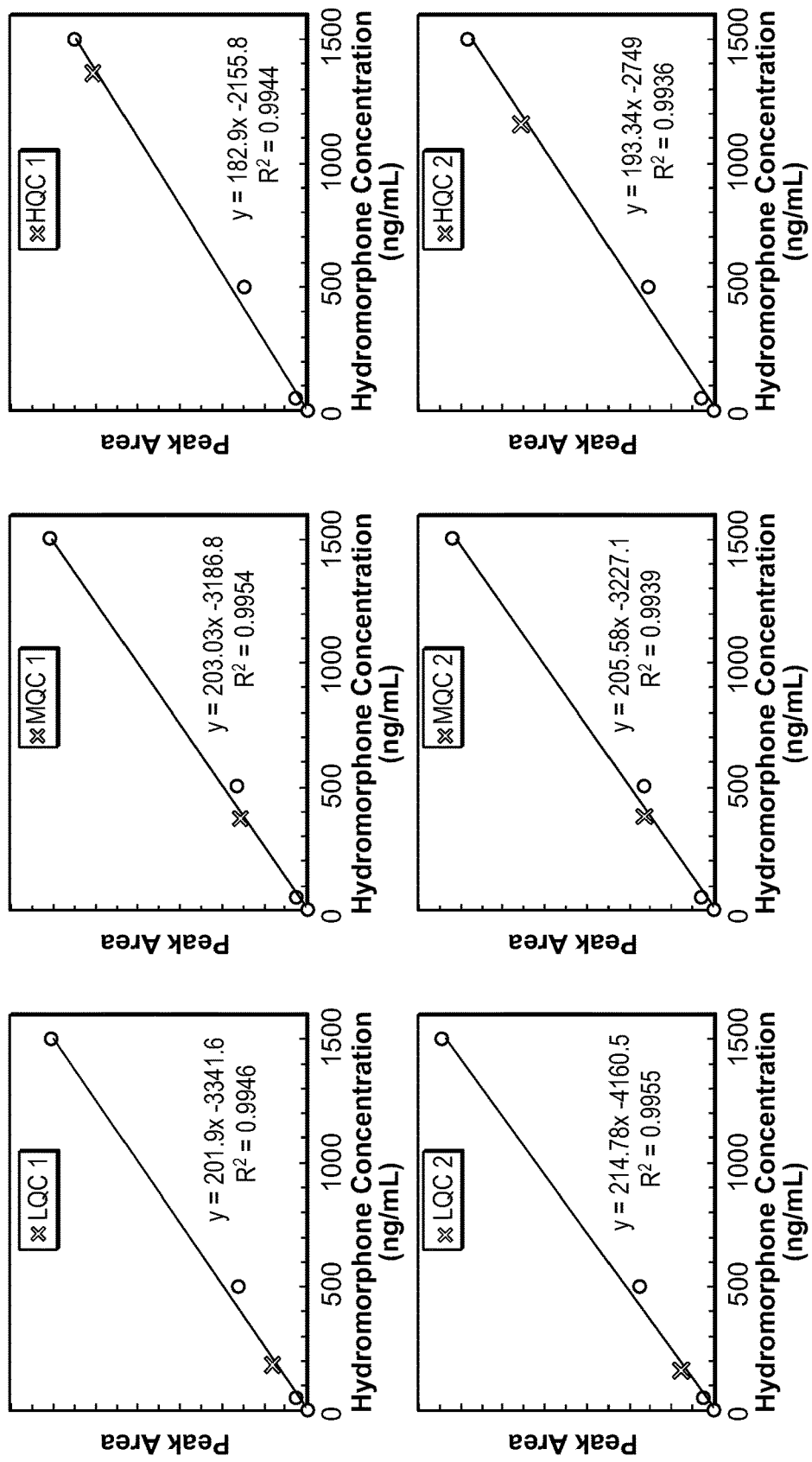
Figure 17B:
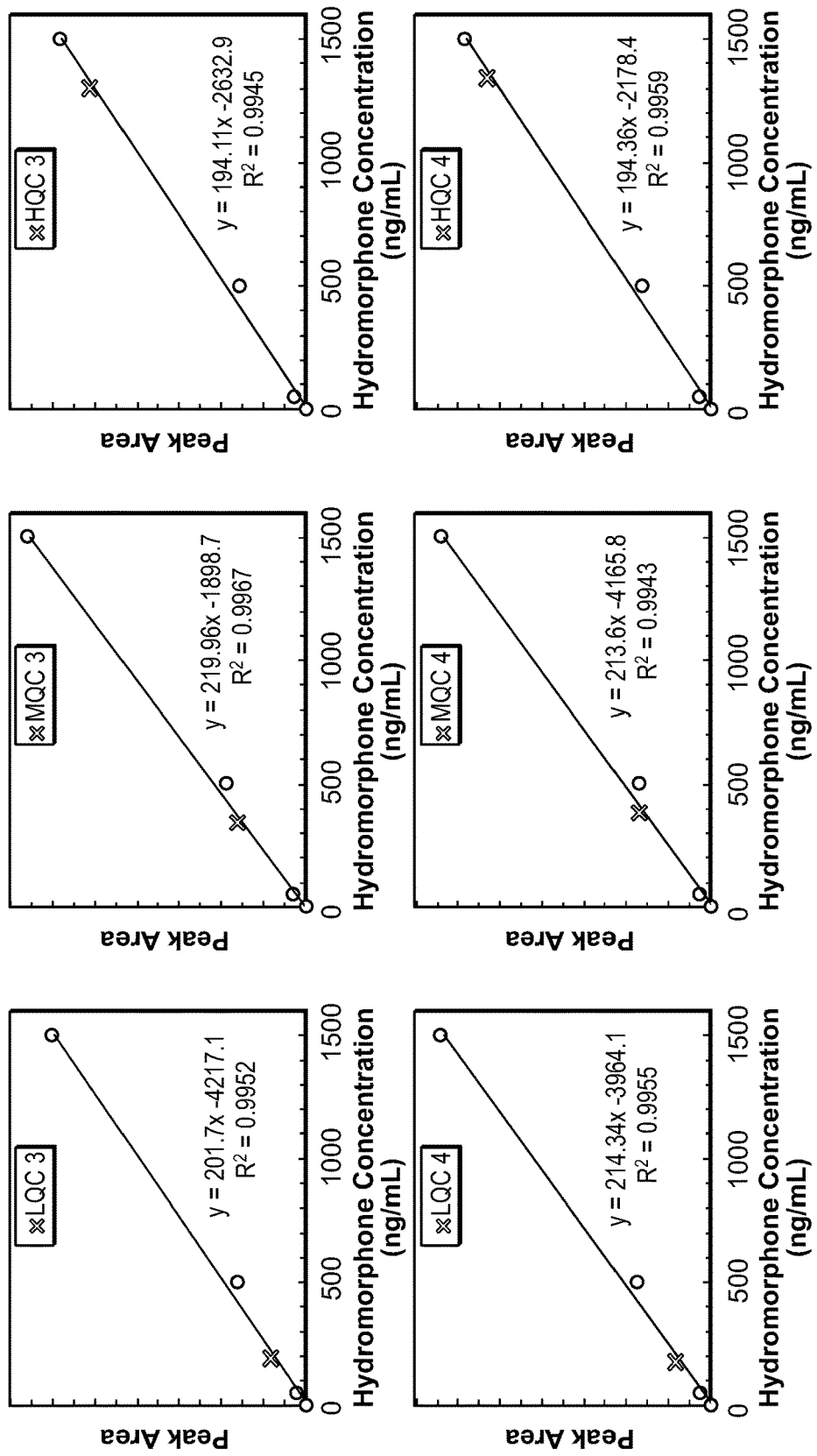

FIG. 17A-C shows individual calibration lines for the internal calibration analysis of the QC replicates in Experiment 2 in Example 3.

Figure 18:
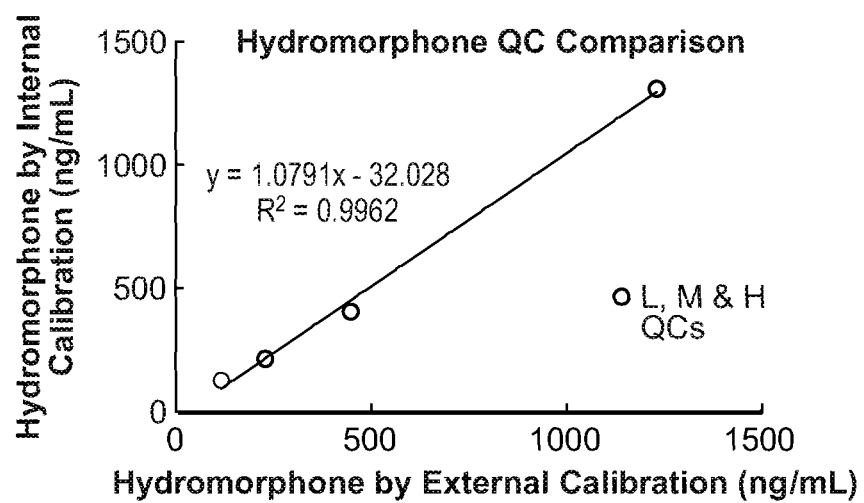

FIG. 18 shows the correlation between hydromorphone concentration values determined by external and internal calibration.

Other features and advantages of the instant invention will be apparent from the following detailed description and claims.

DETAILED DESCRIPTION OF THE INVENTION

The invention provides composition, kits, methods, and apparatuses for quantifying a target analyte in a sample. The invention employs a first known quantity of a first calibrator and a second known quantity of a second calibrator, where the first known quantity and the second known quantity are different, and the first calibrator, the second calibrator, and the target analyte are each distinguishable in the sample by mass spectrometry, to quantify the target analyte in the sample. The first calibrator, the second calibrator, and/or the target analyte can be distinguishable, for example on the basis of isotopic substitution and/or chemical function group substitution. The following detailed description provides additional details on the analytes and calibrators, followed by the composition, kits, methods, and apparatuses and, finally, illustrative examples.

Analytes

Further to the summary above, analytes or target analytes can include essentially any molecule of interest that can be detected in a mass spectrometer. The target analyte can be of interest in one or more of clinical chemistry, medicine, veterinary medicine, forensic chemistry, pharmacology, food industry, safety at work, and environmental pollution. In general, the target analyte is an organic molecule which includes at least 1 carbon atom, such as 1, 2, 3, 4, 5, 6, 7, 8, 9, 10 or more carbon atoms. The target analyte can include up to 1,000, 100, 90, 80, 70, 60, 50, 45, 40, 35, 30, 25, 20, or 15 carbon atoms. Analytes can also include inorganic analytes (e.g., phosphorous compounds, silicon compounds, inorganic polymers, and the like).

Clinical chemistry target analytes can include any organic compound present in an organism (e.g., human body, animal body, fungi, bacterium, virus, and the like). For example, clinical chemistry target analytes include, but are not limited to, nucleoside-bases (e.g., adenine, cytidine, guanine, thymine, uracil), their analogs (e.g., 7-deazaguanine), and derivatives (e.g., mono-, di-, triphosphates or cyclic phosphates); hormones (e.g., steroidal hormones); amino acids; proteins (e.g., brain natriuretic peptide); metabolites (e.g., creatinine, bilirubin); cardiac markers (e.g., creatinkinase-MB); liver markers (e.g., aspartate transaminase); neurotransmitter (e.g., GABA, glycine, biogenic amines (such as dopamine, norepinephrine, epinephrine, histamine, serotonin), acetylcholine, adenosine, anandamide); drugs and their metabolites (e.g., sedatives, tranquilizers, antihypertensives, narcotics).

Human medicine and veterinary medicine target analytes can include any organic compound that can be used for the diagnosis, prophylaxis or treatment of a disease or condition in a subject. For example, human medicine and veterinary medicine target analytes include, but are not limited to, disease markers (e.g., tumor-associated antigens); ultraviolet screening agents, contrast agents; prophylactic or therapeutic agents (e.g., allergens, antibiotics, antifungal agents, antibacterial agents, antihistaminic agents, antineoplastic agents, analgesics, anorexics, anthelmintics, anticonvulsants, antidepressants, antidiabetic agents, antidiarrheals, antihistamines, anti-inflammatory agents, antimigraine preparations, antinauseants, antiparkinsonism drugs, antipruritics, antipsychotics, antipyretics, antispasmodics, anticholinergics, sympathomimetics, xanthine derivatives, cardiovascular effective agents including calcium channel blockers, betablockers, antiarrhythmics, antihypertensives, diuretics, vasodilators; CNS stimulants, agents against cough and cold, decongestants, hormones, hypnotics, immunosuppressives, insect repellents, muscle relaxants, parasympatholytics, parasympathomimetics, psychostimulants, sedatives, tranquilizers, physiologically active peptides and proteins).

Forensic chemistry target analytes can include any organic compound present in a sample taken from the site of crime, such as a sample from a victim's body (e.g., tissue or fluid sample, hair, blood, semen, urine, and the like). For example, clinical chemistry target analytes include, but are not limited to, toxic agents, drugs and their metabolites (e.g., sedatives, tranquilizers, antihypertensives, and narcotics), nucleic acids, DNA, RNA, pesticides, natural products, pollutants, and industrial compounds.

Pharmacology target analytes can include any organic compound that is a pharmaceutical or metabolite thereof or which can be used for the design, synthesis, and monitoring of drugs. For example, pharmacology target analytes include, but are not limited to, prophylactic and/or therapeutic agents, their prodrugs, intermediates and metabolites.

Food industry and agricultural target analytes can include any organic compound that is relevant for monitoring of the safety of foods, beverages, and/or other food industry/agricultural products. Examples of target analytes from the field of food industry include, but are not limited to, steroids, plasticizers, pathogen markers, pesticides, fungicides, pollutants, allergens (e.g. gluten and nut proteins), mycotoxins, marine toxins, and antibiotics (e.g., chloramphenicol in shrimp).

Workplace safety target analytes can include any organic potentially hazardous compound which may be present at a workplace. For example, workplace safety target analytes include, but are not limited to, solvents, low volatile substances, pollutants, carcinogens, toxins, pesticides, fungicides, and any organic substance for which an occupational exposure limit has been set (e.g., by a business, governmental, regulatory, or administrative body).

Environmental pollution (or industrial) target analytes can include any organic compound which can be hazardous for the environment (e.g., organisms in the environment). For example, environmental pollution (or industrial) target analytes include, but are not limited to, persistent organic pollutants (such as aldrin, chlordane, DDT, dieldrin, endrin, heptachlor, hexachlorobenzene, mirex, polychlorinated biphenyls, polychlorinated dibenzo-p-dioxins, polychlorinated dibenzofurans, and toxaphene), polycyclic aromatic hydrocarbons (such as benz[a]anthracene and chrysene), volatile organic compounds, and environmental xenobiotics (such as analgesics, e.g., acetaminophen, acetylsalicylic acid, diclofenac, codeine, ibuprofen; antibiotics, e.g., macrolide antibiotics, sulfonamides, fluoroquinolones, chloramphenicol, tylosin, trimethoprim, erythromycin, lincomycin, sulfamethoxazole, trimethoprim; anticonvulsant, e.g., carbamazepine, primidone; beta-blockers, e.g., metoprolol, propanolol, betaxolol, bisoprolol, nadolol; X-ray media, e.g., iopromide, iopamidol, iohexol, diatrizoate; cytostatics; steroids and hormones, e.g., 17α-ethinylestradiol, mestranol, 19-norethisterone). Analytes can also include inorganic analytes (e.g., phosphorous compounds, silicon compounds, inorganic polymers, and the like). Analytes can also include oils and petrochemicals (e.g., mineral oils and the like).

Target analytes can include amino acids (e.g., Gly, Ala, Val, Leu, Ile, Pro, Phe, Trp, Cys, Met, Ser, Thr, Tyr, His, Lys, Arg, Asp, Glu, Asn, Gln, selenocysteine, ornithine, citrulline, hydroxyproline, methyllysine, carboxyglutamate), peptides, polypeptides, proteins, glycoproteins, lipoproteins; nucleotides, oligonucleotides, polynucleotides, nucleic acids, DNA, RNA, peptide-nucleic acids; sugars, mono-, di-, oligo-, polysaccharides, starches, complex carbohydrates; lipids, fatty acids, fats, complex lipids, steroids; vitamins (A, $B_1$, $B_2$, $B_6$, $B_9$, $B_{12}$, C, D, $D_2$, E, F, K, $K_1$, $K_2$); hormones (such as peptide hormones (e.g., TRH and vasopressin), lipid hormones (e.g., steroid hormones and eicosanoids), monoamines derived from aromatic amino acids (e.g., thyroxine and adrenaline)), androgens (e.g., anabolic steroids, androstenedione, dehydroepiandrosterone, dihydrotestosterone, testosterone), estrogens (e.g., estradiol, estriol, estrone, 17α-ethinylestradiol, mestranol), progestagens (e.g., progesterone, 19-norethisterone), progestins (e.g., norethindrone, norethynodrel, norethindrone acetate, ethynodiol diacetate, levonorgestrel, norethisterone, norgestrel, desogestrel, gestodene, norgestimate, drospirenone, dienogest, drospirenone, nestorone, nomegestrol acetate and trimegestone); steroids, such as insect steroids (e.g., ecdysterone), vertebrate steroids (e.g., sex steroids/hormones, corticosteroids (including glucocorticoids and mineralocorticoids (e.g., hydrocortisone, cortisone, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-butyrate, hydrocortisone-17-valerate, aclometasone dipropionate, flunisolide, beclomethasone dipropionate)), anabolic steroids (e.g., testosterone, nortestosterone, and their derivatives (such as alkylation (e.g., methyl or ethyl) at 17-alpha position, or esterification at the 17-beta position)), cholesterol and derivatives thereof (e.g., oxysterols and bile acids)), plant steroids (such as phytosterols and brassinosteroids (e.g., β-sitosterol, campesterol, stigmasterol, brassicasterol)), fungus steroids (such as ergosterols); industrial polymers (such polyvinylchloride, polyethylene terephthalate, polyacrylamide) and their monomers; small organic molecules such as drugs and drug-like molecules or fragments thereof.

In various embodiments, target analytes of particular interest include steroids (preferably steroid hormones or sex hormones, such as testosterone, cortisol, estrone, estradiol, 17-OH-progesterone or aldosterone); immunosuppressant drugs (such as cyclosporin A, tacrolimus, sirolimus, everolimus, or mycophenolic acid); thyroid markers (such as thyroid-stimulating hormone (TSH), thyroglobulin, triiodothyronine (T3), free T3, thyroxine (T4), free T4, or ferritin); vitamins or metabolites thereof (such as the 25-hydroxy-, 1,25-dihydroxy- or 24, 25-dihydroxy-form of vitamin D2 or vitamin D3); cardiac markers (such as troponins or brain natriuretic peptide); alpha-fetoprotein; applipoprotein, or drugs of abuse (such as hydromorphone, other opiod drugs, or therapeutic drugs).

Samples

In general, a sample is a composition including at least one target analyte (e.g., an analyte of the class or kind disclosed above, together with a matrix). Samples can include a solid, liquid, gas, mixture, material (e.g., of intermediary consistency, such as a, extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of an individual. In this context, the individual can be an animal, for example a mammal, for example a human. Other example individuals include a mouse, rat, guinea-pig, rabbit, cat, dog, goat, sheep, pig, cow, or horse. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumor cells). Such bodily samples can be obtained by known methods including tissue biopsy (e.g., punch biopsy) and by taking blood, bronchial aspirate, sputum, urine, feces, or other body fluids. Exemplary bodily samples include humor, whole blood, plasma, serum, umbilical cord blood (in particular, blood obtained by percutaneous umbilical cord blood sampling (PUBS), cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract.

Environmental samples can include any sample that is derived from the environment, such as the natural environment (e.g., seas, soils, air, and flora) or the manmade environment (e.g., canals, tunnels, buildings). Such environmental samples can be used to discover, monitor, study, control, mitigate, and avoid environmental pollution. Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Food samples can include any sample that is derived from food (including beverages). Such food samples can be used for various purposes including, for example, (1) to check whether a food is safe; (2) to check whether a food contained harmful contaminants at the time the food was eaten (retained samples) or whether a food does not contain harmful contaminants; (3) to check whether a food contains only permitted additives (e.g., regulatory compliance); (4) to check whether it contains the correct levels of mandatory ingredients (e.g., whether the declarations on the label of the food are correct); or (5) to analyze the amounts of nutrients contained in the food. Exemplary food samples include edible products of animal, vegetable or synthetic origin (e.g., milk, bread, eggs, or meat), meals, drinks, and parts thereof, such as retain samples. Food samples can also include fruits, vegetables, pulses, nuts, oil seeds, oil fruits, cereals, tea, coffee, herbal infusions, cocoa, hops, herbs, spices, sugar plants, meat, fat, kidney, liver, offal, milk, eggs, honey, fish, and beverages.

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

Calibrators

Further to the summary above, calibrators or internal calibrators are compounds which, are similar to a corresponding target analyte with respect to chemical composition (e.g., empirical formula), structure (e.g., atomic arrangement and bonding), and/or physicochemical properties, but which is distinguishable by the behavior of the internal calibrator and target analyte in a mass spectrometer. The calibrator and analyte can have at least the same base structure in common (e.g., a characteristic mono- or polycyclic ring structure, such as sterane). In many embodiments, the compounds differ only slightly with respect to their chemical composition and/or molecular mass. For example, difference in composition and/or mass can result from (i) replacement of one group with a homologous group (e.g., a homologous group can have 1 carbon atom more or less (e.g., ethyl (ethylene) can be considered a homologue to methyl and propyl (methylene and propylene)); (ii) modification of a functional group (e.g., acetylation of an amino group; esterification; methylation; hydroxylation; hydration; biotinylation; cleavage of an amide, ester, thioester, acetal, ketal group; decarboxylation; demethylation; dehydration); (iii) replacement of an atom with another atom of the same group of the period table of elements (e.g., replacement of one halogen with another); and (iv) replacement of an atom with a corresponding isotope of said atom (e.g., $^1H$ is replaced with $^2H$).

Furthermore, an internal calibrator can mimic a corresponding target analyte such that at least one of the physicochemical properties of the internal calibrator is essentially identical to the corresponding physicochemical property of the target analyte. Physicochemical properties can include any measurable property the value of which describes a physical and/or chemical state of a compound. For example, physicochemical properties include, but are not limited to, size, mass, absorbance, emission, electric charge, electric potential, isoelectric point (pI), flow rate (e.g., retention time), magnetic field, spin, solubility, viscosity, reactivity against or affinity to other substances (e.g., antibodies, enzymes), toxicity, chemical stability in a given environment, capability to undergo a certain set of transformations (e.g., molecular dissociation, chemical combination, redox reactions) under certain physical conditions in the presence of another chemical substance, polarity, and hydrophobicity/hydrophilicity.

In various embodiments, the internal calibrator and its corresponding target analyte are effectively indistinguishable from each other by one or more techniques commonly used to process a sample prior to mass spectrometric analysis. For example, an internal calibrator and its corresponding target analyte can be indistinguishable on the basis of solubility (in a solvent, e.g., water or an organic solvent, or a mixture of solvents), retention time (in a separation technique, such as liquid chromatography), affinity (e.g., to an antibody specific for said target analyte), dissociation constant, reactivity and/or specificity towards an enzyme (e.g., hydrolase, transferase).

The internal calibrator is generally absent or in a negligible (or otherwise compensable) initial amount in the sample to be analyzed. The internal calibrator can be a synthetic compound, e.g., a compound which does not naturally occur (e.g., in the sample) or the natural abundance of which is below the detection limit of a mass spectrometer. For example, an internal calibrator can be an isotope-labeled analog of the corresponding target analyte, a derivative of the corresponding target analyte, or a metabolite of the corresponding target analyte.

Isotopes relate to nuclides with the same number of protons but differing numbers of neutrons (i.e., they have the same atomic number and are therefore the same chemical element). Different isotopes of the same chemical element generally have essentially the same chemical characteristics and therefore behave essentially identically in chemical and/or biological systems. Therefore, isotope labeled analogs of a corresponding target analytes include compounds that are essentially identical to the target analyte in chemical composition and structure, with the exception that at least one atom of the target analyte is substituted for an isotope thereof.

In various embodiments, the at least one atom of the target analyte is the most abundant naturally occurring isotope and the substituted isotope of the calibrator is a less abundant isotope. For example, the target analyte can include a position with $^1H$ ($^{12}C$, $^{14}N$, $^{16}O$, or $^{80}Se$) and the calibrator can substitute the atom in that position for $^2H$ ($^{13}C$, $^{15}N$, $^{17}O$, $^{18}O$, $^{33}S$, $^{36}S$, and $^{74}Se$, respectively). The natural abundance of the isotope can be less than 49% (e.g., less than 40%, 30%, 20%, 10%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the total amount of all existing isotopes). The isotope labeled analog can use a stable isotope.

A stable isotope of an atom can be non-radioactive or radioactive. If the stable isotope is radioactive, its half-life is too long to be measured, such as a half-life longer than the age of the universe, e.g., a half-life of $13.75 \times 10^9$ years or greater. Stable isotopes include, but are not limited to, $^2H$, $^6Li$, $^{11}B$, $^{13}C$, $^{15}N$, $^{17}O$, $^{18}O$, $^{25}Mg$, $^{26}Mg$, $^{29}Si$, $^{30}Si$, $^{33}S$, $^{34}S$, $^{36}S$, $^{37}Cl$, $^{41}K$, $^{42}Ca$, $^{43}Ca$, $^{44}Ca$, $^{46}Ca$, $^{48}Ca$, $^{46}Ti$, $^{47}Ti$, $^{49}Ti$, $^{50}Ti$, $^{50}V$, $^{50}Cr$, $^{53}Cr$, $^{54}Cr$, $^{54}Fe$, $^{57}Fe$, $^{58}Fe$, $^{60}Ni$, $^{61}Ni$, $^{62}Ni$, $^{64}Ni$, $^{65}Cu$, $^{66}Zn$, $^{67}Zn$, $^{68}Zn$, $^{70}Zn$, $^{71}Ga$, $^{73}Ge$, $^{76}Ge$, $^{74}Se$, $^{76}Se$, $^{77}Se$, $^{78}Se$, $^{82}Se$, $^{81}Br$, $^{84}Sr$, $^{96}Zr$, $^{94}Mo$, $^{97}Mo$, $^{100}Mo$, $^{98}Ru$, $^{102}Pd$, $^{106}Cd$, $^{108}Cd$, $^{113}In$, $^{112}Sn$, $^{112}Sn$, $^{114}Sn$, $^{115}Sn$, $^{120}Te$, $^{123}Te$, $^{130}Ba$, $^{132}Ba$, $^{138}La$, $^{136}Ce$, $^{138}Sn$, $^{148}Nd$, $^{150}Nd$, $^{144}Sm$, $^{152}Gd$, $^{154}Gd$, $^{156}Dy$, $^{158}Dy$, $^{162}Er$, $^{164}Er$, $^{168}Yb$, $^{170}Yb$, $^{176}Lu$, $^{174}Hf$, $^{180m1}Ta$, $^{180}W$, $^{184}Os$, $^{187}Os$, $^{190}Pt$, $^{192}Pt$, $^{196}Hg$, and $^{204}Pb$. Examples of preferred stable isotopes include $^2H$, $^{11}B$, $^{13}C$, $^{15}N$, $^{17}O$, $^{18}O$, $^{33}S$, $^{34}S$, $^{36}S$, $^{74}Se$, $^{76}Se$, $^{77}Se$, $^{78}Se$, and $^{82}Se$.

An isotope labeled analog can substitute between one and n atoms with isotopes, where n is the number of atoms in the target analyte molecule. In various embodiments, isotope labeled analogs can include 1, 2, 3, . . . n substitutions, which can then form a set of internal calibrators. For example, a first calibrator can be an analog with one substitution, a second calibrator can be an analog with two substitutions, a third calibrator can be an analog with three substitutions, and so on. The isotope labeled analogs can vary by one or more (e.g., where more than one substitution is made between analogs and/or where the isotopes differ by more than one mass unit from the most common naturally occurring isotope) mass units. A given analog can be isotopically pure with respect to the atom in the substituted position(s).

Isotopically pure can mean that at least 95% of atoms of a given type (e.g., a high abundant isotope such as $^1H$) contained in a compound (such as a target analyte) have been replaced with another, preferably less abundant, isotope of the same element (e.g., $^2H$). For example, at least 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, or 99.99% or more of atoms of a given type can be replaced with another, preferably less abundant, isotope of the same element.

Derivatives of target analytes include compounds that are similar to the target analyte in chemical composition, except that they are derivatized. Derivatizing or derivatization relates to the transformation of a chemical compound (starting material) into a product, i.e., a derivative, having a similar structure to the starting material. A derivative can exhibit one or more altered (e.g., relative to the starting material) physicochemical properties, such as altered reactivity, solubility, boiling point, melting point, aggregate state, or chemical composition. Altered physicochemical properties can be used for quantification and/or separation of the derivative and/or starting material. Example of derivatization include reduction (with or without an enzyme), oxidation (with or without an enzyme), acylation (e.g., acetylation), alkylation (e.g., methylation), hydrolysis (e.g., of ester, amide, epoxide groups), addition (e.g., hydrogenation of double or triple bonds), condensation (e.g., generating an imine bond), elimination (e.g., reductive elimination or elimination of water), and substitution (e.g., nucleophilic or electrophilic substitution).

Metabolites include intermediates and products of metabolism, for example the transformation, degradation, and elimination of organic compound by natural (or engineered) biochemical process. Metabolites can be small molecules, e.g., having a molecular mass of below 1500 Da. Metabolites can be, or originate from, endogenous or exogenous (e.g., pharmaceutical) compounds.

The property of being distinguishable based upon behavior in a mass spectrometer includes situations where two or more compounds (such as the first and second internal calibrators; the first or second internal calibrator and the target analyte; or the first internal calibrator, second internal calibrator, and the target analyte) can be distinguished from each other by a mass spectrometer due to differences in their mass (i.e., a difference in mass that can be resolved by a MS instrument, or at a given cutoff) and/or fragmentation pattern.

For example, two compounds (e.g., the first internal calibrator and the target analyte) can be distinguished from each other by a mass spectrometer due to differences in their mass. The masses of the two compounds (e.g., the first internal calibrator and the target analyte) can differ in at least 1 (or 2, 3, 4, 5, . . . ) mass units where the compounds are isotopic analogs. A difference in mass can be less than one mass unit, or a non-integer mass unit greater than one. Depending upon instrument resolution and/or a desired resolution cutoff, a difference in mass can be a difference of ±0.1, 0.01, 0.001, 0.0001, 0.0001 mass units. The difference in mass between these two compounds can originate from the presence of different isotopes (e.g., low abundant isotopes in one of the two compounds vs. high abundant isotopes in the other of the two compounds) and/or different chemical moieties.

Any two compounds (e.g., the first internal calibrator and the target analyte) can also be distinguished from each other by a mass spectrometer due to differences in their fragmentation pattern. The fragmentation pattern of a compound relates to the compound-specific set of fragments (e.g., product/daughter ions) generated in a mass spectrometer from the compound. The two or more compounds (e.g., a calibrator and corresponding target analyte, two calibrators) can fragment during the MS analysis essentially in the same way, thereby generating fragments similar in chemical composition and structure. However, the fragment generated from one compound (e.g., the calibrator) can differ from the corresponding structurally similar fragment generated by the other compound (e.g., the corresponding target analyte) by a difference in mass that is resolvable by the instrument being used (or by a predetermined cutoff).

Many molecules that can be used as internal calibrators are commercially available or can be prepared using known organic synthetic chemistry methods. Internal calibrators can be selected, for example, according to the following general scheme (a) subjecting a given target analyte to fragmentation in a mass spectrometer in order to obtain its fragmentation pattern; (b) selecting a specific fragment of said fragmentation pattern; (c) designing an isotopically labeled fragment on the basis of the fragment selected in step (b) which differs from the fragment selected in step (b) by a resolvable difference in mass and which is distinguishable from the other fragments and ions of the fragmentation pattern obtained in step (a); (d) designing an isotopically-labeled internal calibrator which will produce said isotopically labeled fragment designed in step (c) in a mass spectrometer; and (e) preparing said isotopically-labeled internal calibrator.

Figure 1:
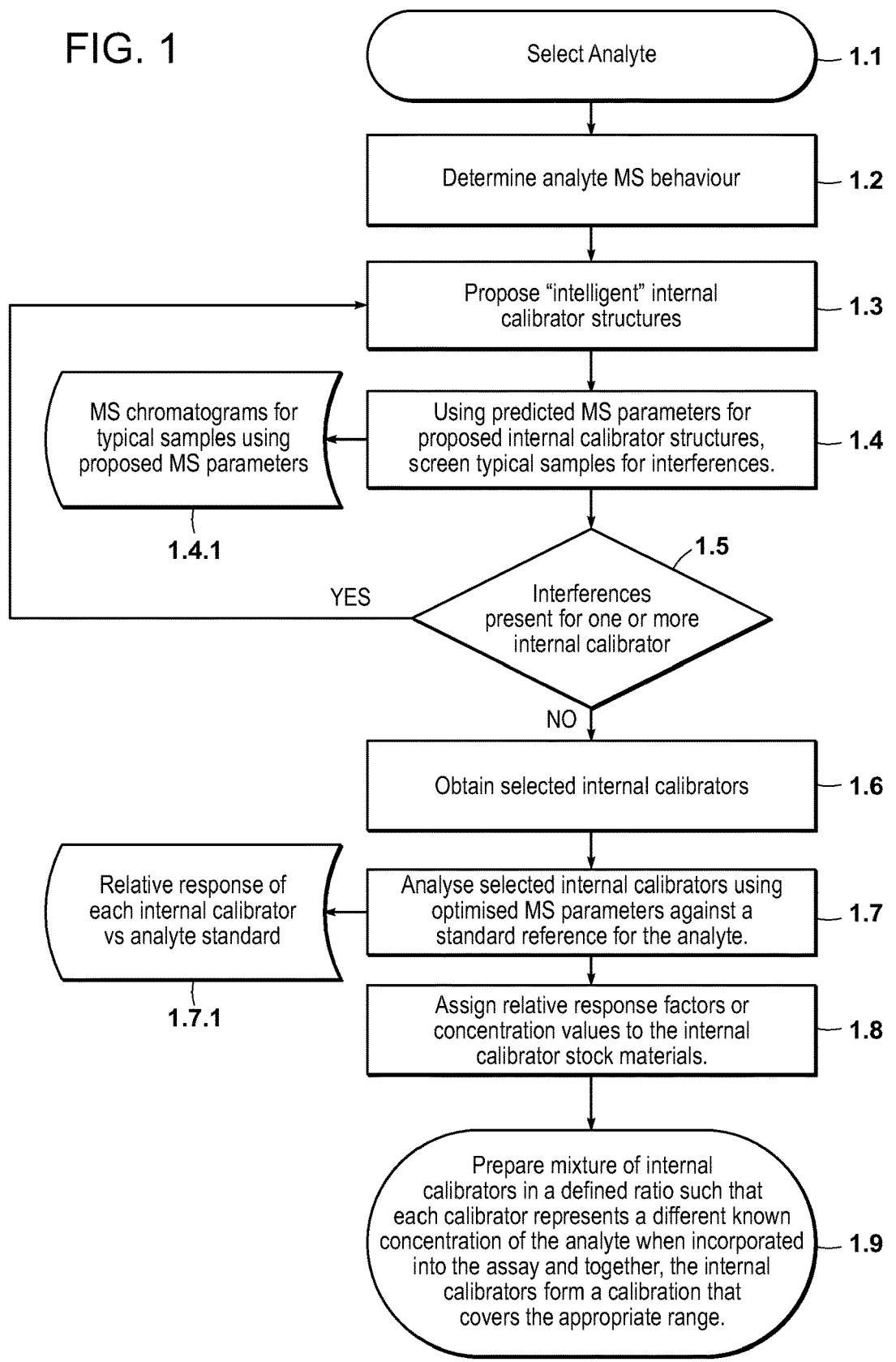

FIG. 1 presents a flow chart outlining another example method for selecting internal calibrators for an MS-based assay in accordance with the invention.

FIG. 1, step 1.1 includes selecting an analyte. Analytes can be selected based upon the user's needs and/or from the categories and listings of analytes described herein.

FIG. 1, step 1.2 includes determining the selected analyte's MS behavior. For example, the MS behavior can be determined by analyzing the selected analyte using the MS method chosen for the final assay (e.g., MS, MS/MS, high resolution, etc.), to ascertain one or more properties such as analyte mass, ionization characteristics, fragmentation characteristics, and the like.

FIG. 1, step 1.3 incorporates information from FIG. 1, step 1.2 to propose one or more internal calibrator structures. For example, where the internal calibrators are stable isotope labeled analogs, appropriate labeling positions can be identified to provide sufficient additional mass in the precursor ion and product ion (if appropriate), such that the analyte and all internal calibrators are distinguishable from each other and their responses independently measurable by MS.

FIG. 1, step 1.4 includes screening typical samples for interferences, using the predicted MS parameters for the proposed internal calibrators. For example, this step can include FIG. 1, sub-step 1.4.1 of analyzing typical samples (e.g., processed plasma, urine, drinking water) using the proposed MS parameters for the proposed internal calibrators (e.g., using LC coupled with a tandem quadrupole MS in MRM mode) to monitor the specific precursor>product transitions proposed for the internal calibrators. This analysis can identify the interferences expected in typical samples, which might also interfere in the assay. Thus, if interferences are expected in the final assay, the proposed internal calibrators can be re-designed before they are purchased or synthesized, thereby minimizing the time and cost for developing an assay, and maximizing the chance of developing a robust, successful assay.

FIG. 1, step 1.5 includes determining if interferences are present for one or more internal calibrator. If interference occurs, then the party developing the assay should return to FIG. 1, step 1.3, to propose new internal calibrator structures that are expected to avoid interference. If no material interference occurs (or if the interference can be compensated for), then the party developing the assay can proceed to the next step.

FIG. 1, step 1.6 includes obtaining the internal calibrators selected in FIG. 1, step 1.5. Selected internal calibrators can be obtained from commercial sources or by custom synthesis. For stable isotope labeled internal calibrators, synthesis can provide appropriate isotopic labels in the appropriate parts of the molecule(s). For analog internal calibrators, synthesis can provide modified amino acid sequences for example for the analysis of peptide or protein analytes. Synthesis can provide one or more desired properties permitting the analyte and internal calibrators to be distinguished from each other and their responses independently measured using mass spectrometry.

FIG. 1, step 1.7 includes analyzing the selected internal calibrators using optimized MS parameters against a standard reference for the analyte. For example, this step can include FIG. 1, sub-step 1.7.1 of determining the relative response of each internal calibrator vs. an analyte standard.

FIG. 1, step 1.8 includes assigning relative response factors or concentration values to the internal calibrator stock materials. Internal calibrators can have slightly different ionization efficiency or fragmentation efficiency compared to the parent analyte due to substitution of atoms with stable isotope labels (e.g., $^1H$ substituted by $^2H$), or in the case of analog internal calibrators, substitution of amino acids; substitution of functional groups, and the like. Or, in the case where only a small quantity of internal calibrator is available, it might not be possible to prepare a solution with an accurately known concentration. It is therefore necessary, under certain circumstances, to measure the MS response of the internal calibrator against the response of a known concentration of the analyte of interest. In some embodiments, the known concentration will be traceable to a reference standard, for example, from NIST. The measurements can be used to calculate a relative response factor and/or assign an apparent analyte concentration value to the internal calibrator solution. For example, for an internal calibrator that has a relative response of 90%, it can be advantageous, under certain circumstances, to either correct the analyte concentration determined in a sample by dividing the result 0.9 or assign a concentration value to the internal calibrator that is 0.9× the true concentration of the internal calibrator.

FIG. 1, step 1.9 includes preparing a mixture of internal calibrators in a defined ratio such that each calibrator represents a different known concentration of the analyte when incorporated into the assay and together, the internal calibrators form a calibration that covers the appropriate range. The internal standard mixture can be incorporated into the assay by various methods, for example: manual addition of a calibrator solution during sample preparation; addition of a defined volume of sample to a tube or other container that is pre-loaded with internal calibrators; automated addition of internal calibrator solution to the sample by a sample preparation device that may be coupled directly or indirectly (e.g., via a chromatography device) to the mass spectrometer or may be part of an integrated analyzer. It is also possible to add multiple sets of internal calibrators to a single sample by any of the above means such that a single assay could generate results for multiple analytes. Further description and examples of calibrator compositions are discussed in the summary above and the composition section below.

Table 1 lists the results of applying the method discussed in connection with FIG. 1 to develop stable isotope labeled and/or analog internal calibrators for the quantification of various analytes in five different application areas.

corresponding to the target analyte (e.g., to increase precision and/or accuracy, to decrease signal noise and/or interference or to expand the measurement range). Accordingly, a set of internal calibrators can include 2, 3, 4, 5, 6, 7, 8, 9, 10, and up to an arbitrary number of internal calibrators for a target analyte (e.g., a theoretical maximum can be determined by the maximum number of calibrators that can be

TABLE 1 results of applying the method discussed in connection with FIG. 1.

| | Analyte | Analyte Type | Matrix | Proposed Internal Calibrators | Application Area |
|---|---|---|---|---|---|
| 1 | Testosterone | Endogenous Steroid | Human plasma/serum | Stable Isotope:<br>testosterone-d2<br>testosterone-d3<br>testosterone-d5 | Clinical Chemistry |
| 2 | Hydromorphone | Opiod drug Therapeutic and abused | Human urine | Mixed: Stable Isotope & Stable Isotope analog.<br>oxymorphone-d3<br>hydromorphone-d4<br>hydromorphone-d6 | Toxicology |
| 3a | Apolipoprotein A | Endogenous Protein | Human serum | Stable Isotope Peptides (see Note 1):<br>APOA1: H2N-DYVSQFEGSALGK^-OH<br>APOA1: H2N-DYVSQFEGSALGK^^-OH<br>APOA1: H2N-DYVSQFEGSALGK^^^-OH | Biomarker Quantification |
| 3b | Apolipoprotein B | Endogenous Protein | Human serum | Stable Isotope Peptides (see Note 1):<br>APOB100: H2N-TSSFALNLPTLPEVK^-OH<br>APOB100: H2N-TSSFALNLPTLPEVK^^-OH<br>APOB100: H2N-TSSFALNLPTLPEVK^^^-OH | Biomarker Quantification |
| 4 | Sirolimus | Immuno-suppressive Drug | Human whole blood | Mixed:<br>32-desmethoxyrapamycin (analog)<br>everolimus (analog)<br>everolimus-d6 (SIL analog) | Therapeutic Drug Monitoring |
| 5 | Testosterone | Contaminant | Drinking water | Stable Isotope:<br>testosterone-d2<br>testosterone-d3<br>testosterone-d5 | Environmental Monitoring |

Note 1:
The different stable isotope labelled peptides (indicated by the symbols ^^^, ^^ and ^) will contain $^{15}N_2$ or $^{13}C_6$ or $^{13}C_6, ^{15}N_2$, respectively, providing mass increases relative to the mass of the native peptides of 1.994070 Da, 6.020129 Da or 8.014199 Da.

These two example methods for selecting internal calibrators are illustrative. A person of ordinary skill in the art would understand that individual steps can be added, omitted, and/or repeated and that further alternative methods are possible.

Compositions and Kits

Further to the summary above, composition according to the invention can include a first known quantity of a first calibrator and a second known quantity of a second calibrator, wherein the first known quantity and the second known quantity are different, and wherein the first calibrator, the second calibrator, and the target analyte are each distinguishable in the single sample by mass spectrometry. Kits according to the invention can include any one or more of the inventive compositions, together with instructions (and/or other/additional means) for implementing the methods and/or employing the apparatuses of the invention.

In order to quantify a target analyte, the compositions require at least two internal calibrators corresponding to the target analyte. However, in certain circumstances, it can be advantageous to include more than two internal calibrators designed and used for a given target analyte, for example, the number of positions that can be substituted for a stable isotope and will produce a usable signal in the contexts of the target analyte, other internal calibrators, and sample matrix). Each internal calibrator in the set should be distinguishable from each other and the target analyte by MS.

In order to quantify a target analyte, the compositions also require that at least two of the internal calibrators are present in different amounts/concentrations. In various embodiments, the amount of each internal calibrator is different. However, certain embodiments can include two or more of the internal calibrators in essentially the same amount/concentration (e.g., as long as at least two of the internal calibrators are present in different amounts/concentrations). For example, an amount of a third internal calibrator does not have to be different from the first amount of the first internal calibrator and the second amount of the second internal calibrator (e.g., the amount of the third internal calibrator can be identical to the first amount of the first internal calibrator or the second amount of the second internal calibrator).

The amounts of the two or more internal calibrators can be selected to facilitate quantification of the target analyte. For example, the amounts of the internal calibrators can be selected to provide accuracy and precision over a specific analytical range of an analyte (e.g., where a specific target analyte is known to vary within a predetermined window.) In another example, the amounts of the internal calibrators can be selected to provide maximum flexibility over the analytical range of the instrument (e.g., where a target analyte is expected to vary widely or multiple analytes having different properties are to be analyzed).

In various embodiments, the two or more internal calibrators span a portion or essentially the entire analytical range of the target analyte in the sample to be analyzed. The analytical range can describe the range over which meaningful data can be collected (e.g., within pre-determined statistical parameters). The analytical range can be defined by the detection limit of an internal calibrator or target analyte in a mass spectrometer and/or the expected amount(s) of target analyte in the sample.

Thus, the amount of one or more internal calibrators can be around the expected amount of the target analyte in the sample (e.g., . . . , 50%, . . . , 95%, 96%, 97%, 98%, 99%, 100%, 101%, 102%, 103%, 104%, 105%, . . . , 150%, . . . of the expected amount of the target analyte in the sample). If the amount of the target analyte in the sample is expected to vary by orders of magnitude, then the amount of one or more internal calibrators can be, for example, . . . , 1%, . . . , 10%, . . . , 100%, . . . , 1000%, . . . , 10,000% of the expected amount of the target analyte in the sample.

The amount of one or more internal calibrators can be around/above the lower end of the analytical range of the internal calibrator in the instrument (e.g., . . . , 95%, 96%, 97%, 98%, 99%, 100%, 101%, 102%, 103%, 104%, 105%, . . . , 1000%, . . . , 10,000% of the lower end of the analytical range of the internal calibrator in the instrument). Similarly, the amount of one or more internal calibrators can be around/below the upper end of the analytical range of the internal calibrator in the instrument (e.g., 0.1%, . . . , 1%, . . . , 95%, 96%, 97%, 98%, 99%, 100%, 101%, 102%, 103%, 104%, 105%, . . . of the upper end of the analytical range of the internal calibrator in the instrument).

The relative amounts of any two internal calibrators (e.g., the internal calibrators present in the highest and lowest amounts) can be defined by a ratio, for example: 1.1, 1.15, 1.20, 1.25, 1.3, 1.4, 1.5, 2, 2.5, 3, 3.5, 4, 4.5, 5, 6, 7, 8, 9, 10, 11, 12, 13, 14, 15, 20, 25, 30, 35, 40, 45, 50, 55, 60, 65, 70, 75, 80, 90, 100, 150, 200, 250, 300, 350, 400, 450, 500, 600, 700, 800, 900, 1,000, 10,000, 100,000, 1,000,000, or more. In the embodiments including three or more internal calibrators, the differences between the amounts of internal calibrators can be linear (e.g., 2×, 3×, 4×, . . . ), exponential (e.g., $10^1 \times$, $10^2 \times$, $10^3 \times$, . . . ), random, or a combination or variation thereof.

The invention also encompasses compositions for quantifying more than one target analyte in a single sample. For example, a composition for quantifying a target analyte and an additional target analyte (i.e., two total analytes in a single sample) can include (i) a first known quantity of a first calibrator and a second known quantity of a second calibrator, where the first known quantity and the second known quantity are different and (ii) a third known quantity of a third calibrator and a fourth known quantity of a fourth calibrator, where the third known quantity and the fourth known quantity are different, and where the first calibrator, the second calibrator, the third calibrator, the fourth calibrator, the target analyte, and the additional target analyte are each distinguishable in the single sample by mass spectrometry. If the composition was adapted to quantify a second additional target (i.e., three total analytes in a single sample), it could further include a fifth known quantity of a fifth calibrator and a sixth known quantity of a sixth calibrator, where the fifth known quantity and the sixth known quantity are different, and where the first calibrator, the second calibrator, the third calibrator, the fourth calibrator, the fifth calibrator, the sixth calibrator, the target analyte, the additional target analyte, and the second additional target analyte are each distinguishable in the single sample by mass spectrometry.

Further compositions for quantifying multiple analytes (e.g., 2, 3, 4, 5, 6, 7, 8, 9, . . . total analytes) can be produced, for example, by combining two or more internal calibrators for each target analyte potentially present in the single sample. In some cases, e.g. where multiple analytes having similar properties are to be measured, one or more of the multiple calibrators can be used to quantify multiple different analytes (e.g., in a opioid panel). As described above, the two internal calibrators for each target analyte should be present in different amounts. Furthermore, in various embodiments, the target analytes and internal calibrators should all be distinguishable in the single sample by mass spectrometry. Different target analytes can each, independently, have different numbers of corresponding internal calibrators. Different internal calibrators can consist essentially of different stable isotope analogs, analogs, derivatives, metabolites, related compounds of the target analyte, or combinations thereof.

In certain embodiments, not all of the internal calibrators are strictly required to be distinguishable from each other and from all corresponding target analytes on the basis of their the behavior in a mass spectrometer if they are otherwise distinguishable on an alternative basis. The internal calibrators can be distinguishable by one or more techniques commonly used to process a sample prior to analysis in a mass spectrometer. For example, the technique can include solid-phase extraction, liquid-liquid extraction, chromatography, electrophoresis, precipitation, derivatization, or a combination thereof. The internal calibrators can be distinguishable on the basis of one or more physicochemical properties. For example, physicochemical property can include solubility (in a solvent, e.g., water or an organic solvent, or a mixture of solvents), retention time (in a separation technique, such as liquid chromatography), affinity (e.g., to an antibody specific for said target analyte to a matrix), dissociation constant, reactivity, and/or specificity towards an enzyme.

The compositions of the present invention include dry preparations and liquid preparation (e.g., a solution, emulsion, suspension, etc.). The preparation can be determined by the requirement of compatibility with the internal calibrator (e.g., which could be incompatible with drying or unstable in liquid) or the sample (e.g., a liquid could be required to facilitate mixing and could need to be aqueous or organic or ion/pH balanced to be compatible with the sample).

Liquid preparation can include various inorganic or organic solvents, or mixtures thereof, which are compatible with the internal calibrators, sample, and MS analysis. In some embodiments, the solvent is selected for compatibility with a preparation, extraction, or separation (e.g., a chromatographic mobile phase and media). Example solvents include water, acetonitrile, aliphatic alcohols (e.g., methanol, ethanol, propanol, iso-propanol), hexafluoroacetone, and combinations thereof. The solvent can include additives, such as buffer salts (e.g., ammonium acetate), inorganic or organic acids (e.g., formic acid, trifluoroacetic acid, orthophosphoric acid, heptafluorobutyric acid), and/or inorganic or organic bases (e.g., $NH_3$).

Dry preparations can be prepared by various conventional drying techniques, such as, air drying, vacuum drying, spray-drying, drum drying, dielectric drying, freeze drying (e.g., lyophilization), supercritical drying, or a combination thereof. Dry preparations include preparations that are substantially free from a liquid, for example a solvent (e.g., water). In various embodiments, dry compositions can be quantified as having less than 10% w/w liquid (e.g., less than 9% w/w liquid, less than 8% w/w liquid, less than 7% w/w liquid, less than 6% w/w liquid, less than 5% w/w liquid, less than 4% w/w liquid, less than 3% w/w liquid, less than 2% w/w liquid, less than 1% w/w liquid, less than 0.5% w/w liquid, or less than 0.1% w/w liquid).

Compositions in accordance with the invention can include one or more additional substances, e.g., substances which improve the stability of the composition, improve or facilitate the processing of a sample, and/or allow, improve or facilitate the analysis of the target analyte(s). Such additional substances include antimicrobial agents (e.g., antibiotics, azides), antioxidants, reducing agents, pH adjusting agents (e.g., inorganic and/or organic acids, bases or buffers), chelating agents (e.g., EDTA), detergents, chaotropic agents, protease inhibitors (e.g., if degradation of peptides/proteins in the sample is to be avoided), DNase inhibitors (e.g., if degradation of DNA in the sample is to be avoided), RNase inhibitors (e.g., if degradation of RNA in the sample is to be avoided), beads (e.g., beads to disrupt cell membranes or beads having ion-exchange, magnetic, size-exclusion, and/or partition properties), proteases (e.g., if degradation of peptides/proteins in the sample is desired), DNase (e.g., if degradation of DNA in the sample is desired), RNase (e.g., if degradation of RNA in the sample is desired), and solvents (e.g., if the composition is in the form of a liquid preparation).

In some embodiments, the compositions (e.g., composition used in commercial kits) include quality control (QC) material, e.g., a dry or liquid preparation containing a known amount of a target analyte, either alone or in combination with one or more internal calibrators of a set of internal calibrators which is specific for said target analyte. In various embodiments, the QC is measured in the matrix. A kit can include a pure analyte as a QC for the user to supply their own blank matrix or, alternatively, a kit can include one or more blank matrices that are pre-spiked or can be selected by the desired use to add to the pure QC material provided in the kit.

For example, a kit can include QC materials for every set of internal calibrators/target analyte. Compositions can include, for example, the internal calibrators and QC material in a single mixture. Kits can include, for example, one or more mixtures of internal calibrators as well as one or more corresponding QC materials.

Compositions in accordance with the invention can be contained in a sample holder defining at least one sample receptacle. The sample holder can be sealable (e.g., a sealable vial, a sealable tube such as a ready-to-use tube, a sealable microtitre plate such as a 6, 24, or 96 well plate, and the like). Numerous sample receptacles, such as vials, tubes, and plates, are known in the art.

In various embodiments, compositions according to the invention can be contained in a sample holder having one or more compartments. In one example, one or more compartments of the sample holder contain internal calibrators (i.e., one or more sets of internal calibrators as described above) in amounts that are sufficient for the analysis of one sample (e.g., including one or more target analytes) per compartment.

In some embodiments, the sample holder defines an array of sample receptacles, each receptacle containing or receiving identical compositions (i.e., sets of two or more internal calibrators for each target analyte), thereby facilitating analyzing a plurality of samples against a common analytical panel. Alternatively, a sample holder can define an array of sample receptacles, each containing or receiving different compositions (i.e., distinct sets of two or more internal calibrators for each target analyte), thereby facilitating analyzing a single sample against a plurality of analytical panels.

In another embodiment, the composition is contained in one compartment (such as a sealable tube or vial) that contains the internal calibrators (e.g., one or more sets of internal calibrators) in amounts and proportions that are sufficient for the analysis of multiple samples. The internal calibrators can be in a dry preparation, which can be reconstituted into a liquid preparation by addition of a solvent. The reconstituted liquid preparation can be added in equal aliquots to each of a plurality of samples to be analyzed, thereby ensuring that each sample includes the same quality and quantity of internal calibrators.

Compositions according to the invention can be contained in ready-to-use reaction tubes, for example, pre-aliquoted reaction tubes that can be directly used for sample processing or analysis. Pre-aliquoted reaction tube can contain internal calibrators in amounts and proportions sufficient for the analysis of one or more samples. For example, the reaction tube may contain 3 sets of internal calibrators, wherein each set contains 4 internal calibrators and the amounts of internal calibrators within each set of internal calibrators differ from each other. The tube can be securely closed (e.g., by a screw cap, snap-on cap, or puncture cap). Example tubes can have a volume in the range of less than 1 mL, 1 to 15 mL, or 1 to 2 mL (e.g., 1.5 mL). In general, the volume of a sample receptacle can be selected on the basis of the nature and amount of sample to be processed/analyzed.

Calibrators can be provided in compositions including (i) individual calibrators, (ii) sets of two or more calibrators for a target analyte, (iii) panels including sets for calibrators for two or more target analytes, and (iv) combination and variations thereof. A user or programmed apparatus can use such compositions (e.g., ii or iii) directly in an assay. Alternatively, a user or programmed apparatus can use such compositions (e.g., i-iv) to prepare a predetermined or customized composition for assaying a particular sample, analyte, or panel of analytes. Customized compositions can be advantageous in random access operation and/or in conducting multi-analyte panels from a single run with a single sample. Therefore, the inventive compositions provide flexibility and adaptability to essentially any assay and assay format.

Kits according to the invention can include any one or more of the compositions described herein, together with instructions (and/or other/additional means) for implementing the methods and/or employing the apparatuses of the invention. Such methods and apparatuses are discussed, in turn, below.

Methods

The invention features methods for quantifying a target analyte by mass spectrometry. The methods include obtaining a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte. The first known quantity and the second known quantity are different, and the first calibrator, the second calibrator, and the target analyte are each distinguishable in the single sample (e.g., by mass spectrometry). The methods also include quantifying the target analyte in the single sample using the first calibrator signal, the second calibrator signal, and the target analyte signal.

As discussed above in the context of the properties and selection of calibrators and analytes, the methods can employ more than two calibrators for a given analyte. For example, a method using three calibrators can include obtaining, from the mass spectrometer signal, a third calibrator signal from the single sample further comprising a third known quantity of a third calibrator where (i) the first known quantity, the second known quantity, and the third known quantity are different, (ii) the first calibrator, the second calibrator, the third calibrator, and the target analyte are each distinguishable in the single sample, and (iii) quantifying the target analyte includes using the third calibrator. A method using four calibrators can further include obtaining, from the mass spectrometer signal, a fourth calibrator signal from the single sample further comprising a fourth known quantity of a fourth calibrator, where (i) the first known quantity, the second known quantity, the third known quantity, and the fourth known quantity are different, (ii) the first calibrator, the second calibrator, the third calibrator, the fourth calibrator and the target analyte are each distinguishable in the single sample, and (iii) quantifying the target analyte includes using the fourth calibrator.

Additional calibrators can potentially be used to increase the precision and/or accuracy of the target analyte quantification. Additional calibrators can also be used where matrix effects are expected to obscure or distort a calibrator signal, thereby ensuring that an accurate calibration curve (or formula) can be determined despite any issues with the calibrator signals. Such additional calibrators are generally in different concentrations from the other calibrators for the given target analyte. However, in some embodiments, such additional calibrators can be in the same or essentially the same concentration as another calibrator as long as two calibrators for the given target analyte are present in different amounts.

As discussed above in the context of the properties and selection of calibrators and analytes, the methods can quantify two or more analytes in a given sample. For example, a method quantifying two analytes (e.g., a target analyte and an additional target analyte) can include (i) obtaining, from the mass spectrometer signal, a third calibrator signal, a fourth calibrator signal, and an additional target analyte signal from the single sample comprising a third known quantity of a third calibrator, comprising a fourth known quantity of a fourth calibrator, and potentially comprising an additional target analyte (where the third known quantity and the fourth known quantity are different, and where the first calibrator, the second calibrator, the third calibrator, the fourth calibrator, the target analyte, and the additional target analyte are each distinguishable in the single sample); and (ii) quantifying the additional target analyte in the single sample using the third calibrator signal, the fourth calibrator signal, and the additional target analyte signal. A method quantifying three analytes (e.g., a target analyte, additional target analyte, and second additional target analyte) can further include (i) obtaining, from the mass spectrometer signal, a fifth calibrator signal, a sixth calibrator signal, and a second additional target analyte signal from the single sample comprising a fifth known quantity of a fifth calibrator, comprising a sixth known quantity of a sixth calibrator, and potentially comprising a second additional target analyte (where the fifth known quantity and the sixth known quantity are different, and wherein the first calibrator, the second calibrator, the third calibrator, the fourth calibrator, the fifth calibrator, the sixth calibrator, the target analyte, the additional target analyte, and the second additional target analyte are each distinguishable in the single sample); and (ii) quantifying the second additional target analyte in the single sample using the fifth calibrator signal, the sixth calibrator signal, and the second additional target analyte signal.

Different methods for obtaining a mass spectrometer signal are known in the art. In various implementations, mass spectrometric analysis includes ionizing one or more compounds to generate charged molecules or molecule fragments and measuring their mass-to-charge ratios (cf. Sparkman, O. D. (2000). Mass spectrometry desk reference. Pittsburgh: Global View Pub. ISBN 0-9660813-2-3). Such procedures can include the following steps: loading a mixture containing one or more compounds onto the MS instrument and vaporizing the one or more compounds; ionizing the components of the mixture, to form charged particles (ions); electromagnetically separating the ions according to their mass-to-charge ratio in an analyzer; detecting the ions (e.g., by a quantitative method); and transforming the ion signals into mass spectra.

The mass spectrometer can be operated, for example, in any of the following modes: (1) full scan, e.g., the mass spectrometer detects all ions between two distant points on the m/z scale (such as 0 and 10000); (2) Single Ion Monitoring (SIM) or Single Ion Recording (SIR), e.g., the mass spectrometer detects only ions which have a particular m/z value or which lie within a small mass m/z range (e.g., a range of 1 or 2 mass units); (3) Multiple Reaction Monitoring (MRM), e.g., in a mass spectrometer having multiple mass spectrometer units, at least two units are operated in the SIM/SIR mode.

After separation and measurement of the intensities of the ions in the mass spectrometer, mass spectra are created, for example by plotting the intensities measured for the detected ions vs. their mass-to-charge ratio (m/z). Depending on the mode by which the mass spectrometer is operated (full scan, SIM/SIR, or MRM), the mass spectra can include (1) the peaks corresponding to all ions (precursor and product ions) detected in the mass spectrometer between two distant points on the m/z scale; (2) the peaks corresponding to (a) all ions which have a particular m/z value or which lie within a very small m/z range and optionally (b) all product ions derived from the ions specified under (a); or (3) only one or more selected product/daughter ions (MRM channels).

For example, when the mass spectrometer is operated in MRM mode, one can create a single mass spectrum for a set of internal calibrators and corresponding target analyte. The single mass spectrum will contain one peak for each internal calibrator and, if present in the sample, one peak for the corresponding target analyte. Alternatively, multiple mass spectra can be created for the first set of internal calibrators and corresponding target analyte, where each of the multiple mass spectra only represents one of the internal calibrators or corresponding target analyte. Such single mass spectrum or multiple mass spectra can be created for each set of internal calibrators and corresponding target analyte.

Mass spectra created using MRM channels and where peak intensities are plotted against time (such as retention time if the mass spectrometer is coupled to a SPE, chromatography, or electrophoresis device) are often described as mass chromatograms. Thus, the term mass spectra, as used herein, can also relate to mass chromatograms (e.g., where the MS operates in MRM mode).

Next, the MS signal intensities (or relative signal intensities) of the ions representative of each of the internal calibrators and corresponding target analyte(s) are determined. The signal intensities of the ions in the mass spectra (e.g., the intensities of the peaks corresponding to these ions) can be determined on the basis of the peak height or peak area, for example on the basis of peak area such as by integrating the signal intensity of a specific ion with respect to time. The intensities of the ions signals in the mass spectrum/spectra can be normalized e.g., to 100%, to the most intense ion signal detected.

As discussed above in the context of the properties and selection of calibrators, analytes, compositions, and kits, the calibrators and corresponding target analyte(s) can be distinguished from each other based on their behavior in a mass spectrometer (e.g., due to differences in their mass and/or fragmentation pattern).

In one embodiment, any two or more compounds (e.g., the first and second calibrators and the target analyte) are distinguished and separated from each other in a mass spectrometer due to differences in their mass (e.g., due to difference in the mass of the precursor ions/parent ions derived from the two compounds). The masses of the two compounds (e.g., the first internal calibrator and the target analyte) can differ by a number of mass units that are resolvable by the instrumentation being used or that meet a predetermined cutoff. For example, the difference in mass of at least 1 (or 2, 3, 4, 5, . . . ) mass units between these two parent/precursor ions can originate from the presence of different isotopes (e.g., low abundant isotopes in one of the two parent/precursor ions vs. high abundant isotopes in the other of the two parent/precursor ions).

In another embodiment, any two or more compounds (e.g., the first and second calibrators and the target analyte) are distinguished and separated from each other in a mass spectrometer due to differences in their fragmentation pattern. The fragmentation pattern can be generated as follows: a series of ions (precursor or parent ions) having the same mass-to-charge ratio are isolated from the compounds entering a mass spectrometer; the parent ions having the same mass-to-charge ratio are stabilized while they collide with a gas, causing them to fragment by collision-induced dissociation (CID), thereby generating product/daughter ions. The fragments (e.g., product/daughter ions) generated or derived from one compound (e.g., the first internal calibrator) of the two compounds during the mass spectrometric analysis may include at least one fragment (e.g., product/daughter ion) having a mass which is distinct from the fragments generated or derived from the other compound (e.g., the target analyte) of the two compounds during the mass spectrometric analysis.

Next, the target analyte in the single sample is quantified using the first calibrator signal, the second calibrator signal, and the target analyte signal. The methods include quantifying the target analyte using the target analyte signal and a calibration curve or algebraic equation (i.e., based upon the calibrator signals). For example, the method can include (i) obtaining a calibration curve from the first calibrator signal and the second calibrator signal; and (ii) quantifying the target analyte using the calibration curve and the target analyte signal. Alternatively, the method can include quantifying the target analyte algebraically using the first calibrator signal, the second calibrator signal, and the target analyte signal. In various embodiments (e.g., two or more calibrators for a given target analyte, two or more target analytes, and combinations thereof), the quantifying step can be carried out manually (e.g., using pencil and paper, a calculator, or a spreadsheet, for example in a one-off, research, or development setting) or automatically (e.g., using a programmed machine or purpose built machine, for example in a high-throughput or commercial setting).

Calibration curves can be obtained by applying a suitable regression algorithm (e.g., a Gauss least-square fitting method) to the data. Suitable regression algorithms can include the following steps: (1) selecting a mathematical function (model); (2) fitting the function from the experimental data; and (3) validating the model. The function can be, but is not necessarily, linear over the entire analytical range. Where the method is quantifying multiple target analytes, the step of creating a calibration curve using the corresponding calibrator signals can be performed for each set of internal calibrators, thereby creating a distinct calibration curve for each corresponding target analyte.

The amount of target analyte, if present in the sample, can be quantified using the calibration curve. For example, quantification can be achieved by extrapolation using (1) a calibration curve based upon the calibrators corresponding to the target analyte and (2) the target analyte signal. Where the method is quantifying multiple target analytes, the step of extrapolation on the bases of the respective calibration curves and target analyte signals can be performed for each target analyte, thereby quantifying each corresponding target analyte.

In various embodiments, the methods include one or more additional steps before mass spectrometry. Additional steps can be conducted manually or can be automated (e.g., in a specifically programmed or specifically built machine).

In one embodiment, the method also includes (i) preparing the single sample by combining the first known quantity of the first calibrator and the second known quantity of the second calibrator in a single specimen potentially comprising the target analyte; and (ii) generating the mass spectrometer signal from the single sample using a mass spectrometer. Suitable sample preparation can vary depending upon the nature of the sample, calibrators, and analytical protocol. For example, sample preparation can include selecting suitable calibrators, selecting an analytical panel, and/or selecting the amounts of the various internal calibrators.

In another embodiment, the method also includes processing the sample prior to obtaining the mass spectrometer signal. For example, processing the sample can include separating the first calibrator, the second calibrator, and the target analyte from other components of the single sample. Processing can be performed by techniques commonly used for processing samples prior to MS analysis, or by a combination of such techniques, in order to (1) reduce the number of compounds introduced into the mass spectrometer; (2) concentrate the internal calibrators and target analyte(s), e.g., by depleting unwanted compounds and/or enrichment of the internal calibrator and target analyte; (3) separate the internal calibrators and target analyte(s) from other compounds that could interfere with the MS analysis; and/or (4) separate at least one set of internal calibrators and corresponding target analyte from other sets of internal calibrators and corresponding target analytes. Such techniques can include one or more of solid phase extraction, liquid phase extraction, and chromatography (e.g., liquid, gas, affinity, immunoaffinity, and supercritical fluid chromatography).

Figures 2, 2A:
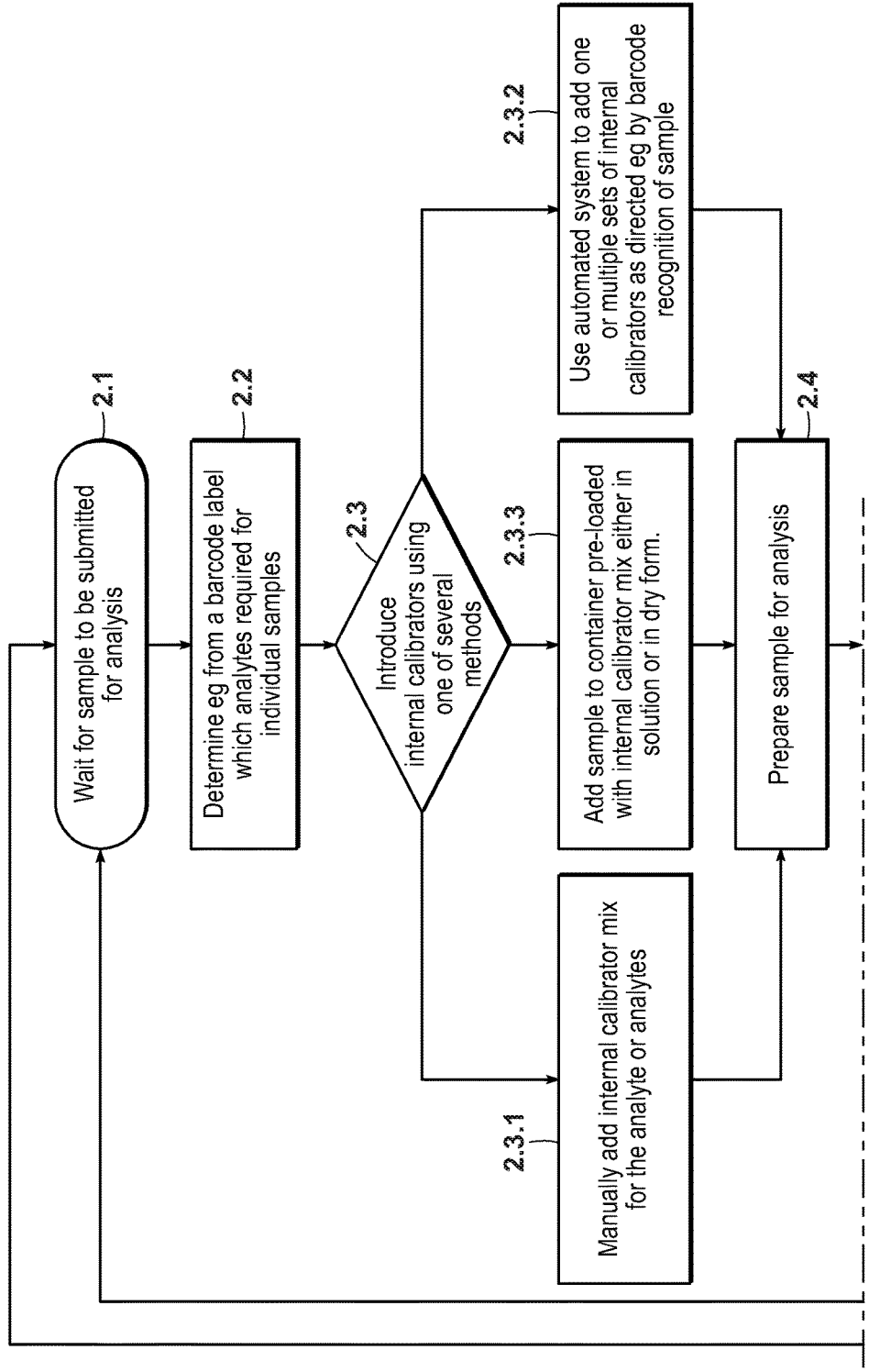
Figure 2C:
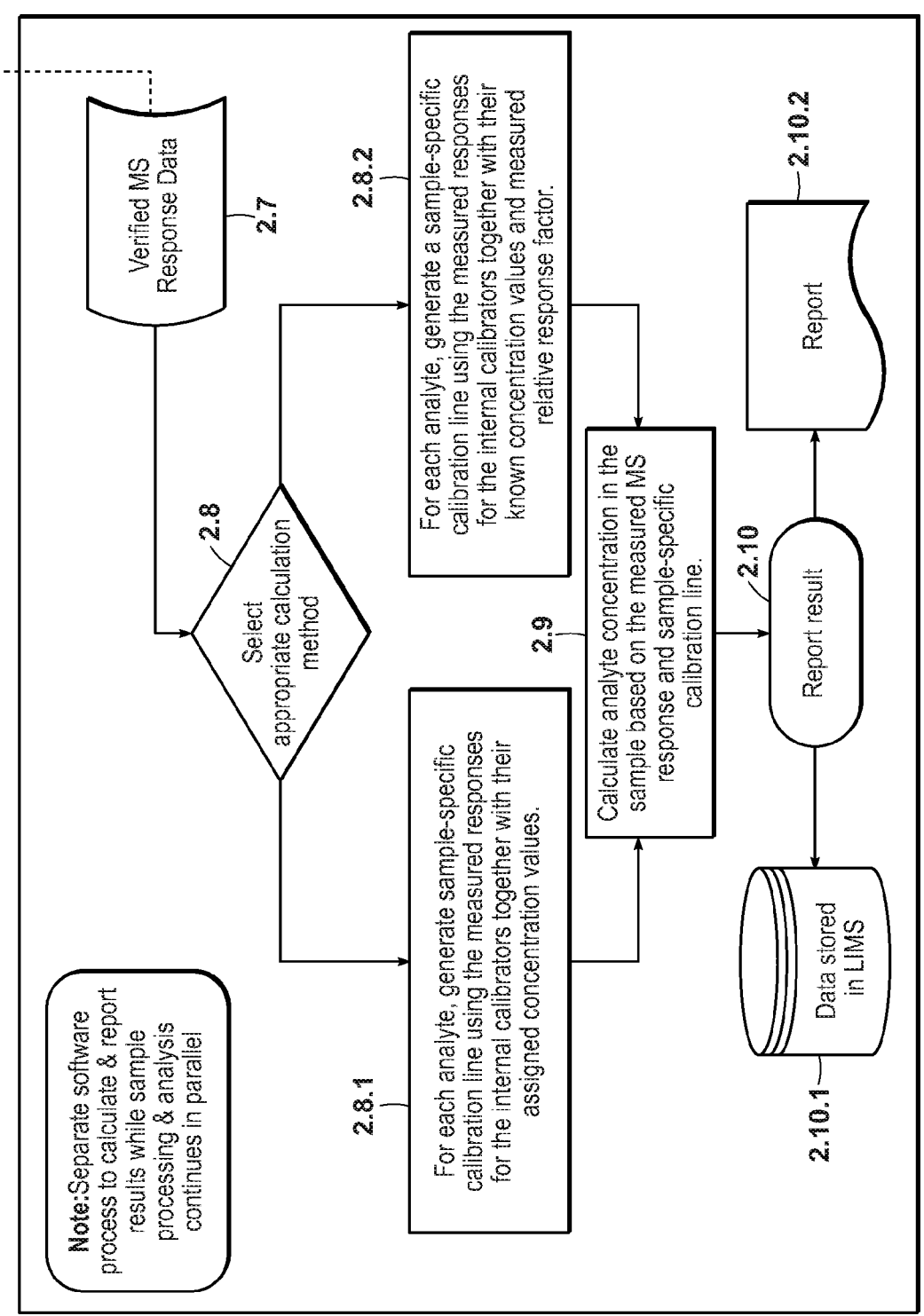

FIG. 2A-C presents a flow chart outlining an example method for quantifying one or more samples, each independently including an analyte or panel of analytes, in using internal calibration. In various implementations, the method of FIG. 2A-C can be carried out manually, semi-automatically, or automatically. Similarly, one or more steps can be added, omitted, and/or repeated. The method of FIG. 2A-C (and its variants) can also serve as the basis for instructions (e.g., to be included in a kit, in human and/or machine readable format), for a program (e.g., an algorithm or computer program, embodied in a computer readable medium), and/or for analytical system (e.g., specifically adapted or purpose-built machine).

FIG. 2A, step 2.1 includes waiting for a sample to be submitted for analysis. Samples can include quality control samples or system suitability samples, as well as routine samples (e.g., samples potentially including a target analyte). Because the method does not require analysing a separate series of calibrators (e.g., the calibrators and target analyte(s) are in a single sample), samples can be submitted in any order rather than as batches grouped according to the analysis that is required (e.g., the method is a random access method). In some embodiments, a bar-code label or other unique identifier is attached to the sample, to inform a user or automated system which internal calibrator set(s) to add to the sample and can thus also instruct the user or automated system to use appropriate LC and/or MS parameters.

FIG. 2A, step 2.2 includes determining (e.g., on the basis of a barcode label) which calibrators are desired for a given sample.

FIG. 2A, step 2.3 includes introducing internal calibrators into the sample. The internal calibrators can be added to the sample in different ways, for example, to suit automated or manual processes and to allow the determination of a single analyte or a panel of analytes in one assay. For example, FIG. 2A, step 2.3.1 shows an embodiment where calibrators corresponding to the analyte(s) are added to the sample manually, FIG. 2A, step 2.3.2 shows an embodiment where the sample is added to a container that is pre-loaded with calibrators (e.g., in a solution or dry format), and FIG. 2A, step 2.3.3 shows an embodiment where an automated system is used to add one or more sets of internal calibrators (e.g., as directed, for example, by barcode recognition of sample).

FIG. 2A, step 2.4 includes preparing the sample for analysis. Sample preparation can include any of the various techniques discussed herein, for example, protein precipitation, solid phase extraction, liquid-liquid extraction, immunoaffinity purification, affinity purification, and the like. Sample preparation can be carried out on-line or off-line.

FIG. 2B, step 2.5 includes analysing the sample by MS (e.g., using MS to measure the response, such as chromatographic peak area, of the target analyte and corresponding calibrators).

FIG. 2B, step 2.6 includes checking the data quality from FIG. 2B, step 2.5. If the data is not acceptable, the sample can be resubmitted for analysis (e.g., return to FIG. 2A, step 2.1). If the data is acceptable, the verified MS response data FIG. 2B, step 2.7 can be used to quantify the target analyte(s).

FIG. 2C, step 2.8 includes selecting an appropriate calculation method for quantifying the target analyte(s). One option is illustrated in FIG. 2C, step 2.8.1, which includes generating a sample-specific calibration line for each target analyte using the measured responses for the internal calibrators, together with their assigned concentration values. Another option is illustrated in FIG. 2C, step 2.8.2, which includes generating a sample-specific calibration line for each target analyte using the measured responses for the internal calibrators together with their known concentration values and measured relative response factor.

FIG. 2C, step 2.9 includes calculating the target analyte concentration(s) in the single sample based upon the measured MS response and sample-specific calibration line. In an alternative embodiment, the target analyte concentration(s) can be calculated algebraically using the target analyte signal and the corresponding calibrator signals.

FIG. 2C, step 2.10 includes reporting the result. In various embodiment, the result can be stored (FIG. 2C, step 2.10.1) in a computer (e.g., in a laboratory information management system or LIMS). In various embodiments, the result can be reported (FIG. 2C, step 2.10.2) in a user readable format such as a printed report or screen display. Reporting methods are not mutually exclusive and the result can be reported and/or stored by two or more techniques.

Whereas FIG. 2A, step 2.1 through FIG. 2B, step 2.6 pertain most directly to a specifically programmed or specifically built machine for carrying out the method, the following FIG. 2C, steps 2.8 through 2.10 pertain most directly to a software-based process that calculates and reports the results. Both processes can be completed by a single apparatus (e.g., where calculation is carried out on a computer that also controls the MS and sample handling hardware). However, because the steps are separable, the sample processing and analysis steps can continue in parallel to the calculation and reporting steps, thereby increasing the speed and efficiency of the apparatus.

The methods of the invention can be embodied in tangible articles. For example, the methods can be included as instructions in a kit and/or can be in a computer readable medium including computer executable instructions (e.g., for operating an apparatus that implements the method). Instructions can include directions for executing, adapting, or modifying any one or more methods described herein and can be embodied in hard copy (e.g., handbooks, printouts, and the like) or in soft copy (e.g., electronic, in computer memory or storage, on a display, and the like). Likewise, computer readable media (e.g., disk storage, solid state memory, and the like) can include computer executable instructions for executing, adapting, or modifying any one or more methods described herein.

Analytical Systems

The invention features apparatuses for quantifying a target analyte by mass spectrometry. In various embodiments, the apparatuses are configured to implement the methods of the invention, as well as variations and combinations thereof.

Figure 3:
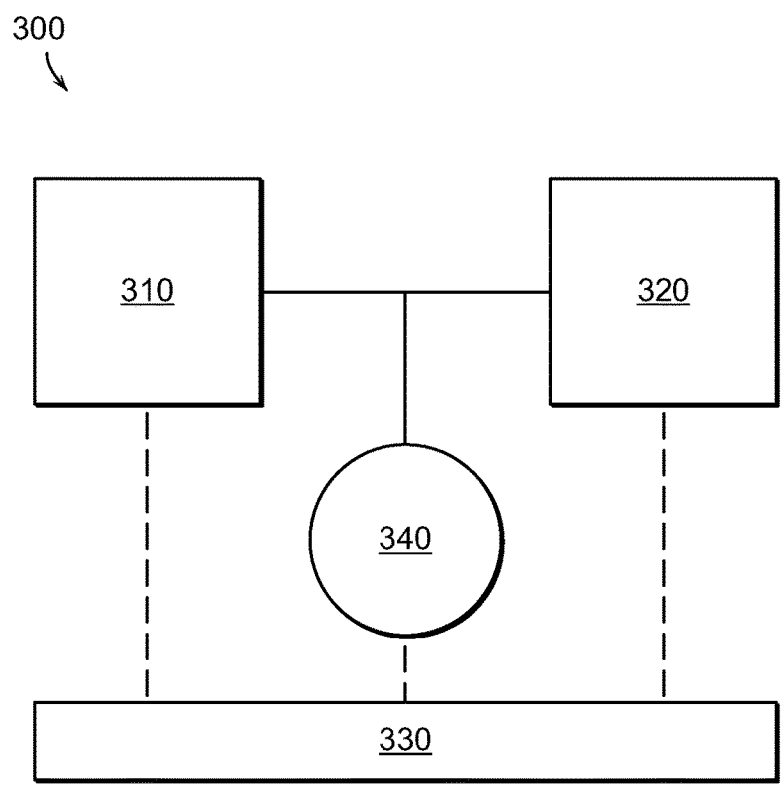
Figure 4A:
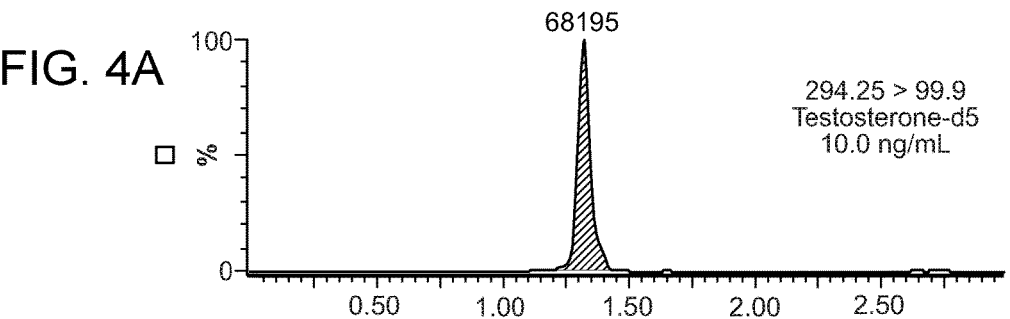
Figure 4B:
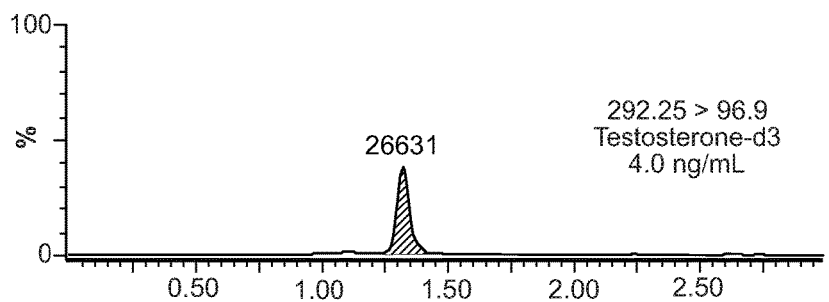
Figure 4C:
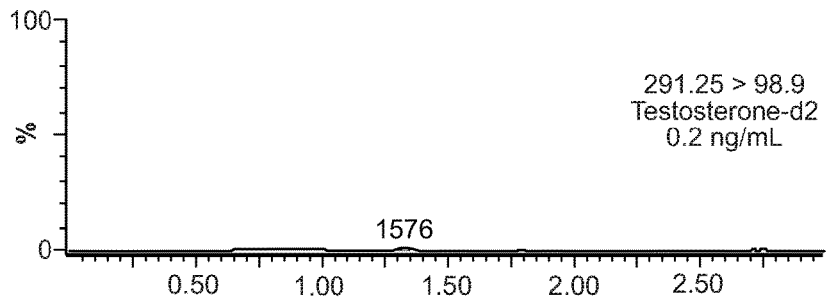
Figure 4D:
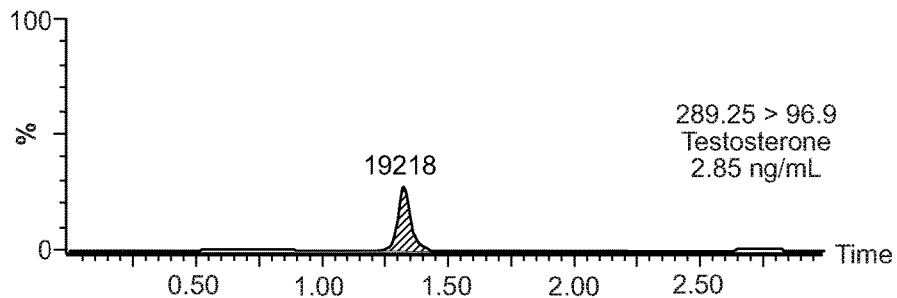

FIG. 3 illustrates an example apparatus 300 including a sample handler 310 configured to prepare the single sample by combining a first known quantity of a first calibrator and a second known quantity of a second calibrator in a single specimen potentially comprising a target analyte. The apparatus 300 also includes a mass spectrometer 320 configured to generate a mass spectrometer signal comprising a first calibrator signal, comprising a second calibrator signal, and potentially comprising a target analyte signal from a single sample comprising a first known quantity of a first calibrator, comprising a second known quantity of a second calibrator, and potentially comprising a target analyte, wherein the first known quantity and the second known quantity are different, and wherein the first calibrator, the second calibrator, and the target analyte are each distinguishable in the single sample by mass spectrometry. Furthermore, the apparatus 300 includes a data processor 330 configured to quantify the target analyte in the single sample using the first calibrator signal, the second calibrator signal, and the target analyte signal. In some embodiments, the apparatus 300 also includes a pre-treatment and/or separation system 340 configured to separate the first calibrator, the second calibrator, and the target analyte from other components of the single sample prior to obtaining a mass spectrometer signal. Pre-treatment can include SPE, liquid-liquid extraction, precipitation, and the like. Separation can include chromatography, for example LC, HPLC, UPLC, SFC, and the like. The pre-treatment and/or separation system 340, or a subset of the components thereof, can operate in an off-line or on-line mode.

The sample handler 310 can be based upon conventional sample handling equipment. Examples of suitable sample handlers include the Tecan EVO (off line) and the Waters AQUITY SPE Manager (on line). The sample handler can be adapted by methods known in the art, including the addition of a bar code reader, vacuum manifold, centrifuge, pipette, and robots, as well as scripting to control the apparatus in a predetermined manner.

In some embodiments, the sample handler 310 can be adapted for random access operation and/or in conducting multi-analyte panels from a single run with a single sample. For example, the sample handler 310 can include (i) an automated code reader configured to determine a listing of one or more analytes to be tested for in a given specimen based upon a code associated with the given specimen; and (ii) an automated calibrator system configured to combine the given specimen with a first known quantity of a first calibrator and a second known quantity of a second calibrator for each of the one or more analytes.

Where the calibrators are prepared ahead of time (e.g., in the form of a vial or plate with a predetermined assay setup), the automated calibrator system can be configured to deliver the given specimen to a sample receptacle comprising the first known quantity of the first calibrator and the second known quantity of the second calibrator for each of the one or more analytes. Alternatively, where the calibrators are prepared on the fly (e.g., customized for a given sample or made to order from individual calibrator components in accordance with a predetermined recipe), the automated calibrator system can be configured to deliver the first known quantity of the first calibrator and the second known quantity of the second calibrator for each of the one or more analytes to a sample receptacle comprising the given specimen.

The mass spectrometer 320 (as well as the mass spectrometers of any of the methods of the invention) can be essentially any instrument that includes an ionization source, an analyzer, and a detector suitable for producing mass spectra. The mass spectrometer may contain multiple mass spectrometer units (MS$^n$ where n=2, 3, 4, . . . ) and/or can be coupled to other instruments, such as a chromatography or electrophoresis device (e.g., a separation system 340, for example in LC/MS/MS).

The mass spectrometer 320 can include an ion source such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionisation ("DESI") ion source; a Nickel-63 radioactive ion source; an Atmospheric Pressure Matrix Assisted Laser Desorption Ionisation ion source; and a Thermospray ion source.

The mass spectrometer 320 can include a mass analyzer such as a quadrupole mass analyzer; a 2D or linear quadrupole mass analyzer; a Paul or 3D quadrupole mass analyzer; a 2D or linear quadrupole ion trap mass analyzer; a Paul or 3D quadrupole ion trap mass analyzer; a Penning trap mass analyzer; an ion trap mass analyzer; a magnetic sector mass analyzer; Ion Cyclotron Resonance ("ICR") mass analyzer; a Fourier Transform Ion Cyclotron Resonance ("FTICR") mass analyzer; an electrostatic or orbitrap mass analyzer; a Fourier Transform electrostatic or orbitrap mass analyzer; a Fourier Transform mass analyzer; a Time of Flight mass analyzer; an orthogonal acceleration Time of Flight mass analyzer; and a linear acceleration Time of Flight mass analyzer. The mass spectrometer can include an ion mobility analyzer.

The mass spectrometer 320 can include an ionization sources such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionisation ("DESI") ion source; a Nickel-63 radioactive ion source; an Atmospheric Pressure Matrix Assisted Laser Desorption Ionisation ion source; and a Thermospray ion source.

The data processor 330 can include a computer suitable for quantify the target analyte using the MS signal. For example, a Windows PC running MassLynx can be used to control the system, collect data, and/or generate chromatograms. A module for MassLynx can be developed for conducting internal calibrator calculations. Internal calibrator calculations can also be performed manually or using conventional spreadsheet programs such as Microsoft Excel, a script, or other computer program.

In various embodiments, a data processor 330 can be in communication with any one or more components of an analytical system. For example, the data processor can be in communication with the sample handler 310, to ensure that (i) appropriate calibrators are combined with the sample, (ii) the sample is prepared appropriately, and/or (ii) the sample is analyzed appropriately. The data processor can be in communication with the mass spectrometer 320 to control the mass spectrometer and/or receive a signal from the mass spectrometer for analysis. Similarly, the data processor can be in communication with the separation system 340 to control the separation system and/or receive a signal from the separation system for analysis. The data processor 330 can be adapted to implement various additional functions (see, e.g., the functions described in connection with FIG. 2A-D, for example quality control, data storage, data reporting, and the like.

In general, the separation system 340 can separate one or more calibrator(s)/analyte(s) from each other and/or from at least a portion of the sample (e.g., matrix, contaminants). The separation system 340 can include at least one separation, chromatography, or similar system (e.g., liquid chromatography, gas chromatography, affinity, immunoaffinity, supercritical fluid chromatography equipment, and the like) for separating the calibrators and target analyte(s) from other components of the single sample prior to obtaining a mass spectrometer signal. Prior to separation, the separation system 340 can also employ one or more sample preparation/pre-treatment steps. For example, at least a portion of a sample can be pre-processed by solid-phase extraction (e.g., normal phase solid-phase extraction (SPE), reversed phase SPE, ion-exchange SPE, size exclusion SPE, affinity SPE or a combination thereof), liquid-liquid extraction, precipitation, derivatization, or any combination thereof. Separation can include, for example, chromatography (e.g., liquid chromatography such as HPLC, Supercritical Fluid Chromatography (SFC), Ultra Performance Liquid Chromatography (UPLC), Ultra High Performance Liquid Chromatography (UHPLC), nano-LC, in particular normal phase chromatography, reversed phase chromatography, ion-exchange chromatography, size-exclusion chromatography, affinity chromatography) or gas chromatography), electrophoresis (e.g., capillary electrophoresis). The separation system 340 can be coupled to a mass spectrometer (on-line mode) or not (off-line mode).

EXAMPLES

Unless indicated otherwise, all techniques, including the use of kits and reagents, were carried out according to the manufacturers' information, methods known in the art, or as described, for example, in *Tietz Text Book of Clinical Chemistry* 3$^{rd}$ Edition (Burtis, C. A. & Ashwood, M. D., Eds.) W. B. Saunders Company, 1999; *Guidance for Industry. Bioanalytical Method Validation*. USA: Centre for Drug Evaluation and Research, US Department of Health and Social Services, Food and Drug Administration, 2001; and Sambrook et al., Molecular Cloning: A Laboratory Manual, 2$^{nd}$ Edition (1989) Cold Spring Harbor Laboratory Press, Cold Spring Harbor, N.Y. The methods used below and described in these references are hereby incorporated by reference in their entirety.

Example 1: The Analysis of Testosterone Using Multipoint Calibration in a Single Analysis (Internal Calibration)

Summary:

Conventional quantitative LC/MS/MS requires a set of matrix-based calibrators to be analyzed with each batch of samples. This limits the technique to a batch mode of analysis, delays the time to first result and for reagent kits, and requires the manufacturer to source and process analyte-free matrix. This is particularly difficult when the analytes of interest are ordinarily present in the matrix (e.g., endogenous hormones, vitamins, peptides, etc.). This example describes a quantitative LC/MS/MS method where each sample is supplemented with multiple stable isotope labeled analogs of the analyte. Each analog is added at a known unique concentration spanning the analytical measurement range. The analogs and the analyte can be distinguished from each other on the basis of their MS characteristics such that in a single analysis, the responses for the analogs and the analyte can be measured simultaneously. This allows an individual calibration curve to be constructed and a result generated for each sample from a single analysis of a single sample. This example demonstrates that by using stable isotope labeled internal calibrators, testosterone can be precisely and accurately quantified in human serum. The method illustrated by this example allows for random access LC/MS/MS analysis, decreases the time to first result relative to conventional methods, and simplifies the manufacture of reagent kits by eliminating the requirement to source matrix.

Methods

Preparation of Calibrators:

For the conventional assay (e.g., comparison), testosterone spiking solutions were prepared at 10 ng/mL, 100 ng/mL, or 1000 ng/mL. Six separate calibrators were prepared by spiking testosterone into 1.0 mL aliquots of blank matrix (e.g., commercially available double charcoal stripped serum). The final concentrations of the calibrators were 0.1, 0.5, 1.0, 2.0, 5.0, and 15.0 ng/mL.

For the internal calibration assay, three commercially available stable isotope labeled internal calibrators were used (di-, tri-, and penta-deuterated testosterone). The internal calibrator MS/MS characteristics were investigated and a specific MRM transition selected for each (see Table 2 and FIG. 4A-D). The selected transitions represent the same mode of fragmentation (see Formula 1) but are unique to each internal calibrator because of the mass shift caused by the incorporation of deuterium.

TABLE 2

MS/MS Characteristics of testosterone and the selected internal calibrators.

| Analyte or Internal Calibrator | MRM Transition | Cone Voltage (V) | Collision Energy (eV) |
|---|---|---|---|
| testosterone | 289.25 > 96.9 | 28 | 30 |
| testosterone-d2 | 291.25 > 98.9 | 28 | 30 |
| testosterone-d3 | 292.25 > 96.9 | 28 | 30 |
| testosterone-d5 | 294.25 > 99.9 | 28 | 30 |

FIG. 4A-D shows an example of typical chromatograms for the analysis of a sample using the internal calibration method, in particular the target analyte (testosterone) and corresponding internal calibrators (d2, d3, and d5 analogs of testosterone).

Formula 1 shows the structure and proposed fragmentation scheme of testosterone (T) to generate the m/z 97 fragment from the A ring. The positions of the deuterium atoms in each of the internal calibrators were: T-d2: 1,2; T-d3: 16,16,17; T-d5: 2,2,4,6,6.

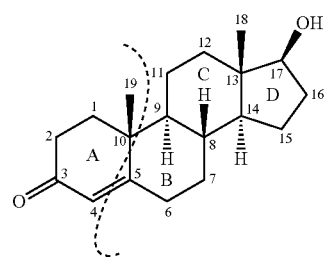

Formula 1

Individual stock solutions were prepared for each of the internal calibrators and a 0.5 ng/mL dilution was made from each stock solution. The dilutions were analyzed by UPLC/MS/MS as described below, using the specific MRM transitions described in Table 2. The mean integrated peak areas from five replicate injections of each dilution were compared to the values obtained for unlabeled testosterone and the relative response factors calculated (Table 3).

Table 3 shows a comparison of internal calibrator and testosterone (T) Stock Solutions. The mean integrated peak area from five replicate analyses of each internal calibrator was compared with the mean integrated peak area for unlabeled testosterone to determine the relative response.

TABLE 3

Comparison of Internal Calibrator and Testosterone (T) Stock Solutions.

| | Integrated Peak Area | | | |
|---|---|---|---|---|
| Analysis # | T | T-d2 | T-d3 | T-d5 |
| 1 | 6200.2 | 6922.6 | 5454.4 | 7296.9 |
| 2 | 6280.8 | 7073.8 | 5424.4 | 7108.5 |
| 3 | 6271.3 | 6752.2 | 5549.4 | 7256.5 |
| 4 | 6357.8 | 6894.1 | 5439.9 | 7458.7 |
| 5 | 6292.5 | 6735.0 | 5345.0 | 6824.0 |
| Mean | 6280.5 (A) | 6875.5 (B) | 5442.6 (C) | 7188.9 (D) |
| SD | 56.2 | 138.6 | 73.2 | 239.1 |
| % CV | 0.90 | 2.02 | 1.34 | 3.33 |
| Relative Response Factor | 1 | 1.095 (B/A) | 0.867 (C/A) | 1.145 (D/A) |

Note:
Coefficient of variation (CV) is a normalized measure of dispersion of a probable distribution (i.e., the ratio of the SD to the mean).

Figure 5:
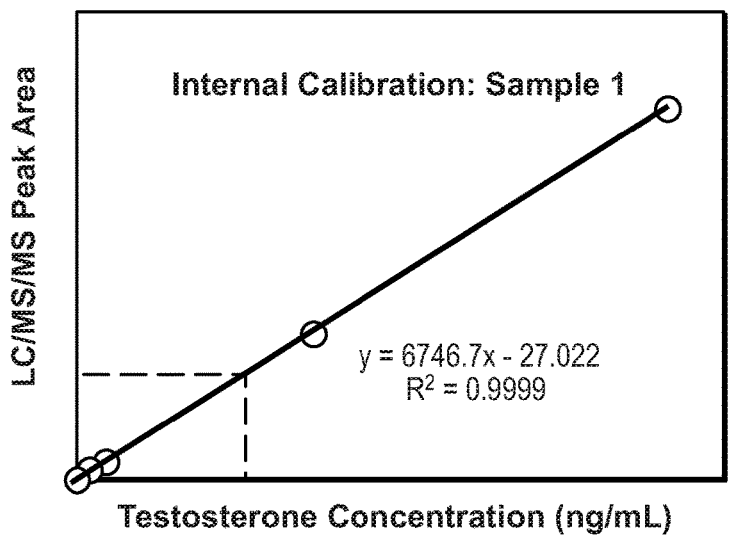
FIG. 5 shows an example of a sample-specific calibration curve generated from the data shown in FIG. 4A-D.

FIG. 5 shows an example of a sample-specific calibration curve generated from the data shown in FIG. 4A-D. From the peak area measured in the testosterone MRM, the concentration is calculated to be 2.85 ng/mL (dotted line). The relative response factors were used to assign concentration values to the internal calibrator stock solutions (e.g., the assigned concentration of the testosterone-d2 stock solution was 1.095× the concentration of the testosterone stock solution). The internal calibrator stock solutions were spiked into 60% MeOH to generate a single solution that contained the following concentrations of each internal calibrator, based on the assigned concentration: 2.2 ng/mL testosterone-d2, 44.0 ng/mL testosterone-d3, and 110 ng/mL testosterone-d5.

Patient Samples:

Fifty anonymous left-over specimens from routine serum testosterone measurements were used for this study. Five of the samples had insufficient volume for testing by both the conventional and internal calibration LC/MS/MS assays. These five samples were used to make a pool that was analyzed in both assays as sample #46. The pool was also used for a preliminary assessment of precision in the internal calibration assay.

Sample Preparation:

For the conventional assay

1. Place 100 μL of each matrix calibrator (N=6) or 100 μL of each patient sample (N=46) into separate Eppendorf tubes.
2. Add internal standard (testosterone-d3 in 60% MeOH; 10 μL) to each tube.
3. Vortex mix.
4. Add 1.0 mL MTBE to each tube, cap and vortex mix.
5. Centrifuge at 15,000 RPM for 5 min at room temperature.
6. Recover as much of the upper (organic) phase as possible into a Waters Maximum Recovery vial and reduce to dryness under a stream of Nitrogen.
7. Redissolve the residue in 75 μL 60% MeOH and analyse by UPLC/MS/MS (see below).

For the Internal Calibration Assay

1. Place 100 μL of each patient sample (N=46) into separate Eppendorf tubes.
2. Add internal calibrator mix (10.0 μL) to each tube.
3. Vortex mix.
4. Add 1.0 mL MTBE to each tube, cap and vortex mix.
5. Centrifuge at 15,000 RPM for 5 min at room temperature.
6. Recover as much of the upper (organic) phase as possible into a Waters Maximum Recovery vial and reduce to dryness under a stream of Nitrogen.
7. Redissolve the residue in 75 μL 60% MeOH and analyse by UPLC/MS/MS (see below).

Ultra Performance Liquid Chromatography—Tandem Mass Spectrometry (UPLC/MS/MS):

Chromatography was performed using a Waters ACQUITY UPLC system. Samples (15 μL) were analyzed using a Waters CSH Flurophenyl Column (2.1 mm×50 mm) eluted with a gradient of methanol and water containing ammonium acetate and formic acid as shown in Table 4. The run time was 3.5 min with an injection to injection interval of approximately 4 min. The results of separation are shown in Table 4, in which mobile phase A was 2 mM ammonium acetate and 0.1% formic acid in water and mobile phase B was 2 mM ammonium acetate and 0.1% formic acid in methanol.

TABLE 4

UPLC gradient profile for the analysis of testosterone.

| Time (min) | Flow Rate (mL/min) | % A | % B | Curve |
|---|---|---|---|---|
| 0 | 0.35 | 40 | 60 | — |
| 1.80 | 0.35 | 36 | 64 | 7 |
| 1.81 | 0.35 | 0 | 100 | 6 |
| 2.80 | 0.35 | 40 | 60 | 11 |
| 3.50 | 0.35 | 40 | 60 | 6 |

The eluent from the UPLC column was directed into the electrospray ionization source of a Waters Xevo TQ tandem quadrupole mass spectrometer operated in multiple reaction monitoring (MRM) mode. For the conventional assay, two MRM transitions were monitored (testosterone and testosterone-d3; see Table 5) using a dwell time of 100 ms.

TargetLynx software was used to perform peak area integration, calculate response (analyte peak area/internal standard peak area ratio), generate a six point external calibration line and to calculate the analyte concentration in each of the serum samples. For the internal calibration assay, all four MRM channels shown in Table 6 were monitored using a dwell time of 60 ms. Integrated peak areas were determined using TargetLynx software and Microsoft Excel was used to construct individual internal calibration curves for each of the serum samples using linear regression analysis.

Results

Figure 7:
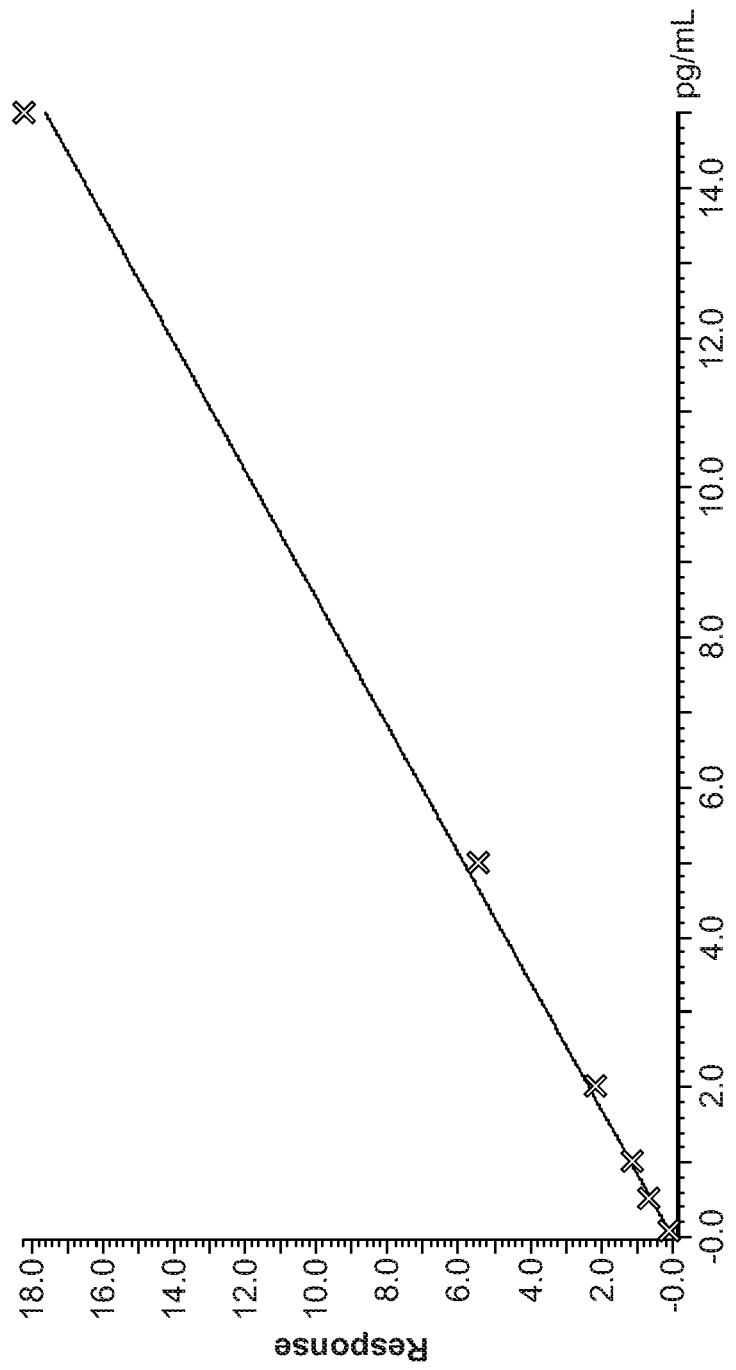
FIG. 7 shows an external calibration line for testosterone generated by TargetLynx.
Figure 8A:
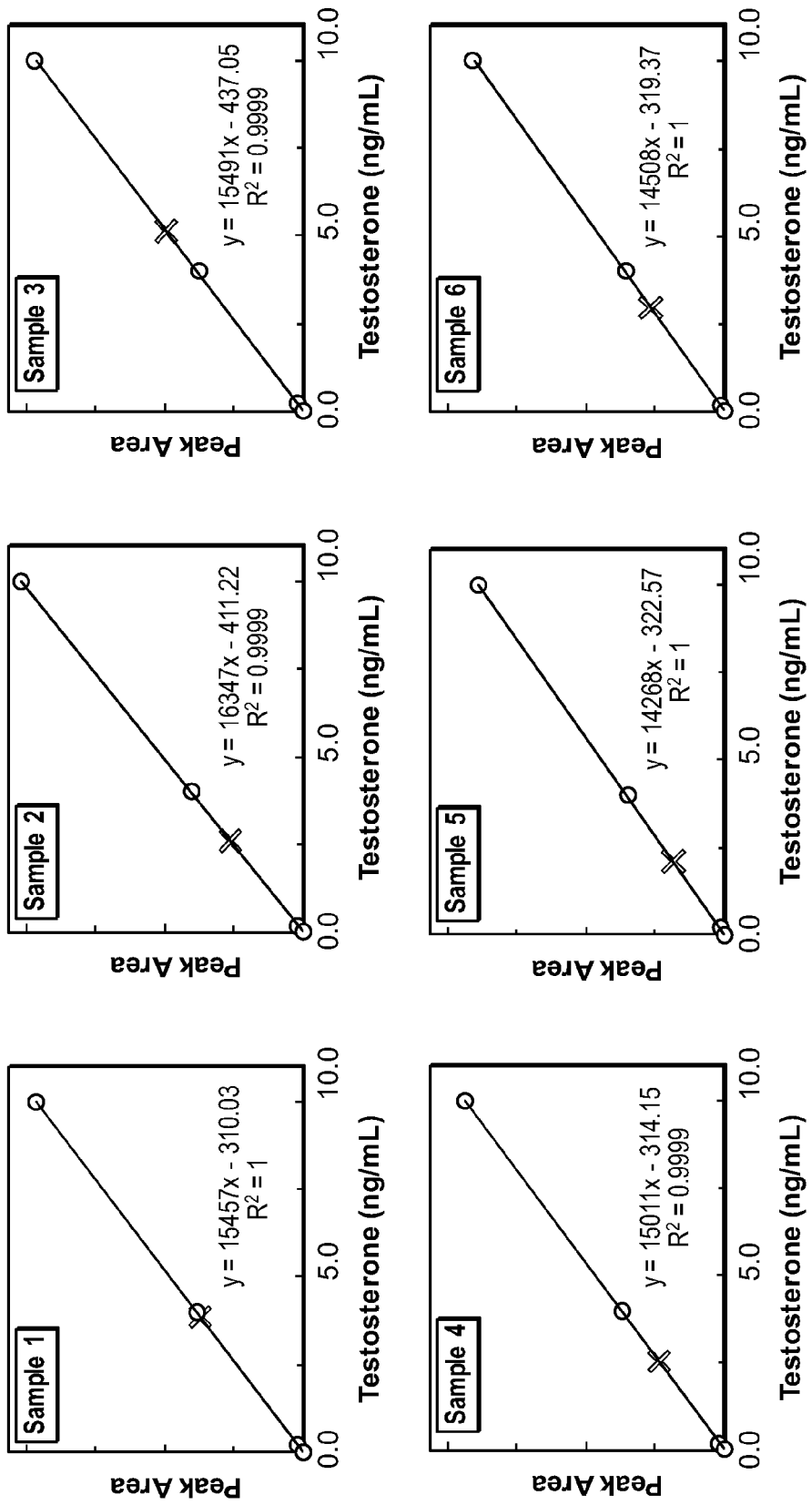
Figure 8B:
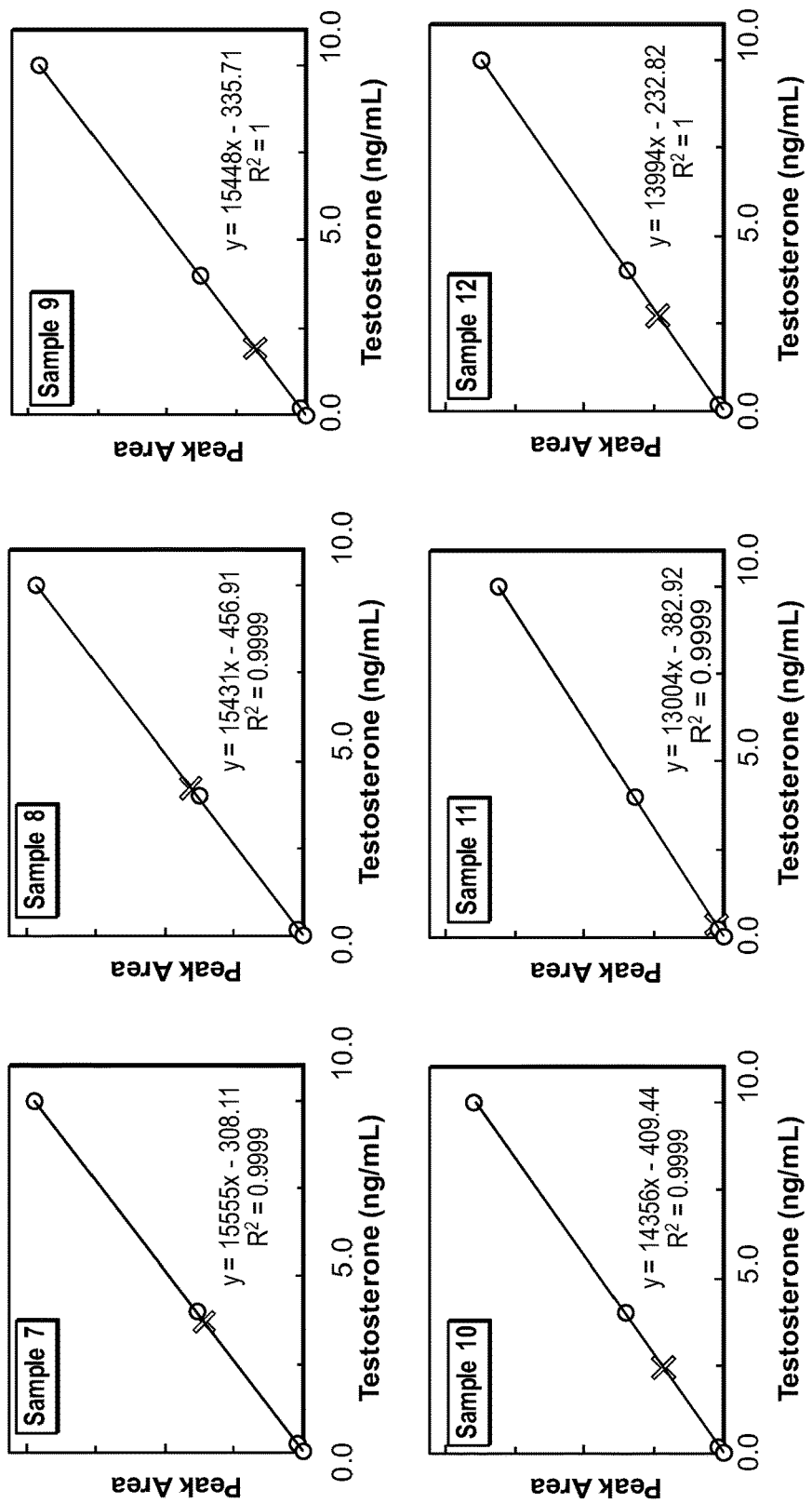
Figure 8C:
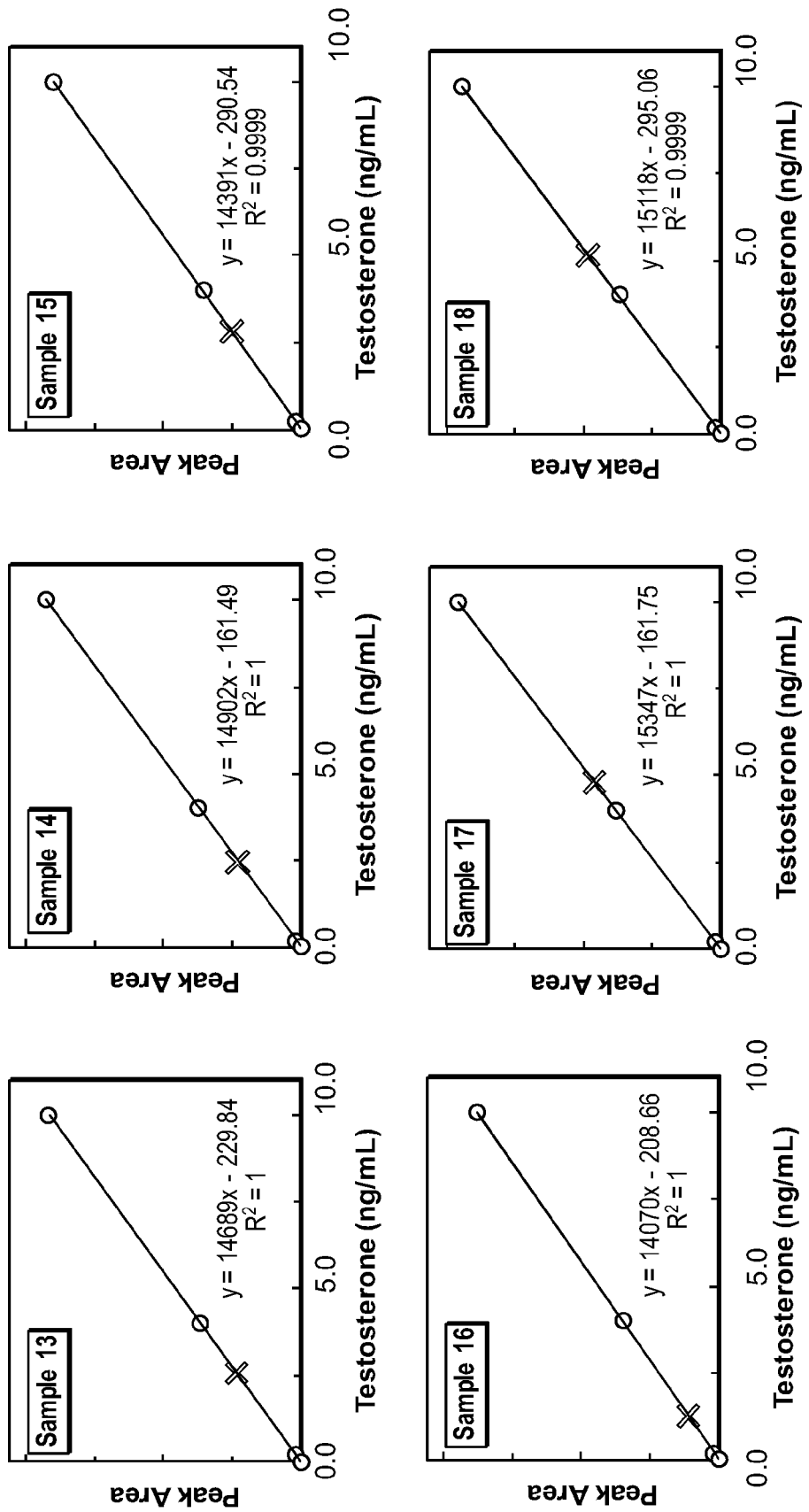
Figure 8D:
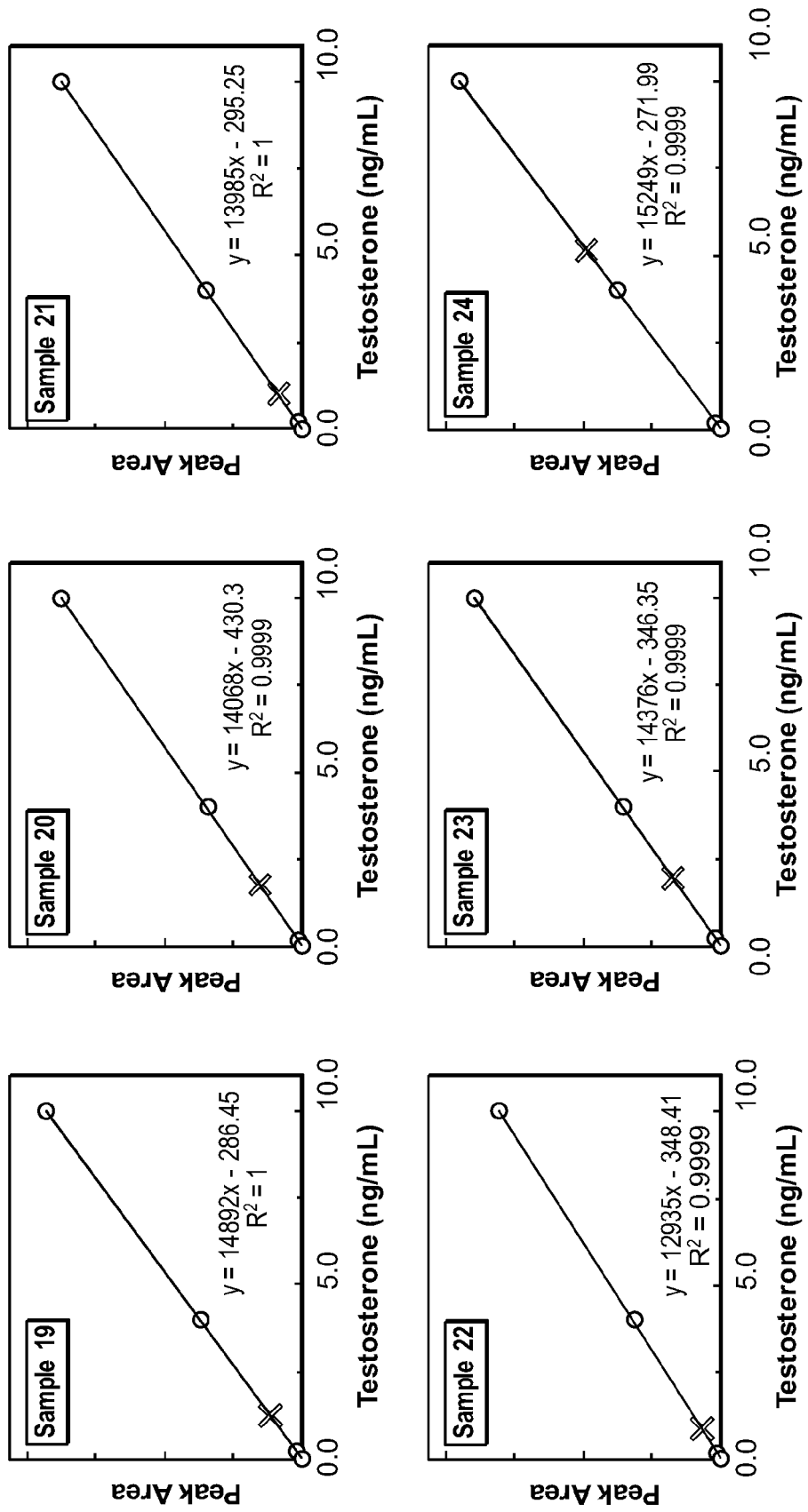
Figure 8E:
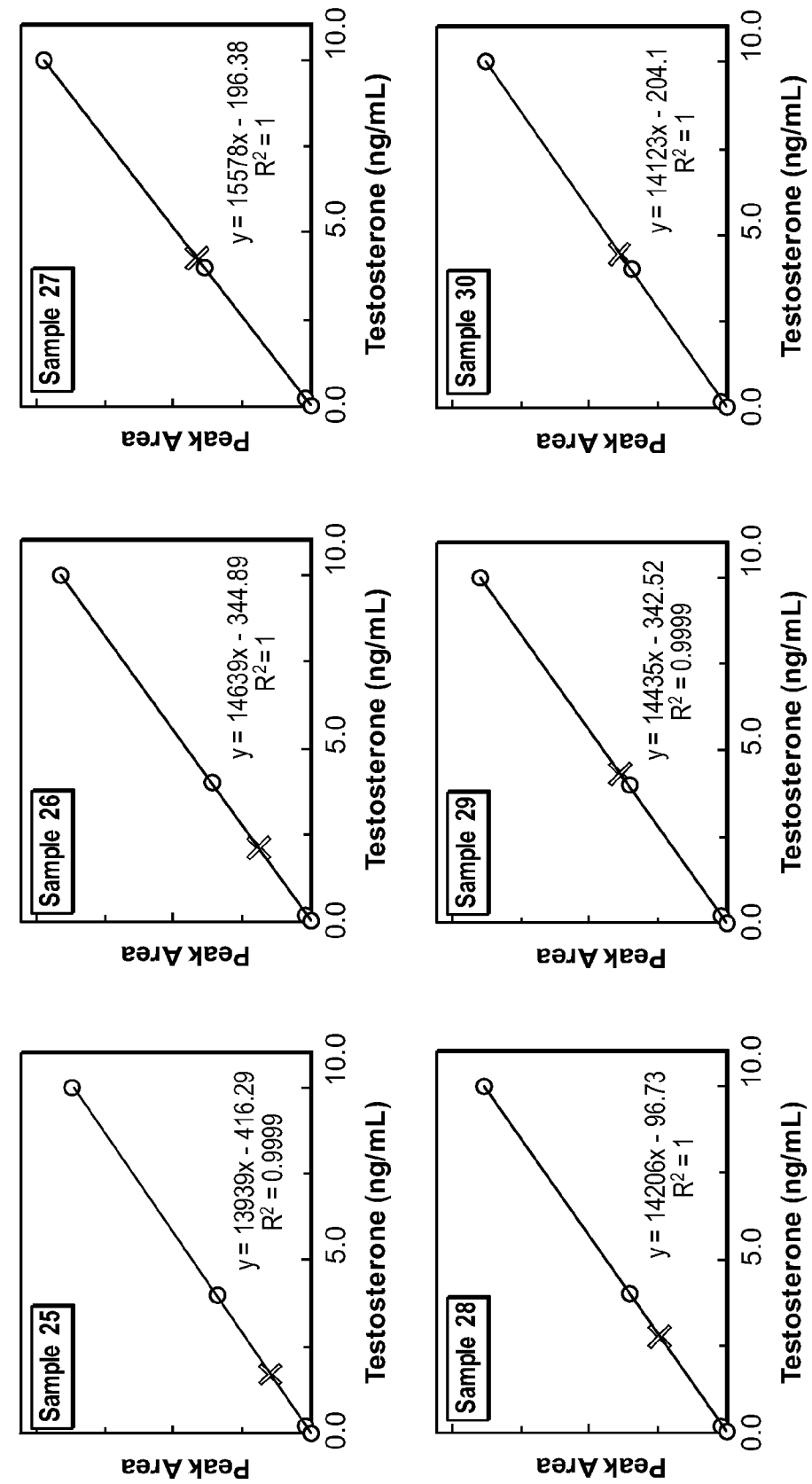
Figure 8F:
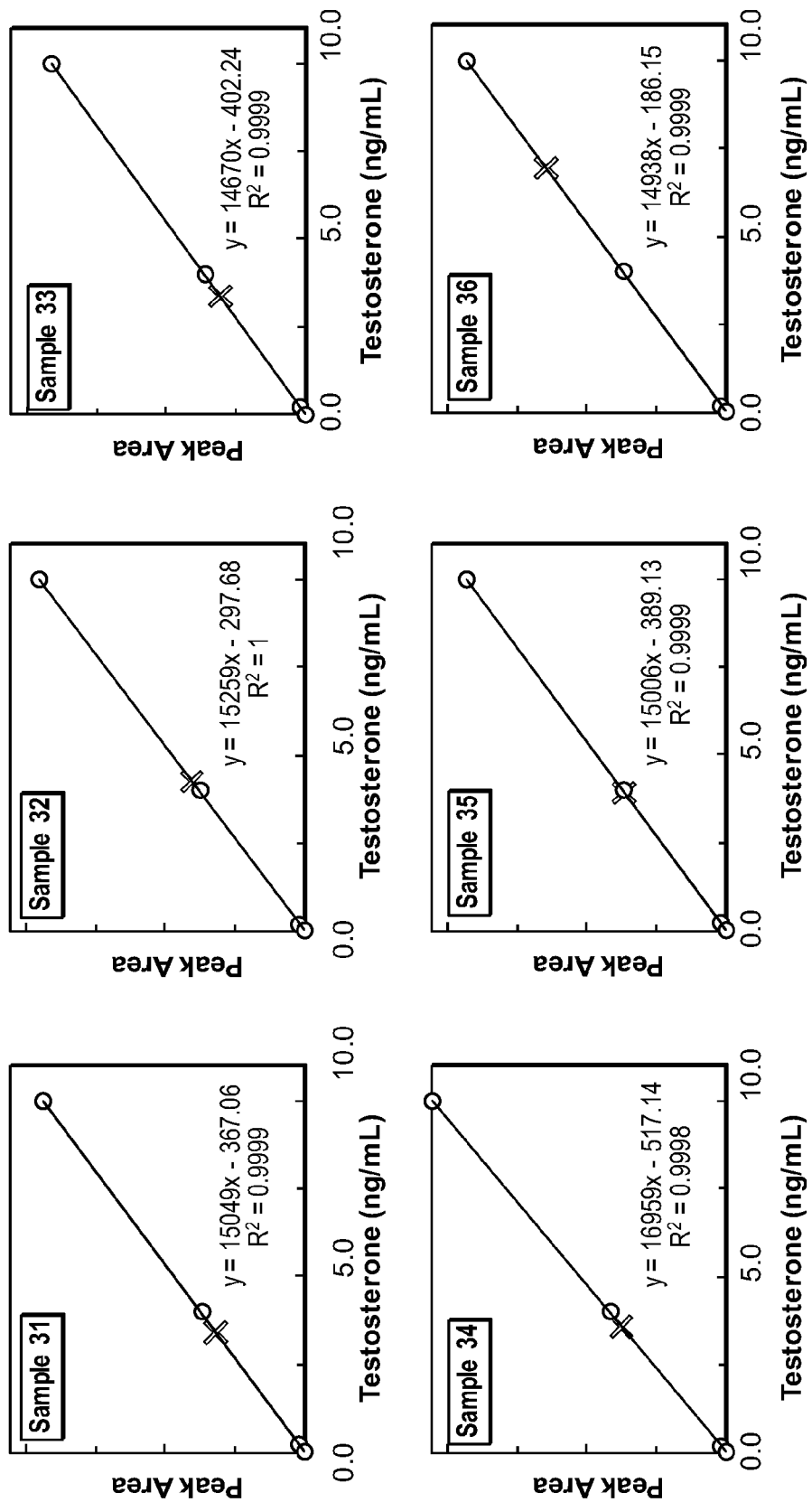
Figure 8G:
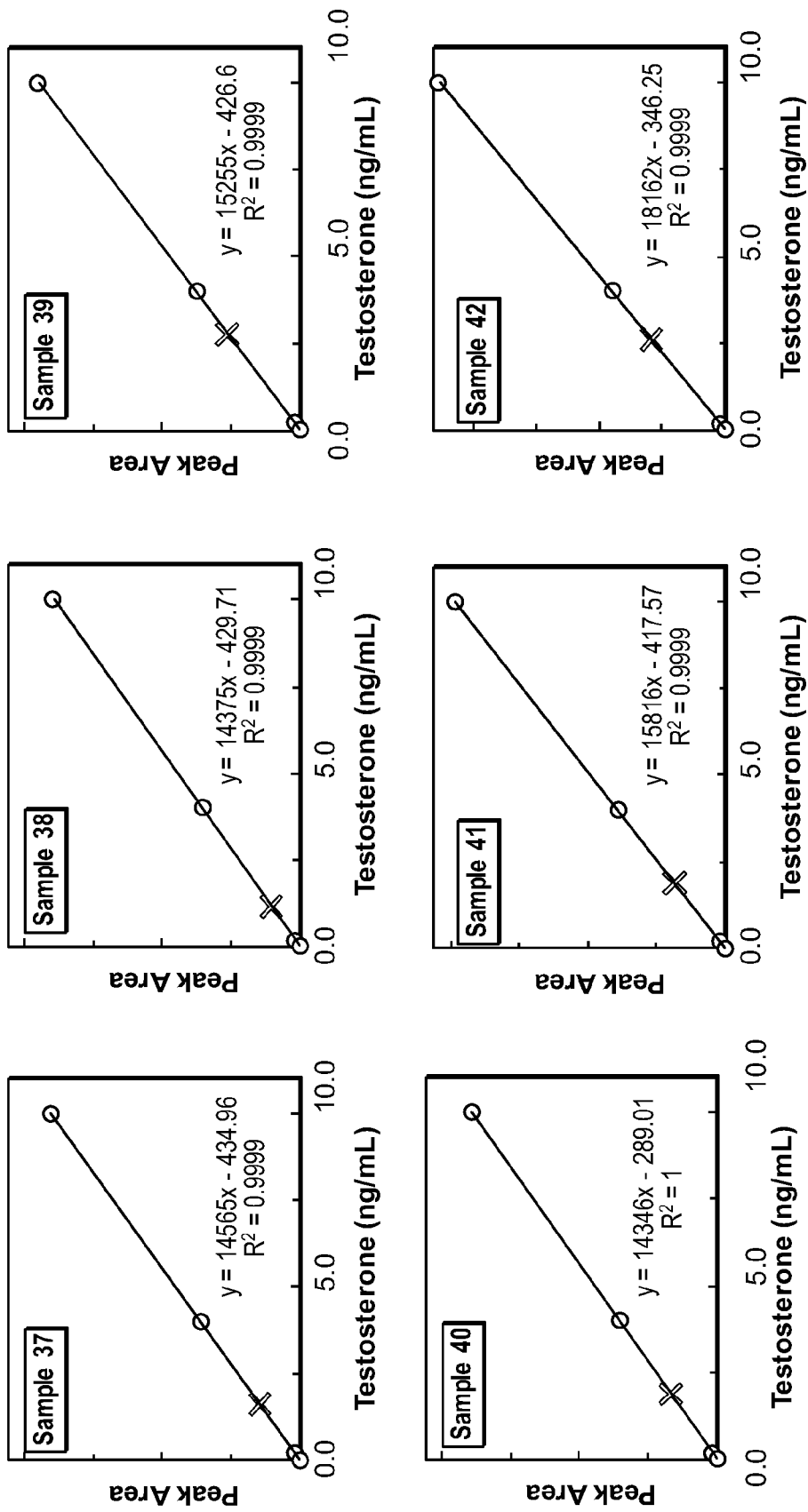
Figure 8H:
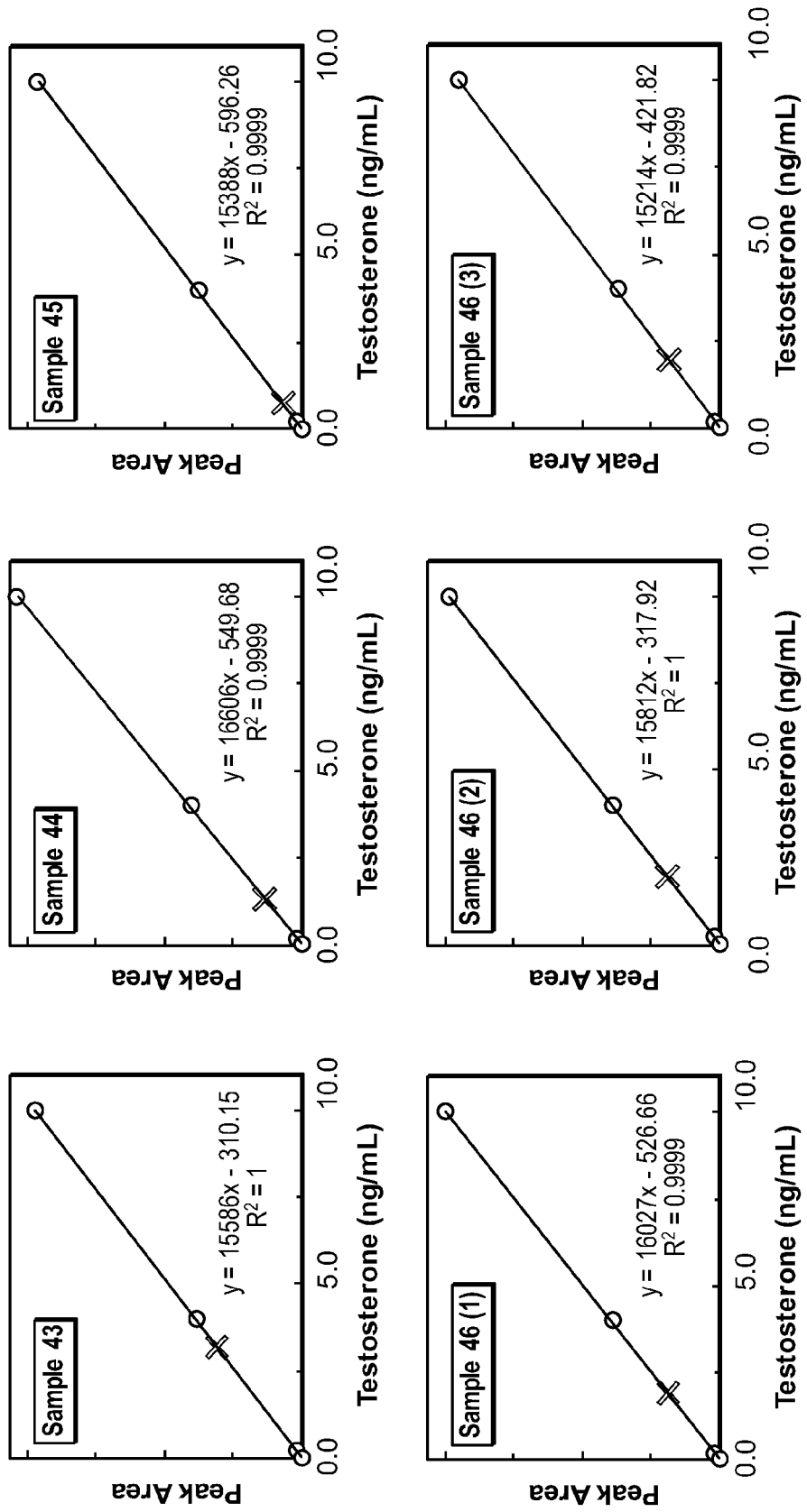
Figure 8I:
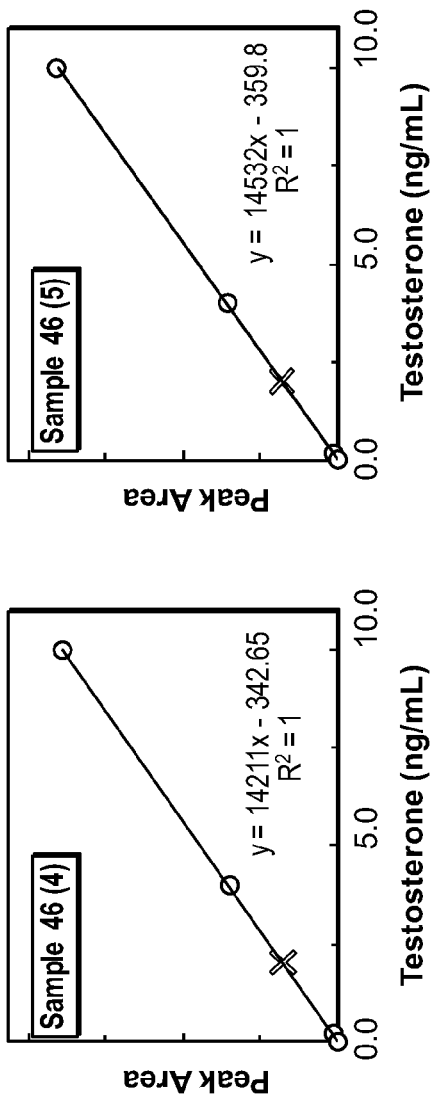

Conventional (External Calibration) Assay:

The single external calibration line generated by TargetLynx software and constructed from the responses of the six separate calibrators is shown in FIG. 7. Each point on the calibration line represents a separate UPLC/MS/MS analysis. This calibration line was used by TargetLynx to automatically calculate the testosterone concentration in each of the 46 serum samples based on the observed MS/MS responses. The results were exported from TargetLynx and are summarized in Table 5.

Figure 6:
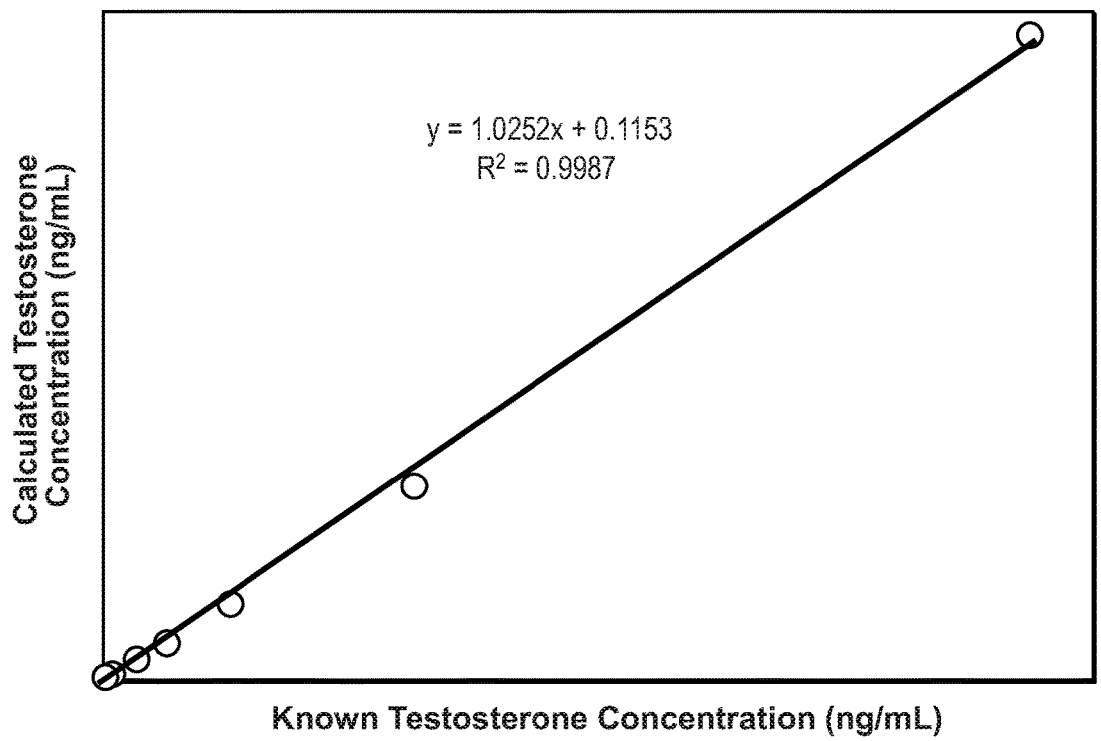
FIG. 6 shows a comparison of the testosterone QC values measured using the internal calibration method and known testosterone concentrations.

FIG. 6 shows a comparison of the testosterone QC values measured using the internal calibration method (Y axis) with the known testosterone concentrations (X-axis).

FIG. 7 shows an external calibration line for testosterone generated by TargetLynx. The calibration line is based on the analysis of six separate calibrators prepared in blank matrix at concentrations ranging from 0.1 ng/mL to 15 ng/mL.

Table 5 shows the analysis of 46 serum samples for testosterone concentration using conventional external calibration. The data were exported from TargetLynx. The last column indicates the calculated testosterone concentration for each sample.

Internal Calibration Assay:

TargetLynx was used to perform peak area integration for each of the four MRM chromatograms collected for each analyte. Those data were exported into Microsoft Excel where for each individual sample, the LINEST function was used to calculate the equation and coefficient of determination ($r^2$) of the regression line for the integrated peak area plotted (y axis) against the assigned concentration for the three internal calibrators (x axis). Linear regression analysis was performed in two ways; either including or excluding the origin (0,0). For each sample, the concentration of testosterone was calculated using the equation of the regression line and the integrated peak area for testosterone. The data are summarized in Table 6 and Table 7 below.

TABLE 5

Analysis of 46 serum samples for testosterone concentration.

| Analysis # | Sample | | Type | Peak Area T | Peak Area T-d3 | Response (T/T-d3) | Concentration (ng/mL) |
|---|---|---|---|---|---|---|---|
| 1 | Cal 0 | 0 ng/mL | Standard | | 10758 | — | — |
| 2 | Cal 1 | 0.1 ng/mL | Standard | 1438 | 12363 | 0.116 | 0.11 |
| 3 | Cal 2 | 0.5 ng/mL | Standard | 7803 | 13008 | 0.600 | 0.52 |
| 4 | Cal 3 | 1.0 ng/mL | Standard | 14002 | 12937 | 1.082 | 0.93 |
| 5 | Cal 4 | 2.0 ng/mL | Standard | 28521 | 13093 | 2.178 | 1.86 |
| 6 | Cal 5 | 5.0 ng/mL | Standard | 76503 | 14028 | 5.454 | 4.65 |
| 7 | Cal 6 | 15.0 ng/mL | Standard | 257188 | 14114 | 18.222 | 15.53 |
| 8 | External_Sample 1 | | Analyte | 52444 | 10981 | 4.776 | 4.08 |
| 9 | External_Sample 2 | | Analyte | 33233 | 10307 | 3.224 | 2.75 |
| 10 | External_Sample 3 | | Analyte | 67068 | 10637 | 6.305 | 5.38 |
| 11 | External_Sample 4 | | Analyte | 31308 | 10565 | 2.963 | 2.53 |
| 12 | External_Sample 5 | | Analyte | 25360 | 9414 | 2.694 | 2.30 |
| 13 | External_Sample 6 | | Analyte | 34690 | 9727 | 3.567 | 3.05 |
| 14 | External_Sample 7 | | Analyte | 46493 | 10161 | 4.576 | 3.90 |
| 15 | External_Sample 8 | | Analyte | 57583 | 10331 | 5.574 | 4.76 |
| 16 | External_Sample 9 | | Analyte | 25424 | 10078 | 2.523 | 2.16 |
| 17 | External_Sample 10 | | Analyte | 32847 | 10144 | 3.238 | 2.77 |
| 18 | External_Sample 11 | | Analyte | 3628 | 9906 | 0.366 | 0.32 |
| 19 | External_Sample 12 | | Analyte | 28662 | 8636 | 3.319 | 2.83 |
| 20 | External_Sample 13 | | Analyte | 29846 | 9605 | 3.107 | 2.65 |
| 21 | External_Sample 14 | | Analyte | 33345 | 10686 | 3.121 | 2.67 |
| 22 | External_Sample 15 | | Analyte | 32246 | 8956 | 3.601 | 3.07 |
| 23 | External_Sample 16 | | Analyte | 14747 | 10181 | 1.449 | 1.24 |
| 24 | External_Sample 17 | | Analyte | 66741 | 11736 | 5.687 | 4.85 |
| 25 | External_Sample 18 | | Analyte | 71037 | 11826 | 6.007 | 5.12 |
| 26 | External_Sample 19 | | Analyte | 17186 | 12000 | 1.432 | 1.23 |
| 27 | External_Sample 20 | | Analyte | 21911 | 10412 | 2.104 | 1.80 |
| 28 | External_Sample 21 | | Analyte | 11530 | 10123 | 1.139 | 0.98 |
| 29 | External_Sample 22 | | Analyte | 10790 | 10808 | 0.998 | 0.86 |
| 30 | External_Sample 23 | | Analyte | 24205 | 10394 | 2.329 | 1.99 |
| 31 | External_Sample 24 | | Analyte | 75310 | 11740 | 6.415 | 5.47 |
| 32 | External_Sample 25 | | Analyte | 20008 | 9042 | 2.213 | 1.89 |
| 33 | External_Sample 26 | | Analyte | 29700 | 12424 | 2.391 | 2.04 |
| 34 | External_Sample 27 | | Analyte | 51347 | 10503 | 4.889 | 4.17 |
| 35 | External_Sample 28 | | Analyte | 41719 | 12411 | 3.362 | 2.87 |
| 36 | External_Sample 29 | | Analyte | 59529 | 11364 | 5.239 | 4.47 |
| 37 | External_Sample 30 | | Analyte | 68204 | 12536 | 5.441 | 4.64 |
| 38 | External_Sample 31 | | Analyte | 47499 | 11972 | 3.967 | 3.39 |
| 39 | External_Sample 32 | | Analyte | 60855 | 11975 | 5.082 | 4.34 |
| 40 | External_Sample 33 | | Analyte | 40897 | 10423 | 3.923 | 3.35 |
| 41 | External_Sample 34 | | Analyte | 53013 | 12730 | 4.165 | 3.55 |
| 42 | External_Sample 35 | | Analyte | 59497 | 12772 | 4.658 | 3.98 |
| 43 | External_Sample 36 | | Analyte | 93720 | 11365 | 8.247 | 7.03 |
| 44 | External_Sample 37 | | Analyte | 22035 | 11639 | 1.893 | 1.62 |
| 45 | External_Sample 38 | | Analyte | 16112 | 12470 | 1.292 | 1.11 |
| 46 | External_Sample 39 | | Analyte | 42502 | 13156 | 3.231 | 2.76 |
| 47 | External_Sample 40 | | Analyte | 26952 | 12626 | 2.135 | 1.83 |
| 48 | External_Sample 41 | | Analyte | 26932 | 12831 | 2.099 | 1.80 |
| 49 | External_Sample 42 | | Analyte | 42089 | 12927 | 3.256 | 2.78 |
| 50 | External_Sample 43 | | Analyte | 46675 | 12277 | 3.802 | 3.25 |
| 51 | External_Sample 44 | | Analyte | 20167 | 11912 | 1.693 | 1.45 |
| 52 | External_Sample 45 | | Analyte | 10417 | 11832 | 0.880 | 0.76 |
| 53 | External_Sample 46 | | Analyte | 26672 | 10933 | 2.440 | 2.09 |

Table 6 shows the results and regression analysis for 46 serum samples analyzed using the Internal Calibration method. Five separate aliquots of sample 46 were analyzed (T=testosterone).

TABLE 6

Results and regression analysis for 46 serum samples analyzed using the Internal Calibration method.

| | | Integrated Peak Area | | | | Regression Analysis | | | Result |
|---|---|---|---|---|---|---|---|---|---|
| | | Cal 1 | Cal 2 | Cal 3 | | | | | T |
| Sample | Blank | (0.2 ng/mL) | (4.0 ng/mL) | (10.0 ng/mL) | T | Slope | Intercept | $r^2$ | (ng/mL) |
| 1 | 0 | 2910.3 | 60789.3 | 154545.4 | 59352.7 | 15456.7 | −310.03 | 1.0000 | 3.86 |
| 2 | 0 | 3048.1 | 63983.3 | 163458.1 | 42044.5 | 16347.5 | −411.22 | 0.9999 | 2.60 |
| 3 | 0 | 2990.5 | 60261.2 | 154974.4 | 79112.5 | 15491.1 | −437.05 | 0.9999 | 5.14 |
| 4 | 0 | 2831.5 | 58973.6 | 150099.7 | 37758.7 | 15011.4 | −314.15 | 0.9999 | 2.54 |
| 5 | 0 | 2581.3 | 56130.0 | 142605.0 | 29405.4 | 14268.1 | −322.57 | 1.0000 | 2.08 |
| 6 | 0 | 2581.5 | 57180.0 | 144969.6 | 42749.2 | 14507.6 | −319.37 | 1.0000 | 2.97 |
| 7 | 0 | 2979.9 | 61108.8 | 155558.4 | 57255.9 | 15554.9 | −308.11 | 0.9999 | 3.70 |
| 8 | 0 | 2942.5 | 59994.6 | 154357.6 | 65031.0 | 15431.1 | −456.91 | 0.9999 | 4.24 |
| 9 | 0 | 2848.5 | 60740.1 | 154423.1 | 29291.5 | 15447.5 | −335.71 | 1.0000 | 1.92 |
| 10 | 0 | 2615.1 | 56081.2 | 143519.3 | 34813.6 | 14355.9 | −409.44 | 0.9999 | 2.45 |
| 11 | 0 | 2237.3 | 50961.9 | 129921.7 | 4154.0 | 13003.7 | −382.92 | 0.9999 | 0.35 |
| 12 | 0 | 2694.6 | 55145.4 | 139944.5 | 37805.0 | 13994.1 | −232.82 | 1.0000 | 2.72 |
| 13 | 0 | 2742.8 | 58087.0 | 146837.1 | 37188.1 | 14689.2 | −229.84 | 1.0000 | 2.55 |
| 14 | 0 | 2792.3 | 59220.7 | 148949.1 | 36537.5 | 14902.0 | −161.49 | 1.0000 | 2.46 |
| 15 | 0 | 2762.0 | 56504.9 | 143924.5 | 40006.7 | 14391.1 | −290.54 | 0.9999 | 2.80 |
| 16 | 0 | 2576.7 | 55770.4 | 140612.3 | 17635.2 | 14070.0 | −208.66 | 1.0000 | 1.27 |
| 17 | 0 | 3096.9 | 60648.4 | 153537.8 | 73659.0 | 15347.2 | −161.75 | 1.0000 | 4.81 |
| 18 | 0 | 2909.8 | 59390.6 | 151199.8 | 77475.0 | 15118.3 | −295.06 | 0.9999 | 5.14 |
| 19 | 0 | 2668.5 | 58842.7 | 148810.1 | 18207.9 | 14892.0 | −286.45 | 1.0000 | 1.24 |
| 20 | 0 | 2427.8 | 55050.7 | 140562.0 | 24641.9 | 14067.7 | −430.30 | 0.9999 | 1.78 |
| 21 | 0 | 2466.5 | 55212.1 | 139733.3 | 13658.7 | 13985.4 | −295.25 | 1.0000 | 1.00 |
| 22 | 0 | 2295.8 | 50719.2 | 129274.0 | 11037.5 | 12935.4 | −348.41 | 0.9999 | 0.88 |
| 23 | 0 | 2634.0 | 56409.2 | 143712.5 | 27671.4 | 14376.1 | −346.35 | 0.9999 | 1.95 |
| 24 | 0 | 3037.3 | 59844.9 | 152559.2 | 78276.4 | 15248.5 | −271.99 | 0.9999 | 5.15 |
| 25 | 0 | 2530.6 | 54386.0 | 139352.0 | 23378.9 | 13939.0 | −416.29 | 0.9999 | 1.71 |
| 26 | 0 | 2661.7 | 57507.4 | 146324.7 | 30425.2 | 14639.0 | −344.89 | 1.0000 | 2.10 |
| 27 | 0 | 3038.1 | 61595.2 | 155792.3 | 66361.3 | 15578.2 | −196.38 | 1.0000 | 4.27 |
| 28 | 0 | 2587.6 | 56824.2 | 141932.8 | 39135.0 | 14206.4 | −96.73 | 1.0000 | 2.76 |
| 29 | 0 | 2779.6 | 56441.4 | 144382.1 | 61972.8 | 14434.7 | −342.52 | 0.9999 | 4.32 |
| 30 | 0 | 2796.3 | 55662.5 | 141277.7 | 62626.7 | 14123.4 | −204.10 | 1.0000 | 4.45 |
| 31 | 0 | 2863.1 | 58858.8 | 150510.6 | 51069.8 | 15049.3 | −367.06 | 0.9999 | 3.42 |
| 32 | 0 | 2845.9 | 60093.0 | 152550.4 | 64754.1 | 15259.1 | −297.68 | 1.0000 | 4.26 |
| 33 | 0 | 2829.4 | 57122.1 | 146756.5 | 48981.5 | 14670.2 | −402.24 | 0.9999 | 3.37 |
| 34 | 0 | 3310.2 | 65746.1 | 169694.6 | 60244.8 | 16959.1 | −517.14 | 0.9998 | 3.58 |
| 35 | 0 | 2813.6 | 58655.4 | 150053.7 | 58417.6 | 15005.6 | −389.13 | 0.9999 | 3.92 |
| 36 | 0 | 3078.5 | 58802.7 | 149492.6 | 103639.7 | 14937.9 | −186.15 | 0.9999 | 6.95 |
| 37 | 0 | 2507.9 | 57050.3 | 145521.5 | 22878.9 | 14564.8 | −434.96 | 0.9999 | 1.60 |
| 38 | 0 | 2584.7 | 56128.1 | 143698.8 | 16407.7 | 14375.4 | −429.71 | 0.9999 | 1.17 |
| 39 | 0 | 2826.8 | 59551.2 | 152534.6 | 41862.6 | 15254.9 | −426.60 | 0.9999 | 2.77 |
| 40 | 0 | 2576.7 | 56619.4 | 143362.6 | 26615.8 | 14346.1 | −289.01 | 1.0000 | 1.88 |
| 41 | 0 | 2866.2 | 61952.2 | 158094.2 | 29469.5 | 15815.7 | −417.57 | 0.9999 | 1.89 |
| 42 | 0 | 3503.1 | 71372.3 | 181646.4 | 47029.0 | 18162.4 | −346.25 | 0.9999 | 2.61 |
| 43 | 0 | 2943.7 | 61292.9 | 155841.3 | 49608.0 | 15585.8 | −310.15 | 1.0000 | 3.20 |
| 44 | 0 | 2905.3 | 64740.3 | 165963.2 | 21534.3 | 16606.2 | −549.68 | 0.9999 | 1.33 |
| 45 | 0 | 2626.8 | 59722.4 | 153768.9 | 10903.6 | 15387.5 | −596.26 | 0.9999 | 0.75 |
| 46(1) | 0 | 2938.8 | 62277.8 | 160256.8 | 29995.9 | 16026.8 | −526.66 | 0.9999 | 1.90 |
| 46(2) | 0 | 2970.5 | 62195.5 | 158096.4 | 30541.1 | 15812.3 | −317.92 | 1.0000 | 1.95 |
| 46(3) | 0 | 2757.0 | 59508.2 | 152083.6 | 29596.5 | 15213.8 | −421.82 | 0.9999 | 1.97 |
| 46(4) | 0 | 2535.6 | 55870.0 | 142015.4 | 28400.6 | 14210.7 | −342.65 | 1.0000 | 2.02 |
| 46(5) | 0 | 2540.1 | 57177.2 | 145191.4 | 28763.4 | 14531.5 | −359.80 | 1.0000 | 2.00 |

Table 7 shows the results and regression analysis for 46 serum samples analyzed using the Internal Calibration method with the origin excluded. Five separate aliquots of sample 46 were analyzed (T=testosterone).

represent the three internal calibrators plus origin that were used to construct a linear regression line. The cross represents the peak area for testosterone in that sample and the corresponding concentration.

TABLE 7

Results and regression analysis for 46 serum samples analyzed using the Internal Calibration method with the origin excluded.

| | Integrated Peak Area | | | | Regression Analysis | | | Result |
|---|---|---|---|---|---|---|---|---|
| | Cal 1 | Cal 2 | Cal 3 | | | | | T |
| Sample | (0.2 ng/mL) | (4.0 ng/mL) | (10.0 ng/mL) | T | Slope | Intercept | $r^2$ | (ng/mL) |
| 1 | 2910.3 | 60789.3 | 154545.4 | 59352.7 | 15486.8 | −555.64 | 1.0000 | 3.87 |
| 2 | 3048.1 | 63983.3 | 163458.1 | 42044.5 | 16387.4 | −736.99 | 0.9999 | 2.61 |
| 3 | 2990.5 | 60261.2 | 154974.4 | 79112.5 | 15533.5 | −783.27 | 0.9998 | 5.14 |
| 4 | 2831.5 | 58973.6 | 150099.7 | 37758.7 | 15041.8 | −563.02 | 0.9999 | 2.55 |
| 5 | 2581.3 | 56130.0 | 142605.0 | 29405.4 | 14299.3 | −578.11 | 1.0000 | 2.10 |
| 6 | 2581.5 | 57180.0 | 144969.6 | 42749.2 | 14538.6 | −572.38 | 1.0000 | 2.98 |
| 7 | 2979.9 | 61108.8 | 155558.4 | 57255.9 | 15584.8 | −552.19 | 0.9999 | 3.71 |
| 8 | 2942.5 | 59994.6 | 154357.6 | 65031.0 | 15475.4 | −818.87 | 0.9998 | 4.26 |
| 9 | 2848.5 | 60740.1 | 154423.1 | 29291.5 | 15480.1 | −601.66 | 1.0000 | 1.93 |
| 10 | 2615.1 | 56081.2 | 143519.3 | 34813.6 | 14395.6 | −733.79 | 0.9999 | 2.47 |
| 11 | 2237.3 | 50961.9 | 129921.7 | 4154.0 | 13040.8 | −686.27 | 1.0000 | 0.37 |
| 12 | 2694.6 | 55145.4 | 139944.5 | 37805.0 | 14016.6 | −417.27 | 1.0000 | 2.73 |
| 13 | 2742.8 | 58087.0 | 146837.1 | 37188.1 | 14711.5 | −411.91 | 1.0000 | 2.56 |
| 14 | 2792.3 | 59220.7 | 148949.1 | 36537.5 | 14917.6 | −289.42 | 1.0000 | 2.47 |
| 15 | 2762.0 | 56504.9 | 143924.5 | 40006.7 | 14419.3 | −520.70 | 0.9999 | 2.81 |
| 16 | 2576.7 | 55770.4 | 140612.3 | 17635.2 | 14090.2 | −373.95 | 1.0000 | 1.28 |
| 17 | 3096.9 | 60648.4 | 153537.8 | 73659.0 | 15362.9 | −289.89 | 1.0000 | 4.81 |
| 18 | 2909.8 | 59390.6 | 151199.8 | 77475.0 | 15146.9 | −528.80 | 0.9999 | 5.15 |
| 19 | 2668.5 | 58842.7 | 148810.1 | 18207.9 | 14919.8 | −513.38 | 1.0000 | 1.25 |
| 20 | 2427.8 | 55050.7 | 140562.0 | 24641.9 | 14109.4 | −771.17 | 0.9999 | 1.80 |
| 21 | 2466.5 | 55212.1 | 139733.3 | 13658.7 | 14014.0 | −529.14 | 1.0000 | 1.01 |
| 22 | 2295.8 | 50719.2 | 129274.0 | 11037.5 | 12969.2 | −624.41 | 0.9999 | 0.90 |
| 23 | 2634.0 | 56409.2 | 143712.5 | 27671.4 | 14409.7 | −620.72 | 0.9999 | 1.96 |
| 24 | 3037.3 | 59844.9 | 152559.2 | 78276.4 | 15274.9 | −487.47 | 0.9999 | 5.16 |
| 25 | 2530.6 | 54386.0 | 139352.0 | 23378.9 | 13979.4 | −746.06 | 0.9999 | 1.73 |
| 26 | 2661.7 | 57507.4 | 146324.7 | 30425.2 | 14672.4 | −618.11 | 1.0000 | 2.12 |
| 27 | 3038.1 | 61595.2 | 155792.3 | 66361.3 | 15597.3 | −351.96 | 1.0000 | 4.28 |
| 28 | 2587.6 | 56824.2 | 141932.8 | 39135.0 | 14215.8 | −173.36 | 1.0000 | 2.77 |
| 29 | 2779.6 | 56441.4 | 144382.1 | 61972.8 | 14467.9 | −613.87 | 0.9999 | 4.33 |
| 30 | 2796.3 | 55662.5 | 141277.7 | 62626.7 | 14143.2 | −365.78 | 1.0000 | 4.45 |
| 31 | 2863.1 | 58858.8 | 150510.6 | 51069.8 | 15084.7 | −657.84 | 0.9999 | 3.43 |
| 32 | 2845.9 | 60093.0 | 152550.4 | 64754.1 | 15288.0 | −533.49 | 1.0000 | 4.27 |
| 33 | 2829.4 | 57122.1 | 146756.5 | 48981.5 | 14709.2 | −720.90 | 0.9999 | 3.38 |
| 34 | 3310.2 | 65746.1 | 169694.6 | 60244.8 | 17009.3 | −926.82 | 0.9998 | 3.60 |
| 35 | 2813.6 | 58655.4 | 150053.7 | 58417.6 | 15043.3 | −697.39 | 0.9999 | 3.93 |
| 36 | 3078.5 | 58802.7 | 149492.6 | 103639.7 | 14956.0 | −333.62 | 0.9999 | 6.95 |
| 37 | 2507.9 | 57050.3 | 145521.5 | 22878.9 | 14606.9 | −779.52 | 0.9999 | 1.62 |
| 38 | 2584.7 | 56128.1 | 143698.8 | 16407.7 | 14417.0 | −770.12 | 0.9999 | 1.19 |
| 39 | 2826.8 | 59551.2 | 152534.6 | 41862.6 | 15296.2 | −764.54 | 0.9999 | 2.79 |
| 40 | 2576.7 | 56619.4 | 143362.6 | 26615.8 | 14374.1 | −517.97 | 1.0000 | 1.89 |
| 41 | 2866.2 | 61952.2 | 158094.2 | 29469.5 | 15856.2 | −748.36 | 0.9999 | 1.91 |
| 42 | 3503.1 | 71372.3 | 181646.4 | 47029.0 | 18196.0 | −620.55 | 0.9999 | 2.62 |
| 43 | 2943.7 | 61292.9 | 155841.3 | 49608.0 | 15615.9 | −555.85 | 1.0000 | 3.21 |
| 44 | 2905.3 | 64740.3 | 165963.2 | 21534.3 | 16659.5 | −985.14 | 0.9999 | 1.35 |
| 45 | 2626.8 | 59722.4 | 153768.9 | 10903.6 | 15445.3 | −1068.62 | 0.9999 | 0.78 |
| 46(1) | 2938.8 | 62277.8 | 160256.8 | 29995.9 | 16077.8 | −943.87 | 0.9999 | 1.92 |
| 46(2) | 2970.5 | 62195.5 | 158096.4 | 30541.1 | 15843.1 | −569.77 | 1.0000 | 1.96 |
| 46(3) | 2757.0 | 59508.2 | 152083.6 | 29596.5 | 15254.7 | −755.98 | 0.9999 | 1.99 |
| 46(4) | 2535.6 | 55870.0 | 142015.4 | 28400.6 | 14243.9 | −614.10 | 1.0000 | 2.04 |
| 46(5) | 2540.1 | 57177.2 | 145191.4 | 28763.4 | 14566.4 | −644.83 | 1.0000 | 2.02 |

The individual internal calibration lines for each of the 50 analyses (45 samples plus five replicates of sample 46) are shown in FIG. 8A-8I. The slopes of the various internal calibration lines vary between the different samples, potentially as a result of differences in the matrix that result in differences in recovery and differences in ion suppression. FIG. 8A-8I illustrates how the invention provides for an individual calibration for each target analyte in each sample.

FIG. 9 shows individual internal calibration lines for serum samples 22 and 42 that correspond to the minimum and maximum slopes observed (40% difference). The circles Comparison of Results:

The results obtained using the Internal Calibration method (either including the origin or excluding the origin from the regression analysis) were compared to the results obtained using conventional calibration by linear regression analysis (FIG. 10 and FIG. 11).

FIG. 10 shows a comparison of testosterone concentrations determined in 46 serum samples using external calibration and internal calibration with three internal calibrators. FIG. 11 shows a comparison of testosterone concentrations determined in 46 serum samples using external calibration and internal calibration with three internal calibrators plus the origin. Both comparisons (FIG. 10 and FIG. 11) show excellent agreement with $r^2>0.99$ and with slopes close to unity. The slopes are both >0.96 suggesting an average difference of less than 4% when using the internal calibration method versus the conventional external calibration method.

Estimation of Imprecision:

To estimate within-day precision for the Internal Calibration assay, five separate aliquots of a pooled serum sample (sample 46) were analyzed. The results are shown in Table 8 and indicate that imprecision was <3% at a testosterone concentration of approximately 2 ng/mL.

TABLE 8

Within-day imprecision estimate for the Internal Calibration assay either including or excluding the origin when performing regression analysis of the calibration data.

| | Testosterone Concentration by Internal Calibration (ng/mL) | |
|---|---|---|
| Analysis # | Including Origin | Excluding Origin |
| 1 | 1.90 | 1.92 |
| 2 | 1.95 | 1.96 |
| 3 | 1.97 | 1.99 |
| 4 | 2.02 | 2.04 |
| 5 | 2.00 | 2.02 |
| Mean | 1.97 | 1.99 |
| SD | 0.04629 | 0.04469 |
| % CV | 2.35 | 2.25 |

Discussion

The internal calibrators used in this study demonstrate proof of principle and convenience (e.g., because they were available from commercial sources rather than requiring de novo synthesis) but, are not expected to represent the optimal attainable assay results (e.g., because the mass differences between testosterone, testosterone-d2, and testosterone-d3 were small and there was potential for isotopic interference). Ideally, internal calibrators would be designed with isotopic labels in sufficient quantity and with isotopic labels in specific locations such that there was essentially no interference between the analyte and the internal calibrators or between the internal calibrators. Furthermore, prior to synthesizing designed internal calibrators, the specific MRM transitions for the designed internal calibrators would be screened using matrix samples (e.g., human serum) to ensure that endogenous materials ordinarily present in matrix do not materially interfere with any of the designed internal calibrators.

Stable isotope labeled materials are typically manufactured in small quantities. Therefore, it can be difficult to precisely weigh accurate quantities of the stable isotope materials, to make accurate stock solutions that could be used to prepare internal calibrators. There is also a possibility that in some cases, the stable isotope labeled material can have slightly different ionization characteristics when compared to the unlabeled material. For at least these reasons it can be advantageous in various embodiments to assign concentration values to the internal calibrator stock solutions by comparison to the response obtained for the unlabeled material. In Example 1, internal calibrator concentrations were assigned by comparison to an in-house stock solution of unlabeled testosterone. Value assignment can be performed relative to a recognized international reference material, for example a Certified Reference Material (e.g., supplied by NIST) or other reference material that has metrological traceability to SI units. These steps can be used to ensure the accuracy of the internal calibration process.

As shown in Example 1, conventional calibration requires the analysis of 6 individual matrix calibrators, followed by the batch of samples to be analyzed. Such batch mode analysis is required to minimize potential calibration drift. Typically, a second batch of samples analyzed (using the conventional method) on the same day would require a new external calibration curve. With this conventional mode of operation, the time to first result is equivalent to the time taken for eight analytical runs (e.g., blank plus six calibrators plus the first sample). Using internal calibration, there is no requirement to run external calibrators, so the time to first result is potentially eight times faster than with external calibration (e.g., approximately 4 min versus approximately 32 min in Example 1). Freedom from batch mode of analysis allows for the first time random access and stat sample analysis by LC/MS/MS.

The results of Example 1 demonstrate that internal calibration using only three calibrators can provide results that differ by less than 4% on average from results obtained using conventional external calibration with six calibration points. The preliminary estimate of within-day imprecision was <3% demonstrating that the internal calibration assay is precise as well as accurate. The individual internal calibration lines show considerable variation between samples (e.g., up to 40% difference in the slope of the calibration line), potentially due to matrix effects, indicating that the internal calibrators are performing as intended. Further studies of the behavior of the internal calibrators under different conditions (e.g., different degrees of ion suppression, simulated poor recovery, simulated poor instrument performance, etc.) can be used to develop acceptance criteria for the slope of the internal calibration line such that poor quality data could be rejected.

Example 2: The Analysis of Sirolimus in Whole Blood Using Multipoint Calibration in a Single Analysis Introduction:

In this example, the invention was used to measure the concentration of the immunosuppressant drug sirolimus in whole blood. There is an external quality assurance scheme (the International Proficiency Testing [IPT] Scheme; http://www.bioanalytics.co.uk/Results2012.php) for this analyte. The IPT scheme provides three QA samples each month to participating laboratories. The laboratories report the results back to the scheme and the data are processed to determine the mean value for each QA sample and the limits for acceptable results based on the standard deviation of the data. The invention was used to quantify sirolimus in IPT samples and the acceptability of the results was determined based on the acceptance criteria published by the IPT Scheme. Two separate experiments were performed with different methods of adding the internal calibrators as described below. In addition, low, medium and high QC samples were prepared and analyzed in replicate to provide a preliminary evaluation of assay precision.

Methods

Internal Calibrator Selection:

Multiple labeled forms of sirolimus were not available and therefore compounds similar in structure (analogs) were therefore used as shown below. The MS/MS characteristics of the analyte and the internal calibrators were investigated and a specific MRM transition selected for each. The analyte and the selected internal calibrators could be distinguished from each other in a single LC/MS/MS analysis based on the selected MRM transitions.

TABLE 9

MS/MS Characteristics of Sirolimus and the selected internal calibrators.

| Analyte or Internal Calibrator | Type | MRM Transition |
|---|---|---|
| Sirolimus | Analyte | 931.5 > 864.5 |
| Everolimus | structural analog | 975.5 > 908.5 |
| Everolimus-d6 | deuterium labelled structural analog | 981.7 > 914.5 |
| 32-desmethoxyrapamycin | structural analog | 901.7 > 834.7 |

Internal Calibrator Relative Response ("Value Assignment"):

When using analog internal calibrators it is particularly important to account for any difference in the intensity of the MS/MS signal generated by the internal calibrator compared to the analyte. For example, differences can arise because of differences in behavior during sample preparation (extraction efficiency) or because of differences in behavior during analysis such as ionization efficiency, fragmentation characteristics, etc. The analyte and the three internal calibrators were spiked into acetonitrile:water (2:1, v:v), each at a final concentration of 10 ng/mL. Five replicates were prepared and analysed using UPLC/MS/MS (see below). The mean integrated peak areas for everolimus, d6-everolimus and 32-desmethoxyrapamycin were compared with the mean integrated peak area for sirolimus and the relative response factor was calculated where Relative Response Factor= (mean calibrator peak area)/(mean sirolimus peak area). The relative response factors were used to assign "analyte equivalent" concentration values to the internal calibrator stock solutions where: analyte equivalent concentration= (internal calibrator concentration)×(relative response factor). The relative response calculations are shown in Table 10 below.

TABLE 10

Determination of the Relative Response Factors for the analog internal standards.

| | Integrated Peak Area | | | |
|---|---|---|---|---|
| Analysis # | Sirolimus | Everolimus | Everolimus-d6 | 32-desmethoxy-rapamycin |
| 1 | 563.9 | 440.1 | 620.1 | 464.2 |
| 2 | 500.0 | 471.6 | 512.3 | 340.7 |
| 3 | 456.9 | 449.9 | 564.9 | 309.5 |
| 4 | 409.9 | 453 | 637.3 | 316.5 |
| 5 | 480.1 | 428.5 | 553.8 | 220.3 |
| Mean | 482.2 (A) | 448.6 (B) | 577.7 (C) | 330.2 (D) |
| SD | 56.71 | 16.02 | 50.90 | 87.69 |
| % CV | 11.8 | 3.6 | 8.8 | 26.6 |
| Relative Response | 1.00 | 0.93 (B/A) | 1.2 (C/A) | 0.68 (D/A) |

Sample Preparation
1. Place 50 μL of whole blood into an Eppendorf tube
2. Add 0.1 M zinc sulphate (200 μL) to each tube
3. Vortex mix
4. Add 500 μL acetonitrile
5. Centrifuge at 12,500 RPM for 5 min at 5° C.
6. Transfer 200 μL supernatant to a Waters Maximum Recovery vial and analyze by UPLC/MS/MS In Experiment 1, the acetonitrile in step 4 contained the internal calibrators everolimus (0.3 ng/mL), 32-desmethoxyrapamycin (3 ng/mL) and d6-everolimus (9 ng/mL). When the relative response factor and the ratio of sample (50 μL) to internal calibrator mix (500 μL) is taken into account, the internal calibrator concentrations were equivalent to sirolimus present in the sample at 2.7 ng/mL (everolimus), 21.0 ng/mL (32-desmethoxyrapamycin) and 108 ng/mL (everolimus-d6) respectively.

In Experiment 2, the internal calibrators were spiked directly into the sample at step 1. In this case the internal calibrator concentrations were equivalent to sirolimus present in the sample at approximately 1.65 ng/mL (everolimus), 17.5 ng/mL (everolimus-d6) and 22.1 ng/mL (32-desmethoxyrapamycin).

UPLC/MS/MS Analysis
Instrumentation:
A Waters® ACQUITY UPLC coupled to a Waters TQD mass spectrometer operated in electrospray positive ionisation mode and equipped with a Z-Spray ion source was used for all analyses. All aspects of system operation and data acquisition were controlled using MassLynx 4.1 software. Data processing (chromatographic peak area integration) was carried out using TargetLynx. Calculation of sirolimus concentrations in the test samples was by linear regression analysis of peak areas vs internal calibrator concentration using Microsoft Excel.

UPLC Condition:
Mobile phase A: Water with 2 mM ammonium acetate+0.1% formic acid
Mobile Phase B: Methanol with 2 mM ammonium acetate+ 0.1% formic acid
Weak wash solvent: Water, 1000 μL
Strong wash solvent: Methanol, 500 μL
Seal Wash: 20% aqueous methanol
Column: ACQUITY HSS C18 SB 2.1×30 mm 1.8 μm with pre-column filter
Column temp: 50° C.
Injection Vol: 37.5 μL (PLNO, 100 μL loop and 250 μL sample syringe fitted) 3 μL overfill, load ahead
Run time: 2.25 minutes
The UPLC conditions are given below by Table 11.

TABLE 11

Chromatographic conditions used for the analysis of sirolimus.

| Time (mins) | Flow (mL/min) | % A | % B | Curve |
|---|---|---|---|---|
| 0 | 0.4 | 50 | 50 | Initial |
| 0.45 | 0.4 | 50 | 50 | 1 |
| 0.85 | 0.4 | 0 | 100 | 6 |
| 1.25 | 1.0 | 0 | 100 | 6 |
| 1.50 | 0.4 | 50 | 50 | 11 |

TABLE 12

MS/MS conditions used for the analysis of sirolimus.

| Compound | Precursor (m/z) | Product (m/z) | Dwell (secs) | Cone (V) | Collision (eV) |
|---|---|---|---|---|---|
| 32-desmethoxyrapamycin | 901.7 | 834.7 | 0.04 | 20 | 20 |
| Sirolimus | 931.5 | 864.5 | 0.04 | 30 | 16 |
| Everolimus | 975.5 | 908.5 | 0.04 | 30 | 18 |
| Everolimus-d6 | 981.7 | 914.5 | 0.04 | 35 | 22 |

FIG. 12A-D shows an example mass chromatogram from Experiment 2 using the LC and MS/MS conditions described above.

Data Processing:

TargetLynx was used to perform peak area integration for each of the four MRM chromatograms collected for each sample. Those data were exported into Microsoft Excel where for each individual sample, the LINEST function was used to calculate the equation and coefficient of determination ($r^2$) of the regression line for the integrated peak area plotted (y axis) against the assigned concentration for the three internal calibrators (x axis). Linear regression analysis was performed in two ways; either including or excluding the origin (0,0). For each sample, the concentration of sirolimus was calculated using the equation of the regression line and the integrated peak area for sirolimus.

Results

Experiment 1:

Ten sirolimus IPT samples were analyzed using the methods described above. The internal calibrators spanned a concentration range from approximately 2 ng/mL to 100 ng/mL. The individual calibration lines constructed including the origin are shown in FIG. 13A-B. The regression parameters and calculated sirolimus concentrations are shown in Tables 13 and 14. For all ten samples, the calculated concentration of sirolimus was within the acceptable range of the IPT scheme (ie IPT Min≤Result≤IPT Max) whether calculated including or excluding the origin demonstrating that the internal calibration method provides acceptable results (Tables 13 and 14).

TABLE 13

Experiment 1: The sirolimus concentration in ten IPT samples determined using the three internal calibrators. The calculated results for all samples was in the acceptable range for the scheme (ie IPT Min ≤ Result ≤ IPT Max)

| | Integrated Peak Area | | | | Regression Analysis | | | Result | IPT | | |
|---|---|---|---|---|---|---|---|---|---|---|---|
| | Cal 1 | Cal 2 | Cal 3 | | | | | Sample | Mean | Min | Max |
| Sample | (2.7 ng/mL) | (21 ng/mL) | (108 ng/mL) | Sample | Slope | Intercept | $r^2$ | (ng/mL) | (ng/mL) | (ng/mL) | (ng/mL) |
| 151B | 117 | 488 | 2219 | 195 | 19.941 | 65.905 | 1.0000 | 6.47 | 8.9 | 4.7 | 13.1 |
| 149B | 86 | 433 | 2063 | 213 | 18.763 | 36.990 | 1.0000 | 9.38 | 11.7 | 7.2 | 16.2 |
| 153C | 90 | 469 | 1980 | 233 | 17.766 | 66.410 | 0.9993 | 9.38 | 11.9 | 6.8 | 17 |
| 148B | 85 | 461 | 2032 | 205 | 18.354 | 53.597 | 0.9996 | 8.25 | 11.7 | 7.2 | 16.2 |
| 153A | 85 | 453 | 1821 | 403 | 16.246 | 73.117 | 0.9985 | 20.31 | 20.1 | 12.6 | 27.6 |
| 148C | 88 | 494 | 1955 | 167 | 17.435 | 80.255 | 0.9980 | 4.98 | 5.8 | 3.1 | 8.5 |
| 150C | 85 | 460 | 1789 | 312 | 15.897 | 80.119 | 0.9977 | 14.59 | 17.7 | 10.8 | 24.6 |
| 157A | 99 | 458 | 1810 | 334 | 16.026 | 85.467 | 0.9986 | 15.51 | 19.1 | 11.9 | 26.3 |
| 157C | 78 | 452 | 1902 | 218 | 17.116 | 59.287 | 0.9990 | 9.27 | 9.1 | 5.2 | 13 |
| 155B | 95 | 489 | 2032 | 258 | 18.188 | 73.567 | 0.9991 | 10.14 | 13.7 | 8.3 | 19.1 |

TABLE 14

Experiment 1: The sirolimus concentration in ten IPT samples determined using the three internal calibrators plus the origin. The calculated results for all samples was in the acceptable range for the scheme (ie IPT Min ≤Result ≤ IPT Max)

| | Integrated Peak Area | | | | | Regression Analysis | | | Result | IPT | | |
|---|---|---|---|---|---|---|---|---|---|---|---|---|
| | | Cal 1 | Cal 2 | Cal 3 | | | | | Sample | Mean | Min | Max |
| Sample | Origin | (2.7 ng/mL) | (21 ng/mL) | (108 ng/mL) | Sample | Slope | Intercept | $r^2$ | (ng/mL) | (ng/mL) | (ng/mL) | (ng/mL) |
| 151B | 0 | 117 | 488 | 2219 | 195 | 20.220 | 40.241 | 0.9992 | 7.65 | 8.9 | 4.7 | 13.1 |
| 149B | 0 | 86 | 433 | 2063 | 213 | 18.919 | 22.586 | 0.9997 | 10.06 | 11.7 | 7.2 | 16.2 |
| 153C | 0 | 90 | 469 | 1980 | 233 | 18.047 | 40.549 | 0.9984 | 10.66 | 11.9 | 6.8 | 17 |
| 148B | 0 | 85 | 461 | 2032 | 205 | 18.581 | 32.726 | 0.9990 | 9.27 | 11.7 | 7.2 | 16.2 |
| 153A | 0 | 85 | 453 | 1821 | 403 | 16.556 | 44.644 | 0.9973 | 21.65 | 20.1 | 12.6 | 27.6 |
| 148C | 0 | 88 | 494 | 1955 | 167 | 17.775 | 49.003 | 0.9968 | 6.64 | 5.8 | 3.1 | 8.5 |
| 150C | 0 | 85 | 460 | 1789 | 312 | 16.236 | 48.920 | 0.9963 | 16.20 | 17.7 | 10.8 | 24.6 |
| 157A | 0 | 99 | 458 | 1810 | 334 | 16.388 | 52.185 | 0.9968 | 17.20 | 19.1 | 11.9 | 26.3 |
| 157C | 0 | 78 | 452 | 1902 | 218 | 17.367 | 36.200 | 0.9983 | 10.47 | 9.1 | 5.2 | 13 |
| 155B | 0 | 95 | 489 | 2032 | 258 | 18.499 | 44.919 | 0.9980 | 11.52 | 13.7 | 8.3 | 19.1 |

Experiment 2

In the second experiment the internal calibrators spanned the concentration range from approximately 2 ng/mL to 22 ng/mL and nineteen sirolimus IPT samples were analyzed. The individual calibration lines constructed including the origin are shown in FIG. 14A-D and the calculated sirolimus concentrations are shown in Table 15 Table 16. For all nineteen samples, the calculated concentration of sirolimus was within the acceptable range of the IPT scheme whether calculated including or excluding the origin.

TABLE 15

Experiment 2: The sirolimus concentration in nineteen IPT samples determined using the three internal calibrators. The calculated results for all samples was in the acceptable range for the scheme (ie IPT Min ≤ Result ≤ IPT Max).

| | Integrated Peak Area | | | | Regression Analysis | | | Result | IPT | | |
|---|---|---|---|---|---|---|---|---|---|---|---|
| | Cal 1 | Cal 2 | Cal 3 | | | | | Sample | Mean | Min | Max |
| Sample | 1.7 ng/mL | 17.5 ng/mL | 22.1 ng/mL | Sample | Slope | Intercept | r² | (ng/mL) | (ng/mL) | (ng/mL) | (ng/mL) |
| S150C | 82.9 | 544.3 | 708.3 | 483.9 | 30.140 | 29.864 | 0.9984 | 15.06 | 17.7 | 10.8 | 24.6 |
| S150B | 103.3 | 506.1 | 691.9 | 276.1 | 27.854 | 49.960 | 0.9903 | 8.12 | 8.5 | 2.5 | 14.5 |
| S148A | 100.7 | 474.5 | 702.7 | 234.6 | 27.867 | 41.990 | 0.9716 | 6.91 | 9.0 | 3.3 | 14.7 |
| S148B | 71.2 | 453.7 | 550.8 | 292.5 | 23.581 | 33.650 | 0.9995 | 10.98 | 11.7 | 7.2 | 16.2 |
| S148C | 84.2 | 423.6 | 587.7 | 164.8 | 23.743 | 38.010 | 0.9880 | 5.34 | 5.8 | 3.1 | 8.5 |
| S149A | 55.6 | 348.8 | 478.1 | 109.8 | 20.060 | 17.755 | 0.9923 | 4.59 | 3.8 | 2.0 | 5.6 |
| S149B | 88 | 382.9 | 491.2 | 215.8 | 19.390 | 53.528 | 0.9978 | 8.37 | 8.8 | 2.8 | 14.8 |
| S149C | 69.8 | 384.5 | 581.3 | 169.6 | 23.630 | 19.599 | 0.9694 | 6.35 | 7.7 | 4.1 | 11.3 |
| S146C | 91.1 | 410.8 | 630.8 | 172.2 | 24.732 | 36.787 | 0.9598 | 5.48 | 5.9 | 3.2 | 8.6 |
| S146B | 74.7 | 408.1 | 598.7 | 187.7 | 24.387 | 24.471 | 0.9770 | 6.69 | 8.1 | 4.5 | 11.7 |
| S141B | 95.8 | 483.1 | 666.7 | 263.1 | 26.962 | 43.695 | 0.9890 | 8.14 | 9.7 | 5.2 | 14.2 |
| S142C | 89.2 | 428.4 | 583.4 | 185.2 | 23.403 | 44.524 | 0.9908 | 6.01 | 8.1 | 5.4 | 10.8 |
| S142B | 71.9 | 429.7 | 664.1 | 89.8 | 27.252 | 13.066 | 0.9649 | 2.82 | 3.3 | 1.5 | 5.1 |
| S142A | 78.8 | 383.4 | 623.8 | 251.5 | 24.678 | 21.968 | 0.9434 | 9.30 | 11.7 | 7.8 | 15.6 |
| S141C | 67.8 | 353.6 | 603.8 | 267.1 | 24.046 | 10.407 | 0.9289 | 10.68 | 13.2 | 7.5 | 18.9 |
| S146A | 77.8 | 436.6 | 613.7 | 96.7 | 25.231 | 28.372 | 0.9869 | 2.71 | 5.0 | 2.6 | 7.4 |
| S145C | 64.2 | 366.7 | 506.7 | 87.8 | 20.935 | 24.065 | 0.9902 | 3.04 | 3.9 | 1.8 | 6.0 |
| S143C | 75.2 | 392.4 | 652.6 | 79.6 | 26.055 | 14.389 | 0.9382 | 2.50 | 3.6 | 1.8 | 5.4 |
| S143B | 89.3 | 389.8 | 585.4 | 188.3 | 22.842 | 40.096 | 0.9656 | 6.49 | 9.4 | 5.5 | 13.3 |

TABLE 16

Experiment 2: The sirolimus concentration in nineteen IPT samples determined using the three internal calibrators plus the origin. The calculated results for all samples was in the acceptable range for the scheme (ie IPT Min ≤ Result ≤ IPT Max)

| | Integrated Peak Area | | | | | Regression Analysis | | | Result | IPT | | |
|---|---|---|---|---|---|---|---|---|---|---|---|---|
| | | Cal 1 | Cal 2 | Cal 3 | | | | | Sample | Mean | Min | Max |
| Sample | Origin | 1.7 ng/mL | 17.5 ng/mL | 22.1 ng/mL | Sample | Slope | Intercept | r² | (ng/mL) | (ng/mL) | (ng/mL) | (ng/mL) |
| S150C | 0 | 82.9 | 544.3 | 708.3 | 483.9 | 30.967 | 13.859 | 0.9979 | 15.18 | 17.7 | 10.8 | 24.6 |
| S150B | 0 | 103.3 | 506.1 | 691.9 | 276.1 | 29.237 | 23.186 | 0.9910 | 8.65 | 8.5 | 2.5 | 14.5 |
| S148A | 0 | 100.7 | 474.5 | 702.7 | 234.6 | 29.029 | 19.487 | 0.9811 | 7.41 | 9.0 | 3.3 | 14.7 |
| S148B | 0 | 71.2 | 453.7 | 550.8 | 292.5 | 24.512 | 15.616 | 0.9974 | 11.30 | 11.7 | 7.2 | 16.2 |
| S148C | 0 | 84.2 | 423.6 | 587.7 | 164.8 | 24.795 | 17.640 | 0.9903 | 5.94 | 5.8 | 3.1 | 8.5 |
| S149A | 0 | 55.6 | 348.8 | 478.1 | 109.8 | 20.552 | 8.240 | 0.9945 | 4.94 | 3.8 | 2.0 | 5.6 |
| S149B | 0 | 88 | 382.9 | 491.2 | 215.8 | 20.871 | 24.841 | 0.9907 | 9.15 | 8.8 | 2.8 | 14.8 |
| S149C | 0 | 69.8 | 384.5 | 581.3 | 169.6 | 24.172 | 9.096 | 0.9809 | 6.64 | 7.7 | 4.1 | 11.3 |
| S146C | 0 | 91.1 | 410.8 | 630.8 | 172.2 | 25.750 | 17.072 | 0.9742 | 6.02 | 5.9 | 3.2 | 8.6 |
| S146B | 0 | 74.7 | 408.1 | 598.7 | 187.7 | 25.064 | 11.357 | 0.9853 | 7.04 | 8.1 | 4.5 | 11.7 |
| S141B | 0 | 95.8 | 483.1 | 666.7 | 263.1 | 28.171 | 20.278 | 0.9908 | 8.62 | 9.7 | 5.2 | 14.2 |
| S142C | 0 | 89.2 | 428.4 | 583.4 | 185.2 | 24.635 | 20.663 | 0.9908 | 6.68 | 8.1 | 5.4 | 10.8 |
| S142B | 0 | 71.9 | 429.7 | 664.1 | 89.8 | 27.613 | 6.064 | 0.9783 | 3.03 | 3.3 | 1.5 | 5.1 |
| S142A | 0 | 78.8 | 383.4 | 623.8 | 251.5 | 25.285 | 10.195 | 0.9650 | 9.54 | 11.7 | 7.8 | 15.6 |
| S141C | 0 | 67.8 | 353.6 | 603.8 | 267.1 | 24.334 | 4.830 | 0.9556 | 10.78 | 13.2 | 7.5 | 18.9 |
| S146A | 0 | 77.8 | 436.6 | 613.7 | 96.7 | 26.016 | 13.167 | 0.9909 | 3.21 | 5.0 | 2.6 | 7.4 |
| S145C | 0 | 64.2 | 366.7 | 506.7 | 87.8 | 21.601 | 11.168 | 0.9928 | 3.55 | 3.9 | 1.8 | 6.0 |
| S143C | 0 | 75.2 | 392.4 | 652.6 | 79.6 | 26.453 | 6.678 | 0.9616 | 2.76 | 3.6 | 1.8 | 5.4 |
| S143B | 0 | 89.3 | 389.8 | 585.4 | 188.3 | 23.951 | 18.608 | 0.9770 | 7.08 | 9.4 | 5.5 | 13.3 |

In addition to the IPT samples, ten replicates of a low (approximately 2.5 ng/mL), medium (approximately 7.5 ng/mL) and high (approximately 15 ng/mL) whole blood sirolimus QC were analyzed. The results are shown in Table 17 and demonstrate that intra-assay imprecision is less than 6% across the three QCs.

TABLE 17

Intra-assay imprecision for three QC samples that span the analytical range of the assay.

| QC | Low (2.5 ng/mL) | Med (7.5 ng/mL) | High (15 ng/mL) |
|---|---|---|---|
| Replicate 1 | 2.95 | 8.43 | 15.92 |
| Replicate 2 | 2.60 | 7.61 | 15.99 |
| Replicate 3 | 2.49 | 7.26 | 15.39 |
| Replicate 4 | 2.69 | 7.38 | 17.74 |
| Replicate 5 | 2.39 | 8.20 | 16.68 |
| Replicate 6 | 2.63 | 7.59 | 17.75 |
| Replicate 7 | 2.47 | 7.51 | 17.14 |
| Replicate 8 | 2.60 | 7.71 | 17.13 |
| Replicate 9 | 2.39 | 7.56 | 18.00 |
| Replicate 10 | 2.58 | 7.76 | 15.56 |
| Mean | 2.58 | 7.70 | 16.73 |
| SD | 0.1647 | 0.3580 | 0.9656 |
| % CV | 6.4 | 4.6 | 5.8 |

Conclusions
1. Accurate and precise results for the measurement of sirolimus concentrations in whole blood samples can be obtained using internal calibration.
2. Where stable isotope analogs of the analyte of interest are not available, structural analogs can be used provided the relative response factors are carefully measured.
3. It can be useful to include the origin (x=0, y=0) as an additional calibrator.
4. Three calibrators spanning the range from approximately 2 ng/mL to approximately 100 ng/mL were sufficient to provide accurate results for samples that had concentration values clustered in the range approximately 2 ng/mL to approximately 15 ng/mL suggesting that internal calibration can provide accurate quantification over a wide dynamic range with a small number of calibrators.
5. This example demonstrates that for some analytes at least, internal calibrators can be introduced at different stages in the sample preparation process with acceptable outcome. This flexibility can be important in the development and optimization of automated instruments to implement the invention in a routine laboratory.

Example 3: The Analysis of Hydromorphone in Human Urine Using Multipoint Calibration in a Single Analysis Introduction:
Hydromorphone is a potent semi-synthetic opioid drug. It is used to provide relief from pain in extreme situations and where morphine is not effective. The drug can be addictive so it's use and withdrawal after therapy are carefully controlled. Hydromorphone is one of a number of prescription drugs where abuse is increasing. Methods for monitoring hydromorphone concentrations are therefore important both for clinical toxicology and forensic toxicology applications.

Methods

External Calibration:
External calibrators were prepared by spiking hydromorphone into blank human urine.

Quality Control Samples:
Low, medium and high QCs were prepared by spiking hydromorphone into replicate aliquots of blank human urine at concentrations of approximately 187.5 ng/mL, 375 ng/mL and 1250 ng/mL hydromorphone. A commercial urine QC containing 100 ng/mL hydromorphone was also obtained from UTAK.

Internal Calibrator Selection:
The selected internal calibrators and their specific MRM transitions are show in Table 18.

TABLE 18

The analyte, selected internal calibrators and their specific MRM transitions.

| Analyte/Internal calibrator | Type | MRM Transition |
|---|---|---|
| Hydromorphone | Analyte | 286.1 > 185.1 |
| oxymorphone-d3 | stable isotope labelled structural analogue | 305.1 > 230.1 |
| hydromorphone-d4 | Stable isotope labelled analogue | 290.1 > 186.0 |
| hydromorphine-d6 | Stable Isotope labelled analogue | 292.1 > 185.0 |

Sample Preparation
1. Aliqot 250 μL urine sample/calibrator/QC into a 2 mL Eppendorf tube and spike with 10 μL internal calibrator mix.
2. Add 125 μL tetraborate buffer (Saturated solution of disodium tetraborate decahydrate) to 260 μL urine sample/calibrator/QC with internal calibrators.
3. Add 750 μL extraction mixture (DCM:MeOH [90:10]) and vortex 30 s.
4. Centrifuge for 5 min at 13000 rpm. Take off lower organic layer and transfer to clean Eppendorf tube.
5. Repeat organic extraction and pool extracts in the same Eppendorf tubes.
6. Dry the extracts down under $N_2$ at 40° C. for approx 10 min until dry.
7. Reconstitute in 200 μL mobile phase A (1.25× concentration step) and transfer to Total Recovery vials for UPLC/MS/MS analysis.

UPLC/MS/MS

Sample extracts were analyzed using an ACQUITY UPLC with a gradient of acetonitrile in 0.2 mM ammonium formate buffer (Table 19) and a Waters TQD mass spectrometer operated in ESI+ve mode (Table 20).

Hydromorphone was extracted from urine samples using a liquid-liquid extraction procedure as detailed below:

TABLE 19

The chromatography conditions used to analyse the urine samples after LLE.

| Time (mins) | Flow (mL/min) | % A | % B | Curve |
|---|---|---|---|---|
| 0 | 0.5 | 98 | 2 | — |
| 1.0 | 0.5 | 98 | 2 | 6 |
| 2.5 | 0.5 | 90 | 10 | 6 |
| 5.5 | 0.5 | 78 | 22 | 6 |
| 7.5 | 0.5 | 58 | 42 | 6 |
| 8.0 | 0.5 | 5.0 | 95 | 1 |
| 10.0 | 0.5 | 98 | 2 | 1 |

A = 0.2 mM ammonium formate and B = acetonitrile.

TABLE 20

MS/MS conditions for each of the internal calibrators, analyte and internal standard.

| Compound | Precursor (m/z) | Product (m/z) | Dwell (secs) | Cone (V) | Collision (eV) |
|---|---|---|---|---|---|
| Hydromorphone | 286.1 | 185.1 | 0.05 | 55 | 30 |
| Hydromorphone-d4 | 290.1 | 186.1 | 0.05 | 50 | 30 |
| Hydromorphone-d6 | 292.1 | 185.0 | 0.05 | 50 | 30 |
| Oxymorphone | 302.1 | 227.1 | 0.05 | 35 | 25 |
| Oxymorphone-d3 | 305.1 | 230.1 | 0.05 | 40 | 30 |

Experiment 1

The MS/MS response for the internal calibrators was measured by analysing a mixture of 0.1 μg/mL hydromorphone and 0.1 μg/mL of each of the internal calibrators diluted into solvent. The internal calibrators and the calculated relative responses are shown in Table 21.

TABLE 21

The MS/MS response for equal concentrations of each internal calibrator relative to the response for hydromorphone.

| Analyte/Internal calibrator | Relative Response Factor | Final Apparent Concentration (ng/mL) |
|---|---|---|
| Hydromorphone | 1.0 | — |
| oxymorphone-d3 | 0.31 | 50 |
| hydromorphine-d6 | 0.68 | 500 |
| hydromorphone-d4 | 0.93 | 1500 |

Using the calculated relative response factors, a mixture of internal calibrators was prepared such that when 10 μL was spiked into 250 μL of sample, the final apparent concentrations were 50 ng/mL, 500 ng/mL or 1500 ng/mL (Table 21).

A series of traditional external calibrators was also prepared at the following concentrations: 20 ng/mL, 50 ng/mL, 100 ng/mL, 250 ng/mL, 500 ng/mL, 750 ng/mL, 1000 ng/mL and 1500 ng/mL.

QC samples for analysis using internal calibration were spiked with a mixture of the three internal calibrators to give a final apparent concentration of 50 ng/mL, 500 ng/mL and 1500 ng/mL (Table 21).

Conventional internal standard (hydromorphone-d6) was added to the external calibrators and to the QC samples for analysis by external calibration.

All samples were processed by liquid-liquid extraction and LC/MS/MS using the conditions described above.

Results

Five replicates of each QC level were analysed twice using traditional external calibration and twice using the internal calibration method. A single preparation of the UTAK QC was analysed in duplicate by both calibration methods. The results of the analyses are shown in Tables 22 and 23 and an example internal calibration line is shown in FIG. 15.

TABLE 22

The mean values for the results of five replicates, each analysed twice (QCs) or two replicates each analysed twice (UTAK), determined using Internal Calibration.
Internal Calibration

| GRAND MEANS | Mean (ng/mL) | SD | % CV |
|---|---|---|---|
| Low QC | 192.6 | 12.91 | 6.70 |
| Medium QC | 334.3 | 11.95 | 3.57 |
| High QC | 1119.0 | 67.69 | 6.05 |
| UTAK QC | 86.6 | 5.31 | 6.13 |

TABLE 23

The mean values for the results of five replicates, each analysed twice (QCs) or two replicates each analysed twice (UTAK), determined using external Calibration.
External Calibration

| GRAND MEANS | Mean (ng/mL) | SD | % CV |
|---|---|---|---|
| Low QC | 231.5 | 13.44 | 5.81 |
| Medium QC | 397.3 | 15.00 | 3.78 |
| High QC | 1332.4 | 57.32 | 4.30 |
| UTAK QC | 100.5 | 1.23 | 1.22 |

The results of the Internal Calibration method correlate well with those of the External Calibration method (FIG. 16; $R^2=1.000$) but the slope (FIG. 16; 0.84) suggests that in this experiment, the internal calibration method underestimates the true concentration by approximately 16%.

Experiment 2

Value Assignment:

In a second experiment, the internal calibrators were spiked into five replicate aliquots of blank human urine. Internal standard (oxymorphone) was also added to the samples and to a series of external calibrators. All samples were processed by liquid extraction and analyzed by LC/MS/MS as described above (see Methods). This allowed the apparent concentration of each of the internal calibrators to be measured accurately against the hydromorphone external calibration line using conventional techniques.

Using these assigned values for the internal calibrators (instead of the Relative Response Factor used in Experiment 1) a fresh mixture of internal calibrators was prepared, again targeting final apparent concentrations of 50 ng/mL, 500 ng/mL and 1500 ng/mL. Five replicates of the low, medium and high QC and 2 replicates of the UTAK QC were analyzed using internal calibration and two replicates of each QC were analyzed by conventional external calibration. The individual internal calibrations for each sample are shown in FIG. 17A-C.

The results of the QC analyses by internal and external calibration are shown in Table 24 and in FIG. 18.

TABLE 24

Mean hydromorphone concentration values for the QC samples assayed in experiment 2 using External and Internal calibration.

| QC | External Calibration (ng/mL; mean of 2) | Internal Calibration (ng/mL; mean of 5) |
|---|---|---|
| Low | 229.3 | 213.1 |
| Medium | 446.7 | 405.2 |

TABLE 24-continued

Mean hydromorphone concentration values for the QC samples assayed in experiment 2 using External and Internal calibration.

| QC | External Calibration (ng/mL; mean of 2) | Internal Calibration (ng/mL; mean of 5) |
|---|---|---|
| High | 1230.1 | 1308.9 |
| UTAK | 115.3 | 125.9 |

Again, there is a good correlation between the results obtained using the two calibration procedures (FIG. 18; $R^2=0.9962$) and in this case, the slope of 1.08 indicates good agreement (average error≤8%) between the two methods.

Discussion

In the first experiment, a simple relative response factor was used to calculate the apparent concentration of the internal calibrators. This process did not take into account any effects of the sample preparation process. The QC values determined by internal calibration correlate well with those determined by external calibration ($R^2=1.000$; FIG. 16) but in this experiment the slope of the correlation line (0.84; FIG. 16) indicates an approximately 16% underestimation of the concentration by internal calibration.

In a second experiment, the internal calibrator concentrations were assigned by comparison to an external calibration line. In this process all internal and external calibrators were prepared in urine matrix and were subjected to the liquid extraction sample preparation process. The results show a much closer agreement in the QC values determined using external and internal calibration (FIG. 18; $R^2=0.9962$ and slope=1.07) suggesting that the liquid extraction sample preparation process may have contributed to the apparent poor agreement seen in experiment 1.

Conclusions

Hydromorphone can be accurately quantified in human urine using the internal calibration approach with a mixture of stable isotope labelled analogues and a stable isotope labelled structural analog.

Multiple methods of internal calibrator value assignment can be explored to determine the best approach for each analyte/matrix/sample preparation method combination.

Summary

Internal calibration can provide an accurate and precise alternative to conventional calibration and can allow for random access analysis (which is not allowed by conventional batch mode of analysis). Thus, for the user, internal calibration can provide reduced time to first result, streamline workflow, reduce reagent consumption, and provide perfectly matrix-matched calibration for every sample. For the manufacturer, internal calibration can provide new compositions, kits, and instrument designs, as well as simplified manufacturing processes since separate matrices are not required.

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

The invention claimed is:

1. A method of quantifying a target analyte by mass spectrometry, the method comprising:
    preparing a single sample by combining a first known quantity of a first calibrator, a second known quantity of a second calibrator, and a third known quantity of a third calibrator in a single sample comprising the target analyte,
    wherein the target analyte is an organic molecule comprising at least 3 carbon atoms,
    wherein the first calibrator, the second calibrator, and the third calibrator are each different stable isotope analogs of the target analyte,
    wherein the target analyte is unlabeled,
    wherein amount of the first calibrator, the second calibrator, and the third calibrator each differ exponentially with a base of 10 and an integer exponent;
    generating a mass spectrometer signal from the single sample using a mass spectrometer comprising a first calibrator signal, comprising a second calibrator signal, comprising a third calibrator signal, and comprising a target analyte signal,
    wherein the first known quantity, the second known quantity, and the third known quantity are different, and wherein the first calibrator, the second calibrator, the third calibrator and the target analyte are each distinguishable in the single sample by mass spectrometry due to differences in their mass, fragmentation pattern or combinations thereof;
    obtaining a calibration curve, wherein the calibration curve is obtained from the first calibrator signal, the second calibrator signal and third calibrator signal; and
    quantifying the target analyte using the calibration curve and the target analyte signal.

2. The method of claim 1, wherein a quantity range defined by the first, second and third calibrators for the target analyte spans an expected analytical range of the target analyte in the sample.

3. The method of claim 1, further comprising: separating the first calibrator, the second calibrator, the third calibrator and the target analyte from other components of the single sample prior to obtaining the mass spectrometer signal.

4. The method of claim 3, wherein the separation comprises chromatography and the first calibrator, the second calibrator, the third calibrator and the target analyte co-elute.

5. The method of claim 3, wherein the separation comprises chromatography and the first calibrator, the second calibrator, the third calibrator and the target analyte elute separately.

6. The method of claim 3, wherein the separation comprises at least one of solid phase extraction, liquid chromatography, gas chromatography, affinity, immunoaffinity, and supercritical fluid chromatography.

7. The method of claim 1, further comprising:
    obtaining, from the mass spectrometer signal, a fourth calibrator signal, a fifth calibrator signal, a sixth calibrator signal, and an additional target analyte signal from the single sample comprising a fourth known quantity of a fourth calibrator, comprising a fifth known quantity of a fifth calibrator, comprising a sixth known quantity of a sixth calibrator, and comprising an additional target analyte, wherein the additional target analyte is an organic molecule comprising at least 3 carbon atoms, and is unlabeled,
wherein the fourth calibrator, the fifth calibrator, and the sixth calibrator are each different stable isotope analogs of the additional target analyte,
wherein the fourth known quantity, the fifth known quantity and the sixth known quantity are different, wherein a quantity range defined by the fourth, fifth and sixth calibrators for the additional target analyte spans an expected analytical range of the additional target analyte in the sample and the amount of the fourth calibrator, the fifth calibrator, and the sixth calibrator each differ exponentially with a base of 10 and an integer exponent, and
wherein the first calibrator, the second calibrator, the third calibrator, the fourth calibrator, the fifth calibrator, the sixth calibrator, the target analyte, and the additional target analyte are each distinguishable in the single sample by mass spectrometry due to differences in their mass, fragmentation pattern or combinations thereof; and obtaining a second calibration curve, wherein the second calibration curve is obtained from the fourth calibrator signal, the fifth calibrator signal and sixth calibrator signal, and quantifying the additional target analyte using the second calibration curve and the additional target analyte signal.

8. The method of claim 1, further comprising
calculating a relative response factor for each calibrator, and
correcting the first known quantity of the first calibrator, the second known quantity of a second calibrator, and the third known quantity of a third calibrator using the relative response factor for each calibrator.

9. The method of claim 1, wherein the quantity of the first calibrator is about 10% of an expected quantity of the target analyte, the quantity of the second calibrator is about 100% of the expected quantity of the target analyte, and the quantity of the third calibrator is about 1000% of the expected quantity of the target analyte.

10. The method of claim 8, wherein the relative response factor for each calibrator is calculated by analyzing each calibrator using the mass spectrometer against a standard reference for the analyte.

11. The method of claim 1, wherein the target analyte is a steroid.

12. The method of claim 1, wherein the target analyte is testosterone.

13. The method of claim 1, wherein the target analyte is an immunosuppressant.

14. The method of claim 1, wherein the target analyte is an opioid.

15. The method of claim 1, wherein the target analyte is hydromorphone.

16. The method of claim 2, wherein the quantity range defined by the first, second and third calibrators for the target analyte comprises 2 ng/mL and 100 ng/mL.

17. The method of claim 1, wherein the target analyte is a clinical chemistry target analyte.

18. The method of claim 1, wherein the target analyte is a pharmacology target analyte.

* * * * *